(12) United States Patent
Springate et al.

(10) Patent No.: US 11,419,891 B2
(45) Date of Patent: Aug. 23, 2022

(54) HIGH-MOLECULAR-WEIGHT FUCANS FOR TREATING FIBROUS ADHESIONS AND OTHER DISEASES AND CONDITIONS

(71) Applicant: ARC Medical Devices Inc., Richmond (CA)

(72) Inventors: Christopher Michael Kevin Springate, Richmond (CA); Ian Millet, Richmond (CA); Sailesh Haresh Daswani, Richmond (CA); Hesong Sun, Richmond (CA)

(73) Assignee: ARC Medical Devices Inc., Richmond (CA)

( * ) Notice: Subject to any disclaimer, the term of this patent is extended or adjusted under 35 U.S.C. 154(b) by 0 days.

(21) Appl. No.: 17/260,272

(22) PCT Filed: Jul. 24, 2019

(86) PCT No.: PCT/CA2019/051027
§ 371 (c)(1),
(2) Date: Jan. 14, 2021

(87) PCT Pub. No.: WO2020/019078
PCT Pub. Date: Jan. 30, 2020

(65) Prior Publication Data
US 2021/0292441 A1    Sep. 23, 2021

Related U.S. Application Data

(60) Provisional application No. 62/861,228, filed on Jun. 13, 2019, provisional application No. 62/861,223, filed on Jun. 13, 2019, provisional application No. 62/861,235, filed on Jun. 13, 2019, provisional application No. 62/793,654, filed on Jan. 17, 2019, provisional application No. 62/793,514, filed on Jan. 17, 2019, provisional application No. 62/755,328, filed on Nov. 2, 2018, provisional application No. 62/755,311, filed on Nov. 2, 2018, provisional application No. 62/755,318, filed on Nov. 2, 2018, provisional application No. 62/722,135, filed on Aug. 23, 2018, provisional application No. 62/722,137, filed on Aug. 23, 2018, provisional application No. 62/713,392, filed on Aug. 1, 2018, provisional application No. 62/713,399, filed on Aug. 1, 2018, provisional application No. 62/713,413, filed on Aug. 1, 2018, provisional application No. 62/711,335, filed on Jul. 27, 2018, provisional application No. 62/711,364, filed on Jul. 27, 2018, provisional application No. 62/711,372, filed on Jul. 27, 2018.

(51) Int. Cl.
*A61K 31/737* (2006.01)
*A61P 41/00* (2006.01)
*C08B 37/00* (2006.01)

(52) U.S. Cl.
CPC ............ *A61K 31/737* (2013.01); *A61P 41/00* (2018.01); *C08B 37/0003* (2013.01); *C08B 37/0063* (2013.01)

(58) Field of Classification Search
None
See application file for complete search history.

(56) References Cited

U.S. PATENT DOCUMENTS

| | | | |
|---|---|---|---|
| 8,466,125 B2 * | 6/2013 | Springate | A61K 8/73 514/54 |
| 2009/0170801 A1 * | 7/2009 | Hao | A61K 9/2054 514/44 R |

\* cited by examiner

*Primary Examiner* — Layla D Berry
(74) *Attorney, Agent, or Firm* — King IP Law; Joshua King

(57) ABSTRACT

High-molecular-weight fucan compositions comprising a therapeutically effective, medically acceptable fucan in a composition comprising wherein the fucan, for example, has a molecular weight distribution in which more than 60% w/w of the composition has a molecular weight above 100 kDa.

18 Claims, 11 Drawing Sheets

Base-treated Sample B

Unmodified Sample A

HIGH-MOLECULAR-WEIGHT FUCANS FOR TREATING FIBROUS ADHESIONS AND OTHER DISEASES AND CONDITIONS

CLAIM FOR PRIORITY

The present application claims the benefit of United States provisional patent application Ser. No. 62/711,364, filed Jul. 27, 2018; United States provisional patent application Ser. No. 62/711,372, filed Jul. 27, 2018; U.S. provisional patent application No. 62/711,335, filed Jul. 27, 2018; U.S. Provisional Patent Application Ser. No. 62/713,399, filed Aug. 1, 2018; U.S. provisional patent application No. 62/722,135, filed Aug. 23, 2018; U.S. provisional patent application No. 62/755,311, filed Nov. 2, 2018; U.S. provisional patent application No. 62/793,514, filed on Jan. 17, 2019; U.S. provisional patent application No. 62/861,223, filed Jun. 13, 2019; U.S. Provisional Patent Application Ser. No. 62/713,392, filed Aug. 1, 2018; U.S. provisional patent application No. 62/713,413, filed Aug. 1, 2018; U.S. provisional patent application No. 62/722,137, filed Aug. 23, 2018; U.S. provisional patent application No. 62/755,318, filed on Nov. 2, 2018; U.S. provisional patent application No. 62/861,228, filed Jun. 13, 2019; U.S. Provisional Patent Application Ser. No. 62/755,328, filed Nov. 2, 2018; U.S. provisional patent application No. 62/793,654, filed Jan. 17, 2019; and, U.S. provisional patent application No. 62/861,235, filed Jun. 13, 2019, all of which applications are incorporated herein by reference in their entirety.

BACKGROUND

Fucans (including fucoidan) are sulfated polysaccharides. In general terms, this means that they are molecules made up of a number of sugar groups, and also have sulfur atoms attached to the sugar groups. The main sugar group is called "fucose", which is sugar that has 6 carbon atoms and has the chemical formula $C_6H_{12}O_5$. "Fucoidan" (or fucoidin) indicates fucans derived from brown algae (seaweed). Fucans can exist alone, or in a mixture of other sugars, for example in a mixture of sugars such as xylose, galactose, glucose, glucuronic acid and/or mannose. These other sugars may be extracted from the seaweed or other source with the fucan. Although fucans are currently derived from natural sources such as the brown algae (seaweeds), sea cucumbers, etc., mentioned herein, "fucan" includes polymer molecules having the chemical and structural motifs of the fucans as discussed herein regardless of the ultimate source(s) of the fucans.

Fucoidan can be obtained from a variety of species of brown algae including but not limited to: *Adenocystis utricularis, Ascophyllum nodosum, Chorda filum, Cystoseirabies marina, Durvillaea antarctica, Ecklonia kurome, Ecklonia maxima, Eisenia bicyclis, Fucus evanescens, Fucus vesiculosis, Hizikia fusiforme, Himanthalia Elongata, Kjellmaniella crassifolia, Laminaria brasiliensis, Laminaria cichorioides, Laminaria hyperborea, Laminaria japonica, Laminaria saccharina, Lessonia trabeculata, Macrocystis pyrifera, Pelvetia fastigiata, Pelvetia Canaliculata, Saccharina japonica, Saccharina latissima, Sargassum stenophylum, Sargassum thunbergii, Sargassum confusum, Sargassum fusiforme* and *Undaria pinnatifida*. These exemplary species are all from the taxonomic class Phaeophyceae and the majority of these species fall into the families of Fucales and Laminariaceae.

Fucans including fucoidan have been shown to be efficacious in serving to inhibit, prevent, remove, reduce, or otherwise treat the formation of fibrous adhesions. They have also found use in the treatment of other related diseases and conditions.

Thus, there has gone unmet a need for compositions comprising fucans having desired high-molecular-weights, including in some embodiments such compositions being modified to have desired sulfation levels and/or medically viable, low endotoxin levels. The present compositions, systems and methods, etc., provide these and/or other advantages.

SUMMARY

The present compositions, systems, devices, materials and methods, etc., provide high-molecular-weight fucans. Such high-molecular-weight fucans can be obtained from feedstock fucan compositions or other starting or initial fucan compositions that have fucans with a broad molecular weight distribution comprising a desired high-molecular-weight segment/portion (i.e., broad molecular weight fucan compositions from which the high-molecular weight fucans can be derived; such starting fucan compositions may or may not be crude or have been previously processed or purified). The desired high-molecular-weight fucan has a molecular weight distribution consisting essentially of the desired high-molecular-weight segment/portion of the starting fucan broad molecular weight distribution wherein a substantial quantity of the broad molecular weight distribution at the low molecular weight end has been eliminated, suppressed, or otherwise attenuated such that any remaining amounts are inconsequential.

In some aspects, the compositions, systems, methods, etc., herein comprise high-molecular-weight fucans such as fucoidans can comprise, consist essentially of, or consist of. a molecular weight distribution wherein at least 60% w/w of the distribution can be greater than 100 kDa when measured using an aqueous gel permeation chromatography set up consisting essentially of:

one 300 mm analytical gel permeation chromatography column with a 7.8 mm inner diameter packed with hydroxylated polymethacrylate-based gel, having an effective molecular weight range of can be between about 50 kDa and about 5,000 kDa, one 300 mm analytical gel permeation chromatography column with a 7.8 mm inner diameter packed with hydroxylated polymethacrylate-based gel, having an effective molecular weight range of can be between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;

a refractive index detector at about 30° C.;

0.1M sodium nitrate mobile phase run at 0.6 mL/min; and quantification against a peak molecular weight standard curve consisting essentially of a first dextran standard with a peak molecular weight of about 2,200 kDa, a second dextran standard with a peak molecular weight of can be between about 720 kDa and about 760 kDa, a third dextran standard with a peak molecular weight can be between about 470 kDa and about 510 kDa, a fourth dextran standard with a peak molecular weight can be between about 370 kDa and about 410 kDa, a fifth dextran standard with a peak molecular weight can be between about 180 kDa and about 220 kDa, and a sixth dextran standard with a peak molecular weight can be between about 40 kDa and 55 kDa.

In some embodiments, at least about 70% w/w, 80% w/w, 90% w/w, 93% w/w, 94% w/w, 95% w/w, 97% w/w, 98% w/w, or 99% w/w of the distribution can be greater than 100 kDa. The weight average molecular weight can be between about 100 kDa and 10,000 kDa; between about 140 kDa and 8,100 kDa; between about 370 kDa and 8100 kDa; between about 370 kDa and 5300 kDa; between about 370 kDa and 8100 kDa; between about 370 kDa and 5300 kDa; between about 370 kDa and 1900 kDa; between about 590 kDa and 1600 kDa; between about 590 kDa and 1600 kDa; or between about 860 kDa and 1600 kDa. In some embodiments, the weight average molecular weight can be about 1,100 kDa, about 1,200 kDa, or about 1,300 kDa. The number average molecular weight can be between about 50 kDa and 3,000 kDa; between about 60 kDa and 2,000 kDa; between about 140 kDa and 2,000 kDa; between about 140 kDa and 520 kDa; or between about 230 kDa and 450 kDa. At least 55% w/w, 71% w/w, or 91% w/w of the distribution can be greater than about 200 kDa. At least 22%, 54% w/w, or 90% w/w of the distribution can be greater than about 500 kDa.

In some embodiments, the high-molecular-weight fucans can consist essentially of, comprise, or consist of, a molecular weight distribution wherein can be between about 61% w/w and 80% w/w of the distribution can be between about 200 kDa and 1600 kDa when measured using an aqueous gel permeation chromatography set up as set forth above and elsewhere herein. The high-molecular-weight fucans can consist essentially of, comprise, or consist of, a molecular weight distribution wherein at least 60% w/w of the distribution can be greater than about 1600 kDa when measured using an aqueous gel permeation chromatography set up as set forth above and elsewhere herein.

The sulfate content can be between about 20% w/w and 60% w/w, about 30% w/w and 55% w/w, or about 32% w/w and 52% w/w. The total carbohydrate content can be between about 27% w/w and 80% w/w. The total fucose content as a percentage of the total carbohydrate content can be at least about 30% w/w, 50% w/w, 70% w/w, 80% w/w, 90% w/w or 95% w/w. The total galactose content as a percentage of the total carbohydrate content can be below about 60% w/w, or can be between about 2% w/w and 20% w/w, or can be below about 10% w/w. The total of glucuronic acid, mannose, rhamnose, glucose and xylose content as a percentage of the total carbohydrate content can be below about 30% w/w.

The high-molecular-weight fucans when dissolved in water at a concentration of 50 mg/mL has a viscosity of can be between about 4 cP and 50 cP; between about 10 cP and 40 cP; or between about 15 cP and 30 cP. The high-molecular-weight fucans can be a white solid, and when dissolved in water at a concentration from 1 mg/mL through 100 mg/mL forms a solution that can be one of clear-colorless. The fucan can comprise less than about 5% w/w or 2% w/w acetyl content. The fucan can comprise an acetyl content of substantially 0% w/w when measured by 2D $^1$H-$^{13}$C heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

Also included herein are methods, including methods that can comprise making or using the high-molecular-weight fucans herein, including for treating fibrous adhesions. Further included herein are medically acceptable fucan compositions that can comprise a therapeutically effective amount of the high-molecular-weight fucans in a medically acceptable buffer or diluent. Methods also include treating a condition or disease in an animal that can comprise selecting the medically acceptable fucan compositions herein to treat the condition or disease and administering a therapeutically effective amount comprising between about 0.5 mg/kg and 50 mg/kg; 0.04 mg/kg and 25 mg/kg; 0.2 mg/kg and 10 mg/kg; 1 mg/kg and 5 mg/kg; 1.5 mg/kg and 3 mg/kg; 5 mg/kg and 10 mg/kg.

The condition or disease can be a fibrous adhesion at a target site in the animal, and the administering can comprise administering the therapeutically effective amount to the target site.

The medical compositions can be between about 0.02 mg/mL and 100 mg/mL of the high-molecular-weight fucans, wherein the medical compositions is configured and composed to treat a disease or condition in an animal. The medical compositions can also be between about 0.5 mg/mL and 5 mg/mL, or about 2.5 mg/mL, of the high-molecular-weight fucans.

The medical compositions can be a medical device including a liquid medical device. The medical compositions can be pharmaceutical compositions, which can be liquid pharmaceutical compositions.

The methods herein also include use of a dosage range comprising between about 0.01 mL/kg and 15 mL/kg; about 0.03 mL/kg and 4 mL/kg; about 0.06 mL/kg and 2 mL/kg; or, about 2 mL/kg and 4 mL/kg of the medical compositions to treat a disease or condition in an animal.

The methods for treating fibrous adhesions in a patient can comprise administering the medical compositions to a target site in the patient. The target site can be a surgical site and the administering can be performed at least one of a) after opening a surgical wound at the surgical site, b) during surgery, and c) after closing the surgical wound. The administering can be performed after surgery and before closing the surgical wound. The administering can take less than 3 minutes, 2 minutes or 1 minute. The target site can be at least one of a lesion, abrasion and injury site. The target site can be at least one of a pelvic cavity, an abdominal cavity, a dorsal cavity, a cranial cavity, a spinal cavity, a ventral cavity, a thoracic cavity, a pleural cavity, a pericardial cavity, skin, a joint, a muscle, a tendon and a ligament.

In further embodiments, the methods herein include methods for obtaining a high-molecular-weight fucans. Such methods can comprise:

providing in a starting solution a starting fucan compositions having a broad molecular weight distribution comprising a desired high-molecular-weight fucans segment;

subjecting the starting solution to a first tangential flow filtration across a first higher molecular weight cutoff tangential flow filtration filter to produce a first permeate fucan compositions; and subjecting the first permeate fucan compositions to a second tangential flow filtration across a second lower molecular weight cutoff tangential flow filtration filter to produce a second retentate fucan compositions consisting essentially of the desired high-molecular-weight fucans.

The methods further can comprise collecting the second retentate fucan compositions consisting essentially of the desired high-molecular-weight fucans, and the first higher molecular weight cutoff tangential flow filtration filter has a higher molecular weight cutoff of can be between about 50 kDa and about 1000 kDa and the second lower molecular weight cutoff tangential flow filtration filter has a lower molecular weight cutoff of can be between about 30 kDa and about 100 kDa. The higher molecular weight cutoff can be about 300 kDa and the lower molecular weight cutoff can be about 100 kDa.

Methods for obtaining a high-molecular-weight fucans can comprise:
  providing a starting fucan compositions having a broad molecular weight distribution comprising a desired high-molecular-weight fucans segment in a starting solution;
  subjecting the starting solution to tangential flow filtration across a first lower molecular weight cutoff tangential flow filtration filter to produce a first retentate fucan compositions; and
  subjecting the first retentate fucan compositions to tangential flow filtration across a second higher molecular weight cutoff tangential flow filtration filter to produce a second permeate fucan compositions consisting essentially of the desired high-molecular-weight fucans.

The methods further can comprise collecting the second permeate fucan compositions consisting essentially of the desired high-molecular-weight fucans. The first tangential flow filtration can comprise diafiltering the starting solution across the first lower molecular weight cutoff tangential flow filtration filter. The second tangential flow filtration can comprise diafiltering the first retentate fucan compositions across the second higher molecular weight cutoff tangential flow filtration filter. The first lower molecular weight cutoff tangential flow filtration filter has a lower molecular weight cutoff of can be between about 30 kDa and about 100 kDa and the second higher molecular weight cutoff tangential flow filtration filter has a higher molecular weight cutoff of can be between about 50 kDa and about 1000 kDa. The lower molecular weight cutoff can be about 100 kDa and the higher molecular weight cutoff can be about 300 kDa.

Methods for obtaining a high-molecular-weight fucans can comprise:
  providing a starting fucan compositions having a broad molecular weight distribution comprising a desired high-molecular-weight fucans segment in a starting solution, the starting fucan compositions can comprise low atomic weight cations ionically bound to the sulfate groups on fucan in the compositions; and
  subjecting the starting solution to tangential flow filtration against a cationic additive solution can comprise a cationic additive having a greater molecular weight than the low atomic weight cations to produce a retentate fucan compositions consisting essentially of the desired high-molecular-weight fucans.

The methods further can comprise collecting the retentate fucan compositions consisting essentially of the desired high-molecular-weight fucans. The low atomic weight cations comprise at least one of an alkali metal, an alkaline earth metal, aluminum and ammonium. The cationic additive can comprise at least one of choline, polyvinylpyrrolidone, taurine, polyamine, chitosan, histone, and collagen. The methods further can comprise adding to the starting solution the cationic additive before subjecting the starting solution to tangential flow filtration. The tangential flow filtration can comprise diafiltering the starting solution against the cationic additive solution. The methods still further can comprise removing the cationic additive by diafiltering the retentate fucan compositions against a salt solution over a second tangential flow filtration filter having a molecular weight cutoff that can be lower than a molecular weight cutoff of the first tangential flow filtration filter.

The salt solution can comprise a chloride, bromide, iodide, fluoride, sulfate, sulfite, carbonate, bicarbonate, phosphate, nitrate, nitrite, acetate, citrate, silicate and/or cyanide of an alkali metal, alkaline earth metal, aluminum and/or ammonium. The methods can also comprise removing salt by diafiltering the retentate fucan compositions against a low-ionic strength solution.

Methods for obtaining a high-molecular-weight fucans can comprise:
  providing a centrifuge container can comprise a bottom end and a top end and a permeable barrier therebetween, the permeable barrier can comprise a gradient material therebetween;
  placing a starting fucan compositions having a broad molecular weight distribution comprising a desired high-molecular-weight fucans segment in the centrifuge container and above the permeable barrier; and
  centrifuging the centrifuge container for a period of time sufficient to produce a precipitate consisting essentially of the desired high-molecular-weight fucans.

The methods further can comprise collecting the desired high-molecular-weight fucans from the centrifuge container. The permeable barrier can comprise a single segment of gradient material. The permeable barrier can comprise a plurality of segments of gradient material. The gradient material can comprise at least one of sucrose, polysucrose, glycerol, sorbitol, CsCl, $Cs_2SO_4$, KBr, diatrizoate, Nycodenz® and iodixanol. The centrifugal force can be between about 10,000 gravities to about 1,000,000 gravities. The centrifugal force can be between 60,000 gravities to about 500,000 gravities.

Methods for obtaining a high-molecular-weight fucans can comprise:
  providing a centrifuge container can comprise a bottom end and a top end;
  placing a starting fucan compositions in a starting solution, having a broad molecular weight distribution comprising a desired high-molecular-weight fucans segment in the centrifuge container; and
  centrifuging the centrifuge container for a period of time sufficient to produce a precipitate consisting essentially of the desired high-molecular-weight fucans.

The methods further can comprise collecting the desired high-molecular-weight fucans as a precipitate from the centrifuge container. The centrifugal force can be between about 60,000 gravities to about 1,000,000 gravities. The centrifugal force can be between 200,000 gravities to about 500,000 gravities.

Methods for obtaining a high-molecular-weight fucans can comprise:
  subjecting a starting fucan compositions having a broad molecular weight distribution comprising a desired high-molecular-weight fucans segment to gel electrophoresis wherein the starting fucan compositions can be displaced according to mass-to-charge ratio across an electrophoresis gel;
  selecting a portion of the electrophoresis gel consisting essentially of the desired high-molecular-weight fucans; and
  extracting the desired high-molecular-weight fucans from the selected portion of the electrophoresis gel.

The subjecting the starting fucan compositions to gel electrophoresis can comprise applying a potential difference across the electrophoresis gel can be between about 10 Volt/cm and 200 Volt/cm. The electrophoresis gel can comprise at least one of agarose, polyacrylamide, polydimethylacrylamide and starch. The electrophoresis gel further can comprise at least one of tris-acetate EDTA, tris-borate EDTA and phosphate buffered saline. Extracting the desired high-molecular-weight fucans from the selected portion of the electrophoresis gel can comprise agitating the selected portion of the electrophoresis gel in a solvent. The solvent can comprise at least one of water, methanol, ethanol and isopropanol.

Methods for obtaining a high-molecular-weight fucans can comprise:
  providing a starting fucan compositions having a broad molecular weight distribution comprising a desired high-molecular-weight fucans segment, and an ion exchange macroporous resin; and
  subjecting the starting fucan compositions to ion exchange with the ion exchange macroporous resin to obtain an ion exchange treated fucan compositions consisting essentially of the desired high-molecular-weight fucans.

The methods further can comprise collecting the desired high-molecular-weight fucans from the ion exchange treated fucan compositions. Providing the starting fucan compositions further can comprise desalting the starting fucan compositions before subjecting the starting fucan compositions to ion exchange. A mass ratio of the starting fucan composition:ion exchange macroporous resin can be between about 1:100 and about 10:1. The mass ratio can be between about 1:10 and about 5:1. The starting fucan compositions can be subjected to ion exchange for a period of can be between about 5 minutes and about 100 hours. The ion exchange macroporous resin can comprise at least one of an anion exchange macroporous resin and a mixed charge macroporous resin. The anion exchange macroporous resin can be a strong base macroporous resin. The strong base macroporous resin can comprise quaternary amine groups. The anion exchange macroporous resin can be a weak base macroporous resin. The weak base macroporous resin can comprise at least one of primary, secondary or tertiary amine groups. The ion exchange macroporous resin can comprise at least one of styrene, agarose, dextran, acrylate, methacrylate, methyl methacrylate, butyl methacrylate, divinylbenzene, cellulose, silica, and ceramic. The ion exchange macroporous resin has a pore size of can be between about 5 nm and about 1000 nm, about 10 nm and about 100 nm, or about 15 nm and about 50 nm. The ion exchange macroporous resin can have an exclusion limit of can be between about 50 kDa and about 50,000 kDa, about 1,000 kDa and about 9,000 kDa, or about 100 kDa and about 1,000 kDa. The starting fucan compositions can be subjected to anion-exchange for a period of can be between about 5 minutes and about 100 hours or between about 1 hour and about 30 hours.

Methods for obtaining a high-molecular-weight fucans can comprise:
  providing a starting fucan compositions with a broad molecular weight distribution comprising a desired high-molecular-weight fucans segment in a starting solution, and a gel media;
  subjecting the starting solution to preparative gel permeation chromatography, wherein the starting fucan compositions can be displaced from a first input end to a second output end across the gel media according to molecular weight; and
  collecting from the second output end at least one aliquot consisting essentially of the desired high-molecular-weight fucans segment.

The methods further can comprise collecting multiple aliquots and combining the aliquots. The gel media can be contained in a column. The gel media can comprise at least one of polyhydroxymethacrylate, sulfonated styrene-divinylbenzene, silica, a hydrophilic bonded phase or polymer, polystyrene, divinylbenzene, methacrylate, methyl methacrylate, butyl methacrylate, cellulose, ceramic, agarose and dextran. The gel media has a pore size of can be between about 3 nm and about 3000 nm, 3 nm and about 3000 nm, about 5 nm and about 10,000 nm, about 10 nm and about 100 nm, about 50 nm and about 500 nm, about 200 nm and about 2,000 nm, or about 500 nm and about 5,000 nm. The gel media has an exclusion limit of can be between about 100 Da and about 100,000 kDa, about 100 kDa and about 30,000 kDa, about 1,000 kDa and about 100,000 kDa, about 1,000 kDa and about 10,000 kDa, or about 5,000 kDa and about 50,000 kDa.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

Figure 1:
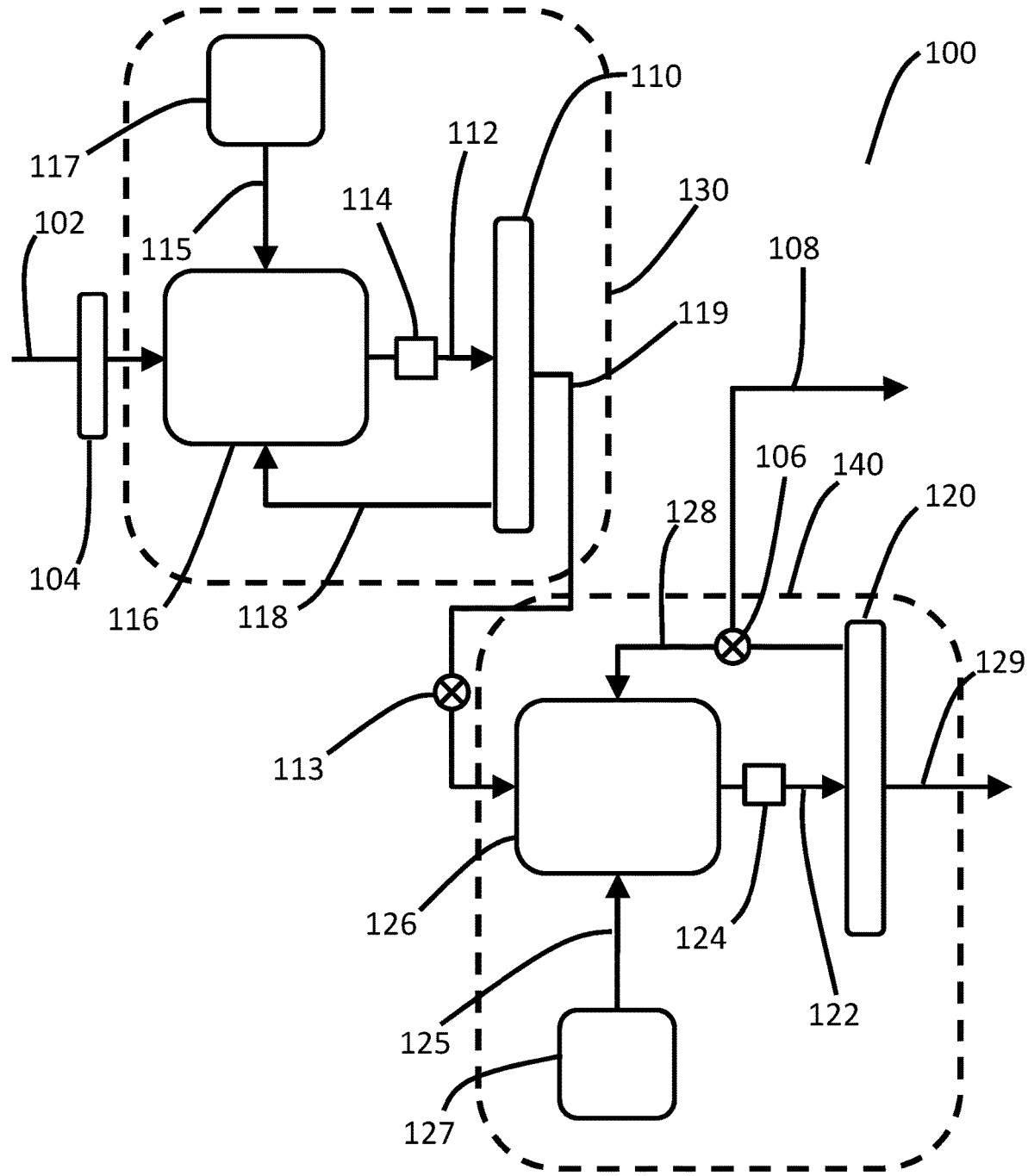
FIG. 1 schematically depicts an exemplary two-filter system for the segmentation of a starting fucan composition on the basis of molecular weight using sequential tangential flow filtration, the starting fucan having a broad molecular weight distribution.

The drawings present exemplary embodiments of the present disclosure. The drawings are not necessarily to scale and certain features may be exaggerated or otherwise represented in a manner to help illustrate and explain the present systems, methods, etc. Actual embodiments of the systems, methods, etc., herein may include further features or steps not shown in the drawings. The exemplifications set out herein illustrate embodiments of the systems, methods, etc., in one or more forms, and such exemplifications are not to be construed as limiting the scope of the disclosure in any manner. The embodiments herein are not exhaustive and do not limit the disclosure to the precise form disclosed, for example in the following detailed description.

DETAILED DESCRIPTION

The current compositions, systems, methods, etc., presented herein comprise high-molecular-weight fucans. The present compositions can be effective for medical treatments, post-surgical treatments, disease inhibition, etc. In some embodiments, the fucan is fucoidan. The present high-molecular-weight fucans can themselves be, or can be included on or in, medical devices, medical materials, combination products or in pharmaceutically acceptable, therapeutically and/or medically effective compositions.

The following paragraphs turn to a brief discussion of some of the methodologies that can be used to create the high-molecular-weight fucans and compositions herein from starting fucans and compositions via various methods that can be performed using any suitable reaction mixture such as solutions, suspensions, solids, gels or other modalities depending on the chosen method(s).

Compositions

The current compositions, systems, etc., presented herein provide, in certain embodiments, fucans and medically acceptable high-molecular-weight fucans and compositions comprising therapeutically effective amounts of high-molecular-weight fucans for the treatment of fibrous adhesions, such as surgical adhesions, arthritis, psoriasis or other diseases as desired.

The high-molecular-weight fucans presented herein may be used for a plurality of applications, including the inhibition, prevention, removal, reduction, or other treatment of fibrous adhesions and other targets and other diseases and/or conditions. Treatment includes that the high-molecular-weight fucans reduce or prevent the development of a target disease or other condition, such as reducing or preventing the formation of fibrous adhesions at a target site, formation of fibrous adhesions at a target site, which is typically a selected target site identified by a surgeon or other practitioner as comprising or reasonably susceptible to having fibrous adhesions (or other diseases or conditions), and also includes elimination of existing diseases or other conditions, including for example the elimination of already-existing fibrous adhesions. For such inhibition, prevention, removal, reduction, or other treatment, the high-molecular-weight fucan is typically provided in a medically acceptable medical device, combination product, or pharmaceutically effective composition that contains additional components such as binders, adjuvants, excipients, etc., as well as, if desired, additional medically active substances such as secondary drugs that are contained within the composition but not attached to the fucan, and/or that can be attached to the fucan.

The molecular weight distribution of the high-molecular-weight fucans may be measured using any desired, appropriate measurement system. Different systems can yield different readings or results from different compositions having essentially the same make-up, or even from the same batch when measured differently. One suitable measurement system is an aqueous gel permeation chromatography set up consisting essentially of one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C., a refractive index detector at about 30° C., 0.1M sodium nitrate mobile phase run at 0.6 mL/min, and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa. The peak molecular weight standard curve may further comprise a dextran standard with a peak molecular weight between 3 kDa and 5 kDa.

The high-molecular-weight fucans herein can have a weight average molecular weight over 100 kDa and comprise about 50% w/w or more of their molecular weight distribution above 100 kDa. Such high-molecular-weight fucans show greater efficacy in the inhibition, prevention, removal, reduction, and/or other treatment of fibrous adhesions than fucans with weight average molecular weight below 100 kDa and comprising less than about 50% of their molecular weight distribution above 100 kDa at the same dose. High-molecular-weight fucans with weight average molecular weight above 300 kDa, comprising about 70% or more of their molecular weight distribution above 100 kDa show even greater efficacy in the inhibition, prevention, removal, reduction, and/or other treatment of fibrous adhesions at the same dose.

In some embodiments, high-molecular-weight fucans herein are configured for use in inhibition, prevention, removal, reduction, or other treatment of fibrous adhesions that result in greater than about 65%, 70%, 80%, 90%, 95%, or 99% efficacious prevention, inhibition or other treatment of post-surgical adhesions. Such high-molecular-weight fucans can also be configured for such treatment of other targets.

The high-molecular-weight fucans herein may comprise a molecular weight distribution in which more than about 60%, 70%, 75%, 80%, 90%, 95 or 99% w/w of the fucan has a molecular weight above 100 kDa.

In other embodiments, the high-molecular-weight fucans herein may comprise a weight average molecular weight between about 100 kDa and 10,000 kDa, between about 140 kDa or 200 kDa and 9,000 kDa, between about 350 kDa or 370 kDa and 8,000 kDa, between about 450 kDa and 7,000 kDa, between about 580 kDa and 5,300 kDa or 6,000 kDa, between about 580 kDa or 590 kDa and 5,500 kDa, between about 400 kDa and 2,800 kDa or between about 800 kDa or 860 kDa and about 2,000 kDa for example about 850 kDa, about 930 kDa, about 1,100 kDa, about 1,200 kDa, about 1,300 kDa, about 1,600 kDa and about 1,800 kDa.

In yet other embodiments, the high-molecular-weight fucans herein may comprise a peak molecular weight between about 60 kDa or 70 kDa and 7,000 kDa, between about 100 kDa or 140 kDa and 6000 kDa, between about 200 kDa or 230 kDa and 5000 kDa, between about 250 kDa and 4000 kDa, between about 350 kDa and 3000 kDa, between about 500 kDa and 2000 kDa, or between about 400 kDa and about 1000 kDa, for example, about 450 kDa, 500 kDa, 550 kDa, 600 kDa, 650 kDa, 700 kDa and 750 kDa.

In yet other embodiments, the high-molecular-weight fucans herein may comprise a number average molecular weight between about 50 kDa and 3,000 kDa, between about 100 kDa and 2,000 kDa, between about 200 kDa and 1,500 kDa, between about 300 kDa and 2,000 kDa, between about 400 kDa and 1,000 kDa, or between about 250 kDa and about 600 kDa, for example, about 300 kDa, 350 kDa, 400 kDa, 450 kDa, 500 kDa and 550 kDa.

In yet other embodiments, the high-molecular-weight fucans herein may comprise a molecular weight distribution in which more than about 55% w/w or 60% w/w of the fucan may have a molecular weight above 200 kDa, or more than about 70% w/w or 71% w/w of the fucan may have a molecular weight above 200 kDa. In yet other embodiments, the high-molecular-weight fucans herein may comprise a molecular weight distribution in which more than 22% w/w or 30% w/w of the fucan may have a molecular weight above 500 kDa, or more than 50% w/w or 54% w/w of the fucan may have a molecular weight above 500 kDa.

In yet other embodiments, the high-molecular-weight fucans herein may comprise a molecular weight distribution in which less than about 10% w/w of the fucan has a molecular weight below 50 kDa, or less than about 5% w/w of the fucan has a molecular weight below 50 kDa, or less than about 2% w/w of the fucan has a molecular weight below 50 kDa.

In yet other embodiments, the high-molecular-weight fucans herein may comprise a molecular weight distribution in which less than about 5% w/w of the fucan has a molecular weight below 10 kDa, or less than about 2% w/w of the fucan has a molecular weight below 10 kDa.

In yet other embodiments, the high-molecular-weight fucans herein may comprise a molecular weight distribution in which less than about 5% w/w of the fucan has a molecular weight below 5 kDa, or less than about 2% w/w of the fucan has a molecular weight below 5 kDa.

In yet another aspect, the high-molecular-weight fucans herein may comprise a molecular weight distribution in which between 61% w/w and 80% w/w or 85% w/w of the fucan has a molecular weight between 200 kDa and 1600 kDa. More particularly, more than 70% w/w of the fucan may have a molecular weight above 200 kDa, and more than 30% of the fucan may have a molecular weight above 500 kDa.

In yet another aspect, the high-molecular-weight fucans herein may comprise a molecular weight distribution in which more than about 20% w/w, 40% w/w or 60% w/w of the fucan has a molecular weight above 1600 kDa. More particularly, more than about 70% w/w of the fucan may have a molecular weight above 200 kDa, or more than about 80% w/w of the fucan may have a molecular weight above 200 kDa.

The high-molecular-weight fucans herein may have a sulfation level of between about 14% w/w and 70% w/w, between about 20% w/w and 60% w/w, between about 30% w/w and 55% w/w, or between about 32% w/w or 35% w/w and 52% w/w.

The high-molecular-weight fucans herein may have a molar ratio of total fucose:total sulfate of between 1:0.5 and 1:4, between about 1:0.8 and 1:3.5, between about 1:1 and 1:2.5, between about 1:1.2 and 1:2.0, or between about 1:1.5 and 1:3.

The high-molecular-weight fucans herein may have a molar ratio of total fucose and galactose:total sulfate of between about 1:0.5 and 1:4, between about 1:0.8 and 1:3.5, between about 1:1 and 1:2.5, between about 1:1.2 and 1:2.0, or between about 1:1.5 and 1:3.

The high-molecular-weight fucans herein may have a total carbohydrate content of between 27% w/w and 80% w/w, between about 30% w/w and 70% w/w, between about 40% w/w and 90% w/w, or between about 50% w/w and 96% w/w.

The high-molecular-weight fucans herein may have a fucose content as a percentage of total carbohydrate of between about 30% w/w and 100% w/w, between about 40% w/w and 95% w/w, between about 50% w/w and 90% w/w, between about 80% w/w and 100% w/w, or between about 90% w/w and 100% w/w.

The high-molecular-weight fucans herein may have a galactose content as a percentage of total carbohydrate of between about 0% w/w and 60% w/w, between about 3% w/w and 30% w/w, between about 2% w/w and 20% w/w or between about 5% w/w and 10% w/w.

The high-molecular-weight fucans herein may have a glucuronic acid content as a percentage of total carbohydrate content between about 0% w/w and 10% w/w, a mannose content as a percentage of total carbohydrate content between about 0% w/w and 7% w/w, a rhamnose content as a percentage of total carbohydrate content between 0% w/w and 4% w/w, and a xylose content as a percentage of total carbohydrate content between 0% w/w and 20% w/w. The high-molecular-weight fucans herein may have a total of glucuronic acid, mannose, rhamnose, glucose and xylose content as a percentage of the total carbohydrate content below about 30% w/w or below about 12% w/w.

In some embodiments, the high-molecular-weight fucans herein, when dissolved at a concentration of about 50 mg/mL in water, have a viscosity of between about 4 cP and about 50 cP, between about 5 cP and about 40 cP, between about 10 cP and about 30 cP, about 15 cP, about 20 cP and about 25 cP. In certain embodiments, the high-molecular-weight fucans herein, when dissolved in water at 1 mg/mL through 100 mg/mL form a solution that is one of clear and colorless, clear and light yellow or clear and light brown.

In certain embodiments, the high-molecular-weight fucans herein can have an acetyl content of less than about 5% w/w, less than about 2% w/w, and about 0% w/w. In some embodiments, the high-molecular-weight fucans herein comprise substantially 0% w/w acetyl content when measured by 2D $^1$H-$^{13}$C heteronuclear multiple quantum coherence at 70° C. with solvent signal suppression on a 600

MHz spectrometer equipped with 5-mm cold probe, in the range from 10-30 ppm in the carbon dimension, in 8 increments of 256-512 scans each.

Methods

Methods, systems, etc., are presented for obtaining high-molecular-weight fucans obtained from a starting fucan composition, such as a feedstock fucan composition, having a broad molecular weight distribution (a broad molecular weight distribution starting fucan) that encompasses and extends beyond the desired high-molecular-weight segment, the desired high-molecular-weight segment being a portion of the broad molecular weight distribution wherein a quantity of the broad molecular weight distribution at the low molecular weight end has been eliminated, suppressed or otherwise attenuated. At least one of these methods may be used in the preparation of high-molecular-weight fucans, for example, comprising more than about 60%, 70%, 80%, 90% or 95% w/w of their molecular weight distribution above 100 kDa. In some embodiments, the current disclosure presents high-molecular-weight fucans that are suitable for medical and surgical applications, for example, the prevention of surgical adhesions.

Tangential Flow Filtration

Some of the methods discussed herein utilize tangential flow filtration (TFF). Consistent with typical identification of tangential flow filtration (TFF) filters, the nominal molecular weight cut-off (MWCO) value for a given TFF filter will selectively retain on its retentate side a solution containing molecules that did not cross the filter barrier and thus generally have molecular weights and/or sizes greater than the molecular weight of molecules that do cross/permeate the barrier to the permeate side. Thus, molecular weight cut-off values for TFF filters are typically not absolute for any given polymer or nominal cut-off value: a given TFF filter will pass or retain some molecules both above and below the nominal molecular weight cut-off. The actual cut-off/selectivity values and effects of a nominal TFF filter for a particular polymer can be routinely determined for the particular polymer.

A number of factors can affect the permeation behavior of the TFF filters. These factors may be dependent on the TFF filters themselves or dependent on an attribute of the target polymers, for example the folding behavior and folded structure of the target polymer can affect the behavior of the target polymer in crossing/not-crossing the TFF filter's MWCO barrier. Regarding the TFF filters themselves, as is known, a number of factors can affect the permeation behavior of the TFF filters. For example, manufacturing methods can cause a variety of hole sizes within the specific TFF filter, which variety can include holes both larger and smaller than the nominal MWCO. Thus, a TFF filter having a nominal molecular weight cut-off value will substantially pass/retain molecules at the nominal molecular weight cut-off value, but can also pass/retain some molecules below and/or above such value.

Gel Permeation Chromatography

Gel permeation chromatography was employed to evaluate the molecular weight distributions obtained for the experimental examples. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1M sodium nitrate run at 0.6 mL/min. The column compartment and detector were at 30° C. A Waters 2414 refractive index detector was used for detection.

Suitable GPC columns include GPC columns compatible with aqueous solvents, for example columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 μm particle size hydroxylated polymethacrylate-based gel, followed by a first 300 mm analytical GPC column with a 7.8 mm ID packed with 12 μm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 μm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

A molecular weight stated for a fucan/fucoidan polymer herein is a value of molecular weight about which there will always be a distribution of molecules of higher and lower molecular weights, increasing or decreasing in amount or percentage as the molecular weight increases or decreases away from the specified molecular weight. The distribution may, but is not required to, have a generally Gaussian or distorted Gaussian shape.

Results in the tables herein contain abbreviations used for certain characteristics of a molecular weight distribution. Gel permeation chromatography is denoted by GPC, peak retention time is denoted by PRT, peak molecular weight is denoted by PMW, weight average molecular weight is denoted by WAMW, number average molecular weight is denoted by NAMW, percentage distribution is denoted by % dist., molecular weight is denoted by MW, polydispersity index is denoted by PDI and molecular weight cutoff is denoted by MWCO.

The following paragraphs turn to a brief general discussion of some methodologies that can be used to create the high-molecular-weight fucans herein.

Sequential Tangential Flow Filtration Segmentation

A high-molecular-weight fucan may be obtained from a broad molecular weight distribution starting fucan composition by a sequential TFF segmentation method. The methods can comprise: providing a starting fucan composition comprising the desired molecular weight segment, for example a high-molecular-weight segment, the starting fucan composition having a starting broad molecular weight distribution; subjecting the starting fucan composition to tangential flow filtration across a first, higher MWCO tangential flow filtration filter having an average molecular weight cutoff within the starting molecular weight distribution; collecting from the first TFF filter a first permeate fucan composition comprising a reduced proportion of high-molecular-weight fucans compared with the starting fucan composition; subjecting the first permeate fucan composition to tangential flow filtration across a second, lower MWCO tangential flow filtration filter having a lower average molecular weight cutoff within the starting molecular weight distribution than the first TFF filter; and, collecting from the second TFF filter a fucan with the desired molecular weight segment in the retentate fucan composition.

The methods can comprise further steps as desired, for example pre-filtering the starting fucan composition through a pre-filter capable of filtering out particulates or moieties greater than a desired size, or other unwanted materials. Passing the starting fucan composition over the first TFF filter may comprise passing the starting fucan composition over the TFF filter while applying pressure to the starting fucan composition. Passing the permeate fucan composition of the first TFF filter over the second TFF filter may comprise passing the permeate fucan composition of the first TFF filter over the second TFF filter while applying pressure to the permeate fucan composition of the first TFF filter.

Passing the starting fucan composition over the first TFF filter may comprise recirculating the retentate fucan composition of the first TFF filter over the first TFF filter. Recirculating the retentate fucan composition of the first TFF filter over the first TFF filter may comprise diafiltering the retentate fucan composition over the first TFF filter. Recirculating the retentate fucan composition of the first TFF filter over the first TFF filter may comprise determining a weight average molecular weight of the permeate fucan composition of the first TFF filter. Recirculating the retentate fucan composition of the first TFF filter over the first TFF filter may comprise recirculating the retentate fucan composition of the first TFF filter over the first TFF filter until the weight average molecular weight of fucan in the permeate fucan composition of the first TFF filter has a predetermined desired value.

Passing a permeate fucan composition from the first TFF filter over the second TFF filter may comprise recirculating the permeate fucan composition over the second TFF filter. Recirculating the permeate fucan composition over the second TFF filter may comprise diafiltering the permeate fucan composition over the second TFF filter. Recirculating the permeate fucan composition over the second TFF filter may comprise determining a weight average molecular weight of a retentate fucan composition of the second TFF filter. Recirculating the permeate fucan composition over the second TFF filter may comprise recirculating the fucan over the second TFF filter until the weight average molecular weight of the retentate fucan composition of the second TFF filter has a predetermined desired value.

FIG. 1 shows schematically an exemplary molecular weight-based segmentation system (higher-to-lower) 100 comprising two different, higher and lower, molecular weight cut-off (MWCO) TFF filters, which in the embodiment shown are provided as higher molecular weight cut-off TFF filter 110 and lower molecular weight cut-off TFF filter 120; the TFF filters can be provided in any acceptable format, the current examples use cassettes. Higher molecular weight cut-off TFF filter 110 has a MWCO that is greater than the MWCO of lower molecular weight cut-off TFF filter 120. By way of example, higher molecular weight cut-off TFF filter 110 may have a MWCO of 30 kiloDalton (kDa), 50 kDa, 70 kDa, 100 kDa, 300 kDa and 1000 kDa, while the MWCO of lower molecular weight cut-off TFF filter 120 may be, for example, 5 kDa, 10 kDa, 30 kDa, 50 kDa and 100 kDa. By way of example, selecting a combination of a higher molecular weight cut-off TFF filter and a lower molecular weight cut-off TFF filter, molecular weight based segmentation system (higher-to-lower) 100 can be used to obtain a molecular weight segment between molecular weight cut-off TFF filters of 5-30 kDa, 10-30 kDa, 5-50 kDa, 10-50 kDa, 30-50 kDa, 10-70 kDa, 30-70 kDa, 50-70 kDa, 5-100 kDa, 10-100 kDa, 30-100 kDa, 50-100 kDa, 70-100 kDa, 5-300 kDa, 10-300 kDa, 30-300 kDa, 50-300 kDa, 70-300 kDa and 100-300 kDa. In some embodiments, the molecular weight segment can be a high-molecular-weight segment.

A starting fucan composition is supplied as a solution via input supply line 102 to higher MWCO subsystem fucan container 116. The starting fucan may be present in a suitable solvent at a concentration between 0.1% w/v and 30% w/v, such as between 1% w/v and 10% w/v, for example, at 5% w/v. The starting fucan in a suitable solvent may be pre-filtered through pre-filter 104 to remove undesired particulate matter. The solution containing the starting fucan composition may comprise further non-fucan components such as desired buffers, diluents, etc., as desired, for example for other fucan processing steps or downstream uses of the fucan. The gauge (effective hole size) of the pre-filter will typically be greater than the largest polymer molecules to be isolated by means of the molecular weight based segmentation system (higher-to-lower) 100.

Higher MWCO subsystem pump 114 pumps a solution containing the starting fucan composition to higher molecular weight cut-off TFF filter 110 of higher MWCO TFF subsystem 130 via higher MWCO TFF filter supply line 112. Higher molecular weight cut-off TFF filter 110 is typically supplied as a cassette designed to allow an input fluid to pass over its filter on its retentate side. The format of the molecular weight cutoff filter may be without limitation a plate and frame system; a spiral wound cartridge system; a hollow fiber system; a flow cell system; and centrifugal filter system. The permeate exits via higher MWCO subsystem permeate output line 119 and the treated input fluid, i.e., retentate fluid, leaves as retentate via higher MWCO subsystem retentate return line 118. Higher MWCO subsystem pump 114 provides a level of pressure over higher molecular weight cut-off TFF filter 110 between its retentate and permeate sides. In FIG. 1, the retentate fluid from higher molecular weight cut-off TFF filter 110 is returned to higher MWCO subsystem fucan container 116 via higher MWCO subsystem retentate return line 118, while permeate fluid is produced via higher MWCO subsystem permeate output line 119 for use outside of the higher MWCO TFF subsystem 130. While higher MWCO subsystem pump 114 recirculates the prefiltered fucan and retentate over higher molecular weight cut-off TFF filter 110, solvent may be supplied from higher MWCO subsystem solvent container 117 via higher MWCO subsystem solvent supply line 115, for example to replenish solvent lost via the permeate and/or to ensure that a predetermined number of diavolumes of input starting fucan and solvent are circulated over the higher molecular weight cut-off TFF filter 110.

Higher-to-lower MWCO inter-subsystem valve 113 may be shut off (closed) during the above processing, and permeate fluid from higher molecular weight cut-off TFF filter 110 of higher MWCO TFF subsystem 130 can be collected into a container (not shown) for storage or other use before being supplied to lower MWCO subsystem fucan container 126 of lower MWCO TFF subsystem 140. The starting fucan composition can be cycled as many times as desired through higher MWCO TFF subsystem 130.

The collected permeate from higher MWCO TFF subsystem 130 may then be supplied to lower MWCO subsystem fucan container 126 of lower MWCO TFF subsystem 140 via a higher MWCO subsystem permeate output line 119. In other embodiments, the collected permeate may be transferred in a container (not shown) to lower MWCO subsystem fucan container 126. In yet other embodiments of the system, the higher-to-lower MWCO inter-subsystem valve 113 may be maintained open and the permeate of higher molecular weight cut-off TFF filter 110 may be supplied via higher MWCO subsystem permeate output line 119 on a continuous basis to lower MWCO subsystem fucan container 126. The distribution of higher molecular weight molecules in the permeate of higher molecular weight cut-off TFF filter 110 is attenuated or suppressed compared with the distribution of higher molecular weight molecules in the starting fucan composition.

The permeate supplied to lower MWCO TFF subsystem 140 is filtered in a similar way over lower molecular weight cut-off TFF filter 120 as discussed above for higher molecular weight cut-off TFF filter 110. That is, after the permeate from higher MWCO TFF subsystem 130 is supplied to lower MWCO subsystem fucan container 126, lower MWCO subsystem pump 124 pumps it to lower molecular weight cut-off TFF filter 120 of lower MWCO TFF subsystem 140 via lower MWCO TFF filter supply line 122. Lower MWCO subsystem pump 124 maintains a level of pressure over lower molecular weight cut-off TFF filter 120 between its retentate and permeate sides. In FIG. 1, the retentate of lower molecular weight cut-off TFF filter 120 is returned to lower MWCO subsystem fucan container 126 via lower MWCO subsystem retentate return line 128, while a permeate is produced via lower MWCO subsystem permeate output line 129 for further use or discarding outside lower MWCO TFF subsystem 140. If the lower MWCO subsystem pump 124 recirculates the permeate from higher molecular weight cut-off TFF filter 110 and retentate from lower molecular weight cut-off TFF filter 120 to pass again over lower molecular weight cut-off TFF filter 120 (as with the higher molecular weight cut-off filtration filter, this recirculation can be repeated as often as desired), solvent may be supplied from lower MWCO subsystem solvent container 127 via lower MWCO subsystem solvent supply line 125 and lower MWCO subsystem fucan container 126 to replenish solvent lost via the lower MWCO subsystem permeate output line 129 and/or to ensure that a predetermined number of diavolumes of retentate of lower molecular weight cut-off TFF filter 120 and solvent are circulated over the lower molecular weight cut-off TFF filter 120.

During the tangential flow filtration operation of lower MWCO TFF subsystem 140, lower MWCO subsystem retentate-line valve 106 may be closed. When the permeate supplied to lower MWCO TFF subsystem 140 from higher MWCO TFF subsystem 130 has been filtered to a desired degree, lower MWCO subsystem retentate-line valve 106 is opened and the retentate of lower molecular weight cut-off TFF filter 120 is supplied via lower MWCO subsystem retentate output line 108. This provides a fucan with the desired molecular weight segment from a starting fucan composition, for example a high-molecular-weight fucan.

The output fucan has a desired molecular weight segment with a molecular weight distribution typically predominantly between the average molecular weight cut-off of the higher molecular weight cut-off TFF filter 110 and the average molecular weight cut-off of the lower molecular weight cut-off TFF filter 120. However, considering the width and complexity of the starting fucan molecular weight distribution and the variability of polymer behavior and TFF filters, the output polymer molecular weight distribution may not peak between the average molecular weight cut-off values of the two TFF filters. For example, excessively high or low folding of the fucan can result in selection of appropriately sized but unusually dense (or not) fucans in the desired molecular weight segment. Thus, in terms of the fucans present after the sequential TFF discussed herein, the output desired molecular weight segment consists essentially of a desired molecular weight segment derived from the original starting fucan composition that was supplied to molecular weight based isolation system (higher-to-lower) 100.

Further embodiments can comprise: providing a starting fucan composition comprising the desired molecular weight segment, for example a high-molecular-weight segment, the starting fucan composition having a starting molecular weight distribution; subjecting the starting fucan composition to tangential flow filtration across a first tangential flow filtration filter having an average molecular weight cutoff within the starting molecular weight distribution; collecting from the first TFF filter a first retentate fucan composition comprising a reduced proportion of low molecular weight fucans compared with the starting fucan composition; subjecting the first retentate fucan composition to tangential flow filtration across a second tangential flow filtration filter having a higher average molecular weight cutoff within the starting molecular weight distribution than the first TFF filter; and collecting from the second TFF filter a fucan with the desired molecular weight segment in the permeate fucan composition.

The methods may further comprise pre-filtering the starting fucan composition through a pre-filter capable of filtering out moieties greater than a desired size. Passing the starting fucan composition over the first TFF filter may comprise passing the starting fucan composition over the first TFF filter while applying pressure to the starting fucan composition. Passing the retentate fucan composition of the first MCWO filter over the second TFF filter may comprise passing the retentate fucan composition of the first TFF filter over the second TFF filter while applying pressure to the retentate fucan composition of the first TFF filter in the second TFF filter.

Passing the starting fucan composition over the first TFF filter may comprise recirculating the retentate fucan composition of the first TFF filter over the first TFF filter. Recirculating the retentate fucan composition of the first TFF filter over the first TFF filter may comprise diafiltering the retentate fucan composition over the first TFF filter.

Recirculating the retentate fucan composition of the first TFF filter over the first TFF filter may comprise determining a weight average molecular weight of the retentate fucan composition of the first TFF filter. Recirculating the retentate fucan composition of the first TFF filter over the first TFF filter may comprise recirculating the retentate fucan composition of the first TFF filter over the first TFF filter until the weight average molecular weight of fucan in the retentate fucan composition of the first TFF filter has a predetermined desired value.

Passing a retentate fucan composition from the first TFF filter over the second TFF filter may comprise recirculating the retentate fucan composition over the second TFF filter. Recirculating the retentate fucan composition over the second TFF filter may comprise diafiltering the retentate fucan composition over the second TFF filter. Recirculating the retentate fucan composition over the second TFF filter may comprise determining a weight average molecular weight of a permeate fucan composition of the second TFF filter. Recirculating the retentate fucan composition over the second TFF filter may comprise recirculating the retentate fucan composition over the second TFF filter until the weight average molecular weight of the permeate fucan composition of the second TFF filter has a predetermined desired value.

Figure 2:
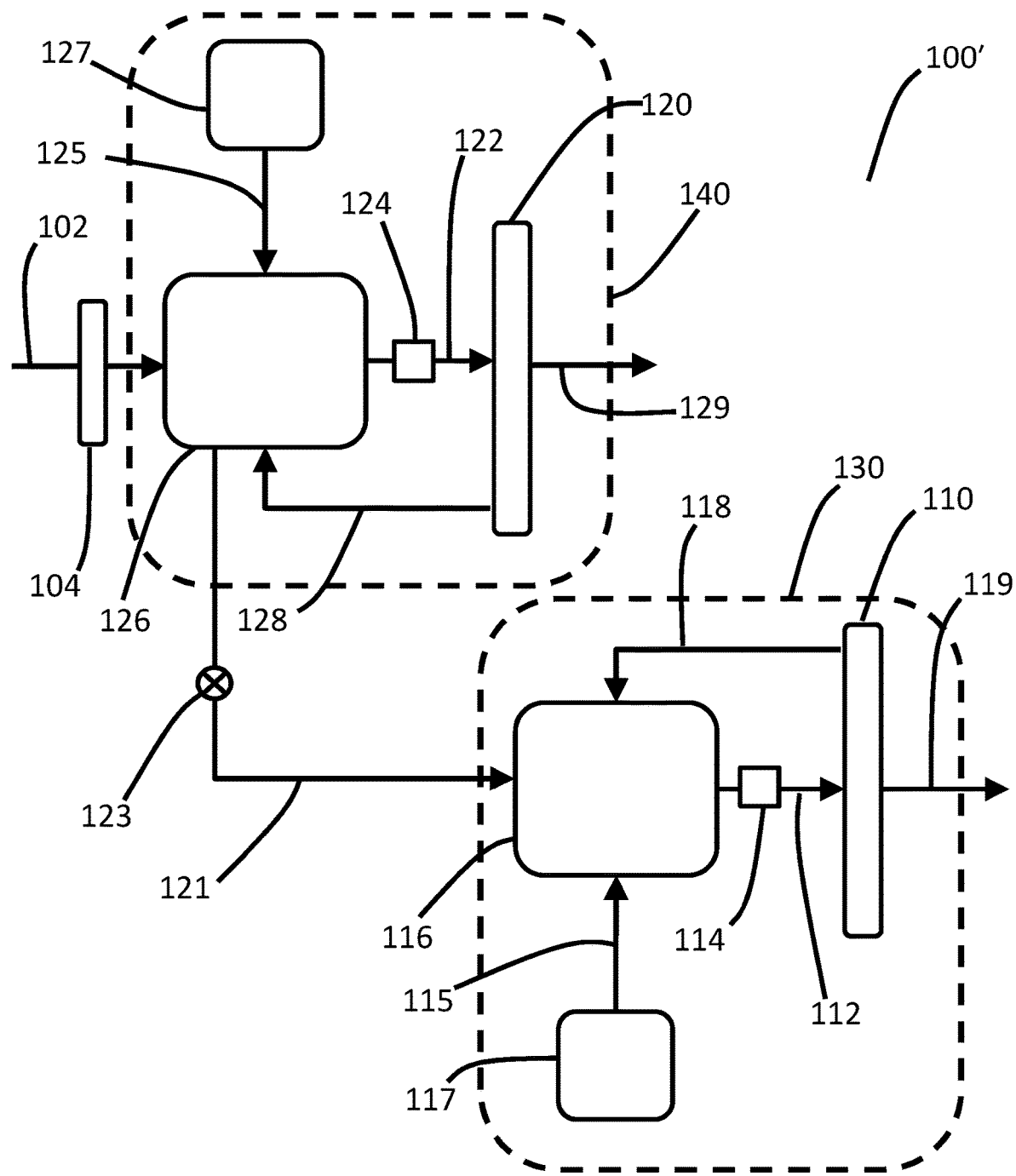
FIG. 2 schematically depicts an exemplary further embodiment of a two-filter system for the segmentation of a starting fucan composition on the basis of molecular weight using sequential tangential flow filtration, the starting fucan having a broad molecular weight distribution.

FIG. 2 shows a further embodiment of the methods, systems, etc., herein. In FIG. 2, subsystems 130 and 140 of FIG. 1 are reversed in terms of process order to form molecular weight-based segmentation system (lower-to-higher) 100'. As in the method discussed in FIG. 1, the starting fucan enters the system through input supply line 102 and is pre-filtered by pre-filter 104. However, in contrast to the method above in FIG. 1, the pre-filtered starting fucan is processed first in lower MWCO TFF subsystem 140 then in higher MWCO TFF subsystem 130. In lower MWCO TFF subsystem 140 the starting fucan composition is passed over lower molecular weight cut-off TFF filter 120, which is the TFF filter with the lower average MWCO value. In this embodiment, it is the retentate and not the permeate of lower molecular weight cut-off TFF filter 120 that exits lower MWCO TFF subsystem 140 on lower MWCO subsystem retentate output line 121. Such retentate exits through lower-to-higher MWCO inter-subsystem valve 123 to be supplied to higher MWCO subsystem fucan container 116 of higher MWCO TFF subsystem 130. The retentate is then pumped by higher MWCO subsystem pump 114 via higher MWCO TFF filter supply line 112 to pass over higher molecular weight cut-off TFF filter 110, which is the TFF filter with the higher MWCO.

Within lower MWCO TFF subsystem 140, lower MWCO subsystem pump 124 pumps the permeate from lower MWCO subsystem fucan container 126 to lower molecular weight cut-off TFF filter 120 via lower MWCO TFF filter supply line 122. In FIG. 2, the retentate of lower molecular weight cut-off TFF filter 120 is returned to lower MWCO subsystem fucan container 126 via lower MWCO subsystem retentate return line 128, while a permeate is produced via lower MWCO subsystem permeate output line 129 for further use or discarding outside lower MWCO TFF subsystem 140. If the retentate is recirculated to pass again over lower molecular weight cut-off TFF filter 120, solvent may be supplied from lower MWCO subsystem solvent container 127 via lower MWCO subsystem solvent supply line 125 and lower MWCO subsystem fucan container 126 to replenish solvent lost via the lower MWCO subsystem permeate output line 129 and/or to ensure that a predetermined number of diavolumes of retentate of lower molecular weight cut-off TFF filter 120 and solvent are circulated over the lower molecular weight cut-off TFF filter 120.

Lower-to-higher MWCO inter-subsystem valve 123 may be shut during the above processing, and the retentate of lower molecular weight cut-off TFF filter 120 of lower MWCO TFF subsystem 140 can be collected into a container (not shown) before being supplied to higher MWCO subsystem fucan container 116 of higher MWCO TFF subsystem 130. The collected retentate is supplied to higher MWCO subsystem fucan container 116 of higher MWCO TFF subsystem 130 via a physical lower MWCO subsystem retentate output line 121. In other embodiments, the collected retentate may be transferred in a container (not shown) to higher MWCO subsystem fucan container 116. In yet other embodiments, the lower-to-higher MWCO inter-subsystem valve 123 may be maintained open and the retentate of lower molecular weight cut-off TFF filter 120 supplied via lower MWCO subsystem retentate output line 121 on a continuous basis to higher MWCO subsystem fucan container 116. The distribution of lower molecular weight molecules in the retentate from lower molecular weight cut-off TFF filter 120 is attenuated or suppressed compared with the distribution of lower molecular weight molecules in the starting fucan.

As higher MWCO TFF subsystem 130 processes the retentate from lower molecular weight cut-off TFF filter 120 of lower MWCO TFF subsystem 140, the permeate of higher molecular weight cut-off TFF filter 110 is produced on higher MWCO subsystem permeate output line 119. While higher MWCO subsystem pump 114 recirculates the retentate fucan of lower MWCO TFF subsystem 140 over higher molecular weight cut-off TFF filter 110, solvent may be supplied from higher MWCO subsystem solvent container 117 via higher MWCO subsystem solvent supply line 115 to replenish solvent lost via the permeate and/or to ensure that a predetermined number of diavolumes of retentate fucan of lower MWCO TFF subsystem 140 and solvent are circulated over the higher molecular weight cut-off TFF filter 110.

In FIG. 2, the retentate fluid from higher molecular weight cut-off TFF filter 110 is returned to higher MWCO subsystem fucan container 116 via higher MWCO subsystem retentate return line 118, while permeate fluid is produced via higher MWCO subsystem permeate output line 119 for use outside of the higher MWCO TFF subsystem 130. In FIG. 2, the output fucan with the desired molecular weight segment produced through higher MWCO subsystem permeate output line 119 has a molecular weight distribution predominantly between the average molecular weight cut-off of the first higher molecular weight cut-off TFF filter 110 and the average molecular weight cut-off of the second lower molecular weight cut-off TFF filter 120. However, considering the width and complexity of the starting fucan molecular weight distribution and the variability of polymer behavior and TFF filters, the output polymer molecular weight distribution may not peak between the average molecular weight cut-off values of the two TFF filters. For example, excessively high or low folding of the fucan can result in selection of appropriately sized but unusually dense (or not) fucans in the desired molecular weight segment. Thus, in terms of the fucans present after the sequential TFF discussed herein, the output fucan consists essentially of a desired molecular weight segment of fucan derived from the original starting fucan composition that was supplied to molecular weight based segmentation system (lower-to-higher) 100'. This output fucan with a desired molecular weight segment can also be derived from the pre-filtered starting fucan composition created after prefiltering by pre-filter 104 and then supplied to lower MWCO TFF subsystem 140.

Cation Augmented Tangential Flow Filtration

A high-molecular-weight fucan may be obtained from a broad molecular weight distribution starting fucan by cation augmented TFF, the methods comprising: providing the starting fucan composition having low atomic weight cations and a molecular weight distribution comprising a desired high-molecular-weight segment; cation treating the starting fucan composition with a cationic additive having cations of greater molecular weight than the low atomic weight cations to replace the low atomic weight cations with additive cations; subjecting the cation-treated fucan composition to tangential flow filtration across a first tangential flow filtration filter having an average molecular weight cutoff based on a molecular weight distribution of the desired high-molecular-weight fucan segment to generate a first retentate fucan composition; subjecting the first retentate fucan composition to tangential flow filtration across a second lower MWCO tangential flow filtration filter having an average molecular weight cutoff based on a molecular weight distribution of the cationic additive to generate a second retentate fucan composition; subjecting the second retentate fucan composition to diafiltration with a salt solution to generate a third retentate fucan composition; subjecting the third fucan retentate composition to diafiltration across the same second tangential flow filtration filter with a low conductivity diafiltration solution to produce a fourth retentate fucan composition; and collecting the fourth retentate solution comprising the desired high-molecular-weight fucan.

The methods can comprise further steps as desired, for example pre-filtering the starting fucan composition through a pre-filter capable of filtering out particulates or moieties greater than a desired size, or other unwanted materials. Passing the starting fucan composition over the first TFF filter may comprise passing the starting fucan composition over the TFF filter while applying pressure to the starting fucan composition. Passing the retentate fucan composition of the first TFF filter over the second TFF filter may comprise passing the retentate fucan composition of the first TFF filter over the second TFF filter while applying pressure to the retentate fucan composition of the first TFF filter.

Subjecting the first retentate fucan composition to tangential flow filtration across the second tangential flow filtration filter and treating the second retentate fucan composition with a salt solution may be done simultaneously. Treating the second retentate fucan composition with a salt may comprise treating the second retentate fucan composition with a chloride, bromide, iodide, fluoride, sulfate, sulfite, carbonate, bicarbonate, phosphate, nitrate, nitrite, acetate, citrate, silicate and/or cyanide of an alkali metal, alkaline earth metal, aluminum and/or ammonium. Treating the first retentate fucan composition with a sodium salt may comprise treating the first retentate with sodium chloride.

Cation treating the starting fucan composition with a cationic additive may comprise treating the starting fucan with a cationic additive having cations of greater molecular weight than the low atomic weight cations within the starting fucan. The cationic additive may be a polycationic additive. Cation treating the starting fucan composition with a cationic additive may comprise treating the starting fucan with a zwitterionic additive having zwitterions of greater molecular weight than the low atomic weight cations within the starting fucan.

Subjecting the cation-treated fucan composition to tangential flow filtration across a first tangential flow filtration filter may comprise recirculating the cation-treated fucan composition over the first TFF filter. Recirculating the cation-treated fucan composition over the first TFF filter may comprise diafiltering the cation-treated fucan composition over the first TFF filter with a solution of the cationic additive. Recirculating the cation-treated fucan composition over the first TFF filter may comprise determining a weight average molecular weight of fucan in the cation-treated fucan composition. Recirculating the cation-treated fucan composition over the first TFF filter may comprise recirculating the cation-treated fucan composition over the first TFF filter until the weight average molecular weight of cation-treated fucan in the cation-treated fucan composition has a predetermined desired value, producing the first retentate fucan composition.

Subjecting the first retentate fucan composition to tangential flow filtration across a second lower MWCO tangential flow filtration filter may comprise recirculating the first retentate fucan composition over the second TFF filter. Recirculating the first retentate fucan composition over the second TFF filter may comprise diafiltering the first retentate fucan composition of the second TFF filter with a salt solution. Recirculating the first retentate fucan composition over the second TFF filter may comprise determining a weight average molecular weight of fucan in the first retentate fucan composition. Recirculating the first retentate fucan composition over the second TFF filter may comprise recirculating the first retentate fucan composition over the second TFF filter until the weight average molecular weight of fucan from the first retentate fucan composition has a predetermined desired value, producing the second retentate fucan composition.

Subjecting the second retentate fucan composition to diafiltration with a salt solution may comprise recirculating the second retentate fucan composition over the second TFF filter. Recirculating the second retentate fucan composition over the second TFF filter may comprise diafiltering the second retentate fucan composition of the first TFF filter with a salt solution comprising at least one of a chloride, bromide, iodide, fluoride, sulfate, sulfite, carbonate, bicarbonate, phosphate and nitrate of an alkali metal, alkaline earth metal, aluminum and ammonium, for example sodium chloride. Subjecting the third retentate fucan composition to tangential flow filtration across the second MWCO tangential flow filtration filter may comprise recirculating the third retentate fucan composition over the second TFF filter. Recirculating the third retentate fucan composition over the second TFF filter may comprise diafiltering the third retentate fucan composition of the second TFF filter with a low conductivity solution. The low conductivity solution may be deionized water.

Cation treating the starting fucan composition with a cationic additive may comprise treating the input fucan with at least one of choline, polyvinylpyrrolidone, taurine, polyamine, chitosan, histone, and collagen.

Figure 3:
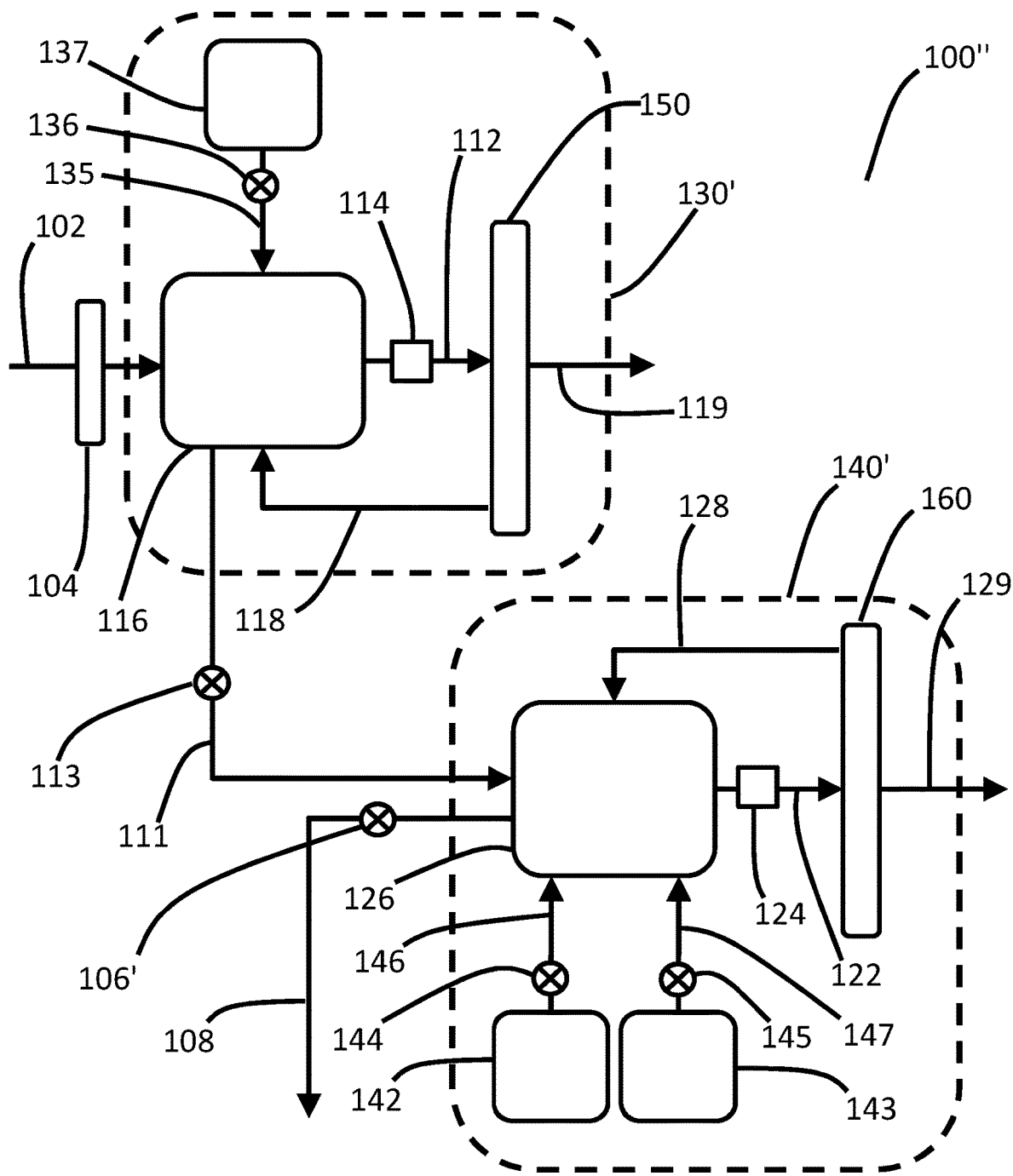
FIG. 3 schematically depicts an exemplary system for obtaining a desired high-molecular-weight fucan from a starting fucan composition using cation-augmented tangential flow filtration, the starting fucan having a broad molecular weight distribution.

FIG. 3 shows a schematic diagram of a cation-augmented TFF system (CATS) 100" for the separation of a fucan on the basis of molecular weight. CATS 100" employs a number of elements already discussed at the hand of FIG. 1 and FIG. 2. A solution containing the starting fucan composition is supplied via input supply line 102 to higher MWCO subsystem fucan container 116. The starting fucan composition in a suitable solvent may be pre-filtered through pre-filter 104 to remove undesired particulate matter. The solution containing the starting fucan composition may comprise further non-fucan components such as desired buffers, diluents, etc., as desired, for example for other fucan processing steps or downstream uses of the fucan. The gauge of the pre-filter will typically be greater than the largest polymer molecules to be separated by means of the CATS 100".

Cationic additive, for example choline, polyvinylpyrrolidone, polyaniline, may be added to the pre-filtered starting fucan composition in higher MWCO subsystem fucan container 116. Higher MWCO subsystem pump 114 pumps fucan to higher MWCO TFF filter 150 of higher MWCO TFF subsystem 130' via higher MWCO TFF filter supply line 112. Higher MWCO TFF filter 150 is typically supplied as a cassette designed to allow an input fluid supplied to it to pass over its filter on its retentate side, while allowing a permeate to exit via one output line and treated input fluid to leave as retentate via another output line. The format of the molecular weight cutoff filter may be without limitation a plate and frame system; a spiral wound cartridge system; a hollow fiber system; a flow cell system; and centrifugal filter system. For this embodiment, the cut off molecular weight of higher MWCO TFF filter 150 is chosen to separate a desired portion of the high-molecular-weight end of the cation-treated fucan obtained by treating the pre-filtered starting fucan with the cationic additive.

Higher MWCO subsystem pump 114 provides a level of pressure over higher MWCO TFF filter 150 between its retentate and permeate sides. In FIG. 3, the retentate of higher MWCO TFF filter 150 is returned to higher MWCO subsystem fucan container 116 via higher MWCO subsystem retentate return line 118, while permeate is produced via higher MWCO subsystem permeate output line 119 for use outside higher MWCO TFF subsystem 130' or to be discarded. While higher MWCO subsystem pump 114 recirculates the prefiltered starting fucan composition and retentate over higher MWCO TFF filter 150, cationic additive flush solution from cationic additive flush solution container 137 may be supplied via cationic additive flush solution supply line 135, for example to replenish solution lost via the permeate on higher MWCO subsystem permeate output line 119 and/or to ensure that a predetermined number of diavolumes of input starting fucan and cationic additive flush solution are circulated over the higher MWCO TFF filter 150. By controlling cationic additive flush solution valve 136, the cationic additive flush solution may be added in a pulse process. In other embodiments, the cationic additive flush solution may be added in a continuous mode. In other embodiments, the cationic additive flush solution may be added all at once. If choline has been chosen as cationic additive for the input starting fucan, then the cationic additive flush solution employed is a choline solution, for example a choline chloride solution. The number of diavolumes of retentate and choline flush solution to process over higher MWCO TFF filter 150 may be predetermined, four diavolumes being a generally useful number.

Higher-to-lower MWCO inter-subsystem valve 113 may be shut (closed) during the above processing, and retentate of higher MWCO TFF filter 150 of higher MWCO TFF subsystem 130' collected into a container (not shown) before being supplied to lower MWCO subsystem fucan container 126 of lower MWCO TFF subsystem 140'. The collected retentate may then be supplied to lower MWCO subsystem fucan container 116 of lower MWCO TFF subsystem 140' via higher MWCO subsystem retentate output line 111. In other embodiments, the collected retentate may be transferred in a container (not shown) to lower MWCO subsystem fucan container 126. In yet other embodiments of the system, the higher-to-lower MWCO inter-subsystem valve 113 may be maintained open and the retentate of higher MWCO TFF filter 150 may be supplied via higher MWCO subsystem retentate output line 111 on a continuous basis to lower MWCO subsystem fucan container 126. The distribution of lower molecular weight molecules in the retentate of higher MWCO TFF filter 150 is attenuated or suppressed compared with the distribution of lower molecular weight molecules in the starting fucan composition.

The lower MWCO TFF subsystem 140' removes the choline cations from the cation-treated fucan and restores sodium cations to the fucan, thereby returning the cation-treated fucan to about its original ionic components, but with a different desired high-molecular-weight distribution. During the processing of fucan solutions by lower MWCO TFF subsystem 140', lower MWCO subsystem output valve 106' controlling the lower MWCO subsystem retentate output line 108 from lower MWCO subsystem fucan container 126 may be closed. As lower MWCO TFF subsystem 140' processes the retentate from higher MWCO TFF filter 150 of higher MWCO TFF subsystem 130', the permeate of lower MWCO TFF filter 160 is produced on lower MWCO subsystem permeate output line 129 via which is employed elsewhere or is discarded.

While lower MWCO subsystem pump 114 recirculates the retentate of lower MWCO TFF subsystem 140' over lower MWCO TFF filter 160, a sodium salt solution, for example 2M NaCl solution, may be supplied from sodium salt solution container 142 via sodium salt solution supply line 146 by appropriate control of sodium salt solution control valve 144. For this method, the cut off molecular weight of lower MWCO TFF filter 160 is chosen to separate cationic additive released from the fucan by the sodium salt treatment. As the process of lower MWCO TFF subsystem 140' proceeds, the free choline chloride resulting from the replacement of the choline cations on the fucan with sodium cations from the NaCl transfers to the permeate of lower MWCO TFF filter 160 and leaves CATS 100" via lower MWCO subsystem permeate output line 129. The sodium salt solution may be used, for example to replenish solution lost via the permeate on lower MWCO subsystem permeate output line 129 and/or to ensure that a predetermined number of diavolumes of sodium salt solution and retentate from higher MWCO TFF subsystem 130' are circulated over the lower MWCO TFF filter 160. By controlling sodium salt solution control valve 144, the sodium salt solution may be added in a pulse process. In other embodiments, the sodium salt solution may be added in a continuous mode. When a suitable number of diavolumes of sodium salt solution and retentate have been circulated over lower MWCO TFF filter 160, sodium salt solution control valve 144 may be closed and low conductivity diafiltration solution valve 145 opened. The number of diavolumes of sodium salt solution to process over lower MWCO TFF filter 160 may be predetermined. Lower-MWCO-subsystem pump 124 provides a level of pressure over lower-MWCO TFF filter 160 between its retentate and permeate sides. In FIG. 3, the retentate of lower MWCO TFF filter 160 is returned to lower MWCO subsystem fucan container 126 via lower MWCO subsystem retentate return line 128, while permeate is produced via lower MWCO subsystem permeate output line 129 for use outside lower MWCO TFF subsystem 140' or to be discarded.

Low conductivity diafiltration solution valve 145 may be opened to allow low conductivity diafiltration solution from low conductivity diafiltration solution container 143 to enter lower MWCO subsystem fucan container 126 via low conductivity diafiltration solution supply line 147, the retentate and low conductivity diafiltration solution may be processed over lower MWCO TFF filter 160 to remove the free sodium salt generated during the sodium salt treatment of the retentate of lower MWCO TFF filter 160. The low conductivity diafiltration solution may be, for example, deionized water. To this end, the conductivity of permeate on lower MWCO subsystem permeate output line 129 may be measured to ensure it drops to a desired level, this serving as indication that the sodium salt has been removed to a suitable degree. The number of diavolumes of low conductivity diafiltration solution to process over lower MWCO TFF filter 160 may be predetermined. When the sodium salt has been suitably removed from the retentate of lower MWCO TFF filter 160, low conductivity diafiltration solution valve 145 maybe shut and lower MWCO subsystem retentate output line 108 opened to deliver the product of CATS 100" on lower MWCO subsystem retentate output line 108.

Centrifugal Precipitation

A high-molecular-weight fucan may be obtained from a broad distribution starting fucan by centrifugal precipitation.

Figure 4:
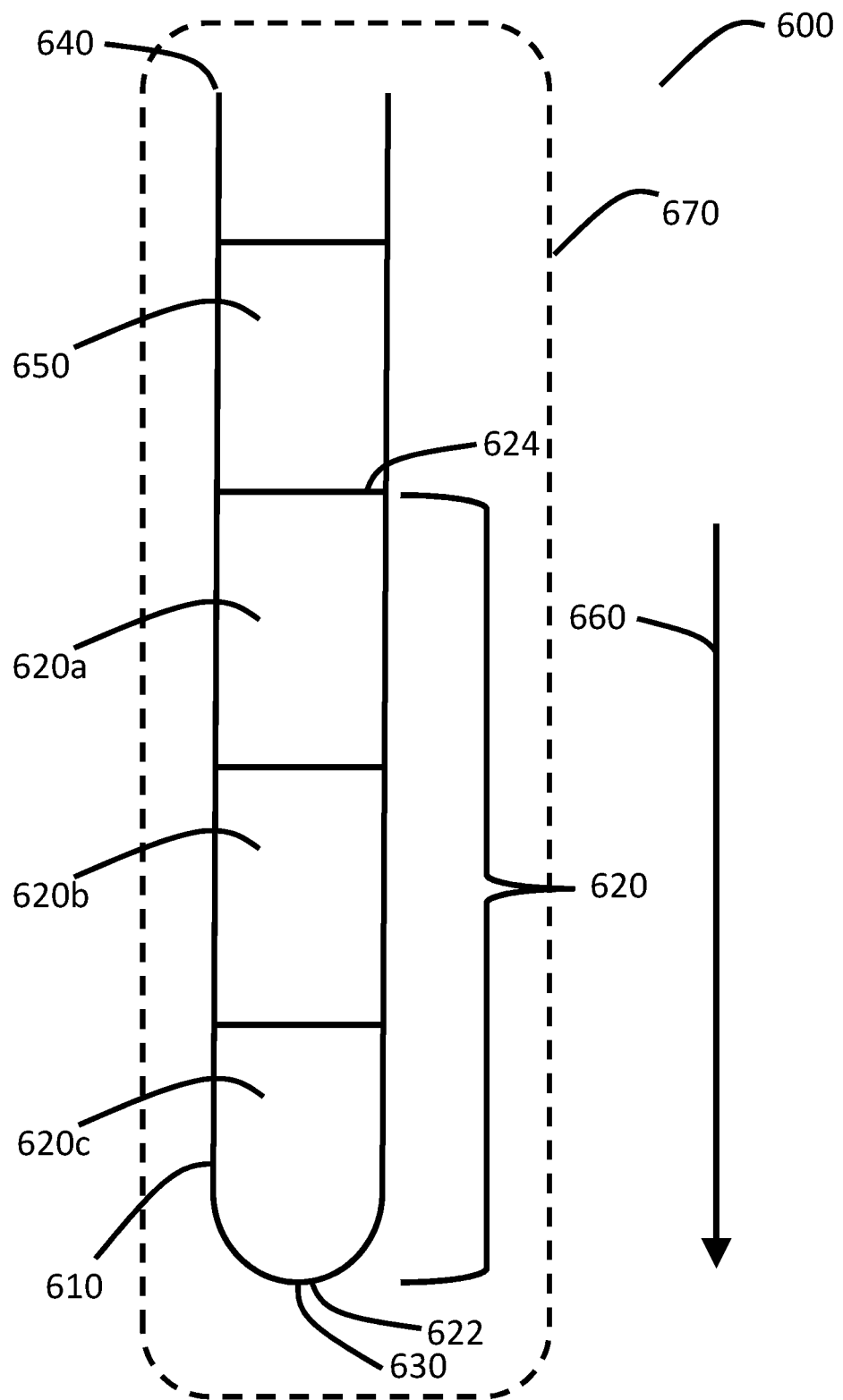
FIG. 4 schematically depicts an exemplary system for centrifugally precipitating a high-molecular-weight fucan from a starting fucan composition using a multi-segment barrier of gradient material, the starting fucan having a broad molecular weight distribution.

Turning to FIG. 4, a centrifugal precipitation system 600 for centrifugal precipitating a high-molecular-weight fucan from a starting fucan composition is shown. The system 600 comprises a centrifuge container 610 comprising a gradated permeable barrier 620. The permeable barrier may be gradated on the basis of density, with density decreasing from a first-bottom end 630 toward a second-top end 640 of the centrifuge container 610. The gradated permeable barrier 620 may be comprised of different materials of different densities. The gradated permeable barrier 620 may be comprised of solutions of different concentrations of one solute dissolved in a suitable solvent. Suitable solvents may be, for example without limitation, one of water and a water-alcohol solution. The solute, also known as "gradient material" may be for example without limitation one or more of glycerol, sorbitol, CsCl, $Cs_2SO_4$, KBr, diatrizoate, Nycodenz®, iodixanol and suitable saccharides, including (poly) sucrose. The gradated permeable barrier 620 may comprise a continuous gradient of decreasing gradient material concentration from the first-bottom end 630 to the second-top end 640 of the centrifuge container 610. In other embodiments, the gradated permeable barrier 620 may comprise a plurality of distinct gradations in density, for example gradated permeable barrier segments 620*a*, 620*b*, and 620*c*, as shown in FIG. 4. A solution containing the starting fucan composition, suitably pre-filtered through a pre-filter to remove particulate matter, is disposed to be the starting fucan composition 650 proximate the second-top end 640 of the centrifuge container 610 and in contact with the gradated permeable barrier 620. The pre-filter may be, for example without limitation, a 0.22 μm particulate filter.

In operation the centrifuge container is subjected to centrifugal force having a force component directed from the second-top end 640 to the first-bottom end 630 of the container as indicated by centrifugal force arrow 660 in FIG. 4. This may be achieved in a suitable centrifuge, schematically shown as centrifuge box 670 in FIG. 4 and adapted to accommodate the centrifuge container 610. Suitable centrifuges are well known in the art and will not be further discussed herein. The centrifugal force may be between about 1,000 gravities to about 1,000,000 gravities, for example between about 10,000 gravities to about 200,000 gravities, between about 60,000 gravities to about 500,000 gravities and between about 190,000 gravities to about 800,000 gravities.

Associated with the system of FIG. 4, the method for centrifugally precipitating a high-molecular-weight fucan from a starting fucan composition comprises establishing within the centrifuge container 610 a gradated permeable barrier 620 of a gradient material having a first-bottom gradated permeable barrier material end 622 in contact with a first-bottom end 630 of the centrifuge container 610; disposing in contact with an opposing second-top gradated permeable barrier material end 624 of the gradated permeable barrier 620 proximate a second-top end 640 of the centrifuge container 610 the starting fucan composition comprising a desired high-molecular-weight segment; subjecting the centrifuge container 610 to a centrifugal force 660 directed from the second-top end 640 to the first-bottom end 630 of the centrifuge container 610; and collecting precipitated high-molecular-weight fucan at the first-bottom end 630 of the centrifuge container 610. Disposing the starting fucan composition 650 in contact with the lowest density gradient material may comprise pre-filtering the starting fucan composition through a suitable pre-filter.

Establishing within the centrifuge container 610 a gradated permeable barrier 620 of a gradient material may comprise establishing a plurality of segments of gradient material, the density of the gradient material segments decreasing from the first-bottom end 630 of the centrifuge container 610 toward the second-top end 640 of the centrifuge container 610. Establishing within the centrifuge container 610 a gradated permeable barrier 620 of a gradient material may comprise establishing within the centrifuge container 610 a gradated permeable barrier 620 of a saccharide. Establishing within the centrifuge container 610 a gradated permeable barrier 620 of a gradient material may comprise establishing within the centrifuge container 610 a gradated permeable barrier 620 of sucrose. Establishing within the centrifuge container 610 a gradated permeable barrier 620 of a gradient material may comprise establishing within the centrifuge container 610 a gradated permeable barrier 620 of at least one of glycerol, sorbitol, CsCl, $Cs_2SO_4$, KBr, diatrizoate, Nycodenz® and iodixanol. Establishing within the centrifuge container 610 a gradated permeable barrier 620 of a gradient material may comprise establishing within the centrifuge container 610 a gradated permeable barrier 620 of a gradient material dissolved in a solvent. Establishing within the centrifuge container 610 a gradated permeable barrier 620 of a gradient material may comprise establishing within the centrifuge container 610 a gradated permeable barrier 620 of a gradient material dissolved in one of water and a water-alcohol solution.

Figure 5:
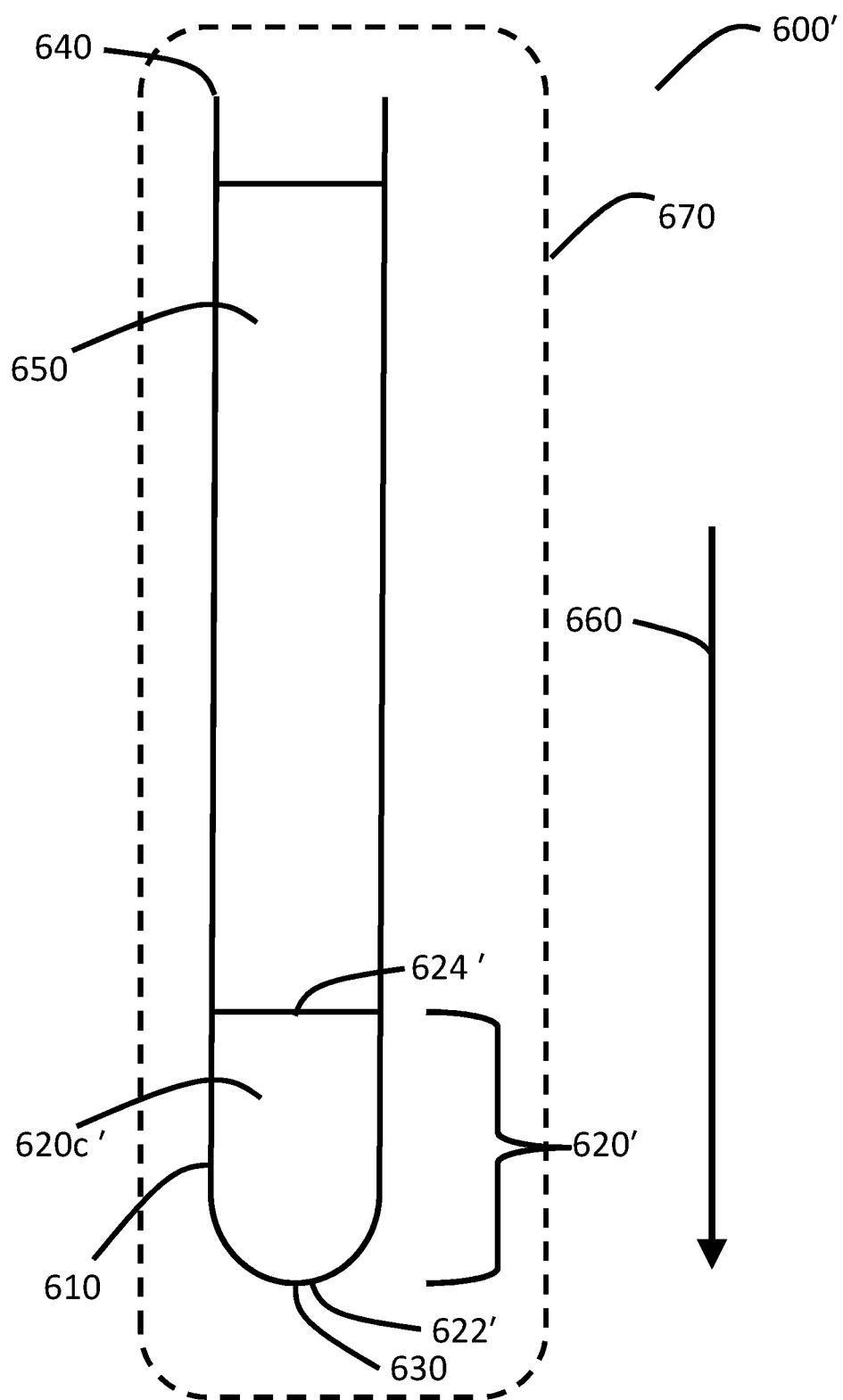
FIG. 5 schematically depicts an exemplary system for centrifugally precipitating a high-molecular-weight fucan from a starting fucan composition using a single segment barrier, the starting fucan having a broad molecular weight distribution.

FIG. 5 shows another embodiment of a centrifugal precipitation system 600' for centrifugally precipitating a high-molecular-weight fucan from a starting fucan composition. Employing similar numbering as in FIG. 4, this embodiment uses a permeable barrier 620' having a single barrier segment 620*c*' of gradient material of which a first-bottom permeable barrier material end 622' is in contact with a first-bottom end 630 of the centrifuge container 610. In this embodiment, the starting fucan composition is directly in contact with an opposing second-top permeable barrier material end 624' of the permeable barrier 620'. In this embodiment the method comprises subjecting the centrifuge container 610 to a centrifugal force 660 directed from the second-top end 640 to the first-bottom end 630 of the centrifuge container 610 and collecting precipitated high-molecular-weight fucan at the first-bottom end 630 of the centrifuge container 610. Disposing the starting fucan composition 650 in contact with the lowest density gradient material may comprise pre-filtering the starting fucan composition through a suitable pre-filter.

Other embodiments require no barrier to be employed and the container with starting fucan composition is centrifuged to subject the centrifuge container 610 to a centrifugal force 660 directed from the second-top end 640 to the first-bottom end 630 of the centrifuge container 610 and collecting precipitated high-molecular-weight fucan at the first-bottom end 630 of the centrifuge container 610.

Gel Electrophoresis-Extraction

A high-molecular-weight fucan may be obtained from a broad molecular weight distribution starting fucan by gel electrophoresis-extraction. The methods can comprise: subjecting the starting fucan composition comprising a desired high-molecular-weight-segment to gel electrophoresis wherein the starting fucan composition is displaced according to mass to charge ratio by the action of an applied electric potential difference; selecting a portion of the electrophoresis gel on the basis of the potential difference and the desired high-molecular-weight fucan; and extracting the desired high-molecular-weight fucan from the selected gel portion.

Subjecting the starting fucan composition to gel electrophoresis may comprise first pre-filtering the starting fucan composition in solution through a pre-filter to remove undesired particulate matter. Subjecting the starting fucan composition to gel electrophoresis may comprise preparing the starting fucan composition in a solution at a concentration of between 0.1% w/v and 30% w/v. Extracting the desired high-molecular-weight fucan may comprise extracting the desired high-molecular-weight fucan from a gel portion that extends along the a direction of the potential difference for a distance of between 0.1 mm and 1000 mm. Extracting the desired high-molecular-weight fucan may comprise extracting the gel portion using one of water, methanol, ethanol, isopropanol, a water/alcohol mix and a salt solution.

Subjecting the starting fucan composition to gel electrophoresis may comprise displacing the starting fucan composition in solution for a predetermined amount of time. Subjecting the starting fucan composition to gel electrophoresis across the electrophoresis gel may comprise displacing the starting fucan composition across the electrophoresis gel while the gel is immersed in a buffer solution. Subjecting the starting fucan composition to gel electrophoresis across the electrophoresis gel may comprise preparing the gel from a gel material and the buffer solution. Preparing the gel from the gel material and the buffer solution may comprise preparing the gel from the buffer and one of agarose, polyacrylamide, polydimethylacrylamide and starch. Preparing the gel from the gel material and the buffer solution may comprise preparing the gel from one of tris-acetate EDTA, tris-borate EDTA and phosphate buffered saline together with a gel material. Displacing the starting fucan composition under the action of an applied electric potential difference may comprise displacing the starting fucan composition under the action of an applied electric field strength of between about 1 Volt/cm and about 500 Volt/cm, for example between about 5 Volt/cm to about 50 Volt/cm, between about 10 Volt/cm to about 200 Volt/cm and between about 50 Volt/cm to about 300 Volt/cm.

Figure 6:
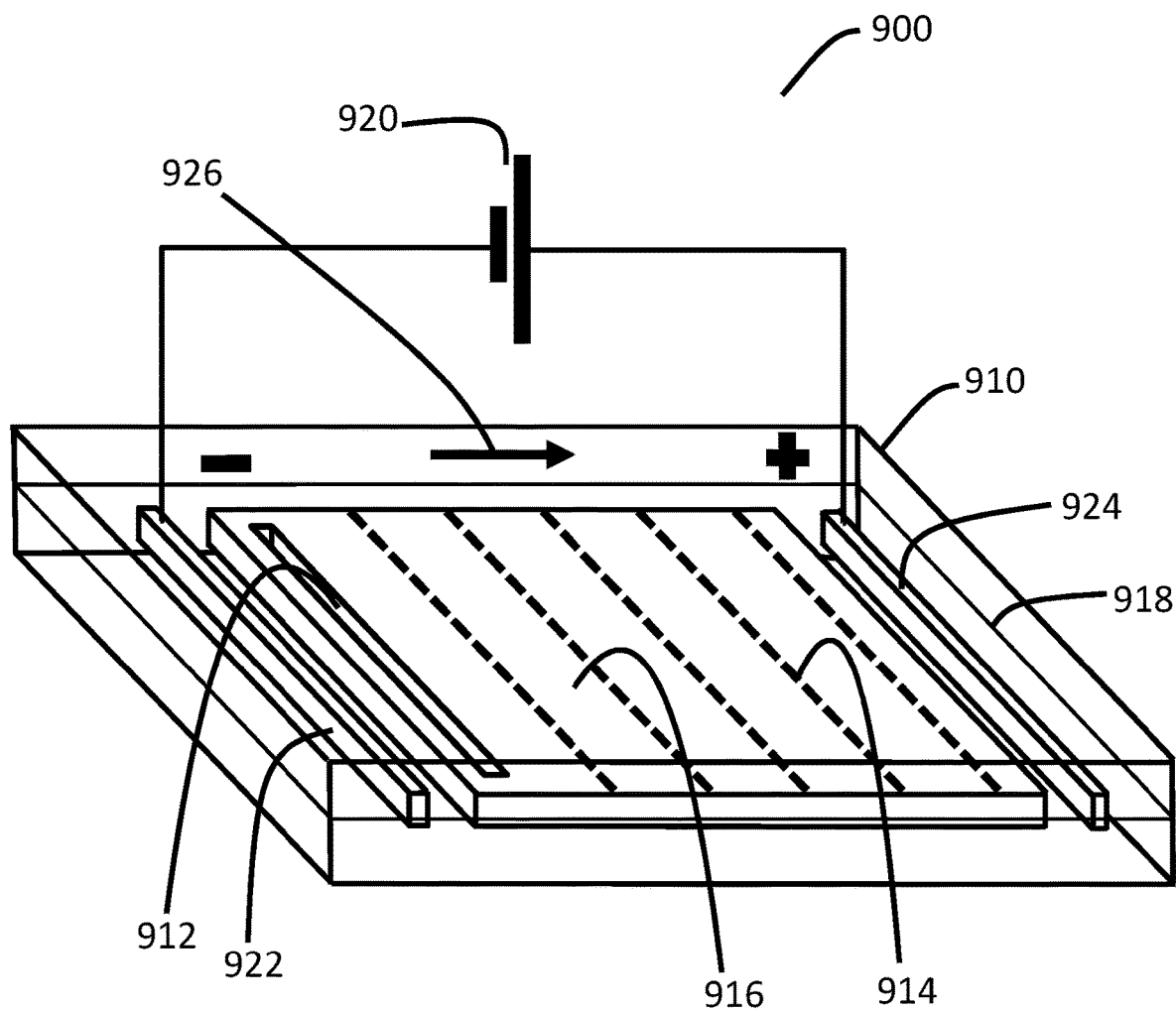
FIG. 6 schematically depicts an exemplary system for obtaining a high-molecular-weight fucan from a starting fucan composition by gel electrophoresis-extraction, the starting fucan having a broad molecular weight distribution.

An electrophoresis-extraction system 900 for obtaining a desired high-molecular-weight fucan from a starting fucan composition is shown in FIG. 6. Electrophoresis-extraction system 900 comprises an electrophoresis chamber 910, shown as transparent and containing electrophoresis gel 916, and an electrophoresis buffer 918. The electrophoresis gel 916 material may be, for example without limitation, one of agarose, polyacrylamide and a starch. The an electrophoresis buffer 918 may be for example without limitation one of tris-acetate EDTA, tris-borate EDTA and phosphate buffered saline. Proximate and parallel to a first side of electrophoresis gel 916 is fashioned within electrophoresis gel 916 a well 912 in which the starting fucan composition in solution is placed.

Direct current power supply 920 applies a potential difference across electrophoresis buffer 918 in electrophoresis chamber 910 by means of cathode 922 and anode 924. The electric potential difference between the cathode 922 and the anode 924 induces the fucan anions in the starting fucan composition to migrate along the gel away from the cathode 922 and toward the anode 924 along a direction given by migration direction arrow 926 so that, if the potential difference is maintained for a given period of time, different molecular weight molecules of the starting fucan composition will have been displaced from the well 912 by different distances toward the anode 924. The rate of displacement is determined by the mass to charge ratio of the fucan molecule. The lower molecular weight fucans will displace more rapidly and will, after a fixed period of time under the action of the electric potential difference, be displaced further than the higher molecular weight fucans. Theoretical displacement distances 914 indicate different theoretical distances of displacement of different molecular weight fucan molecules, the lower molecular weight fucan molecules being displaced further from the cathode 922 at any given period of time.

To obtain a desired high-molecular-weight fucan from the starting fucan composition post-electrophoresis, the corresponding portion of the electrophoresis gel 916 is selected and the high-molecular-weight fucan extracted from that portion of the gel. One non-limiting method of doing that is to submerge the portion of the electrophoresis gel 916 in an extractant solution and agitate the gel-solution mixture. In one embodiment, the agitation may be accomplished by shaking. In another embodiment, the agitation may be accomplished by high-shear mixing.

Membrane Dialysis

A high-molecular-weight fucan may be obtained from a broad molecular weight distribution starting fucan by membrane dialysis. Consistent with typical identification of dialysis membranes, the nominal MWCO value for a given dialysis membrane will selectively allow passage of a solution containing molecules generally having molecular weights less than the molecular weight of molecules that do not cross/permeate the dialysis membrane. Molecular weight cut-off values for dialysis membranes are typically not absolute for any given polymer or nominal cut-off value: a given dialysis membrane will pass or retain some molecules both above and below the nominal molecular weight cut-off. The actual cut-off/selectively values and effects of a nominal MWCO dialysis membrane for a particular polymer can be routinely determined for the particular polymer.

A number of factors can affect the permeation behavior of the dialysis membranes. These factors may be dependent on the dialysis membranes themselves or dependent on an attribute of the target polymers, for example the folding behavior and folded structure of the target polymer can affect the behavior of the target polymer in crossing/not-crossing the dialysis membrane's MWCO barrier. Regarding the dialysis membrane themselves, for example, manufacturing methods can cause a variety of hole sizes within the specific dialysis membrane, which variety can include holes both larger and smaller than the nominal MWCO cut-off. Thus, a dialysis membrane having a nominal molecular weight cut-off value will substantially allow passage of molecules below the nominal molecular weight cut-off value, but can also pass/retain some molecules below and/or above such value.

The methods can comprise subjecting the starting fucan composition comprising a desired high-molecular-weight segment to dialysis against a dialysate through a membrane with a molecular weight cut-off greater than 100 kDa to produce a dialyzed fucan composition comprising the high-molecular-weight fucan; and collecting the dialyzed fucan composition comprising the high-molecular-weight fucan.

Figure 7:
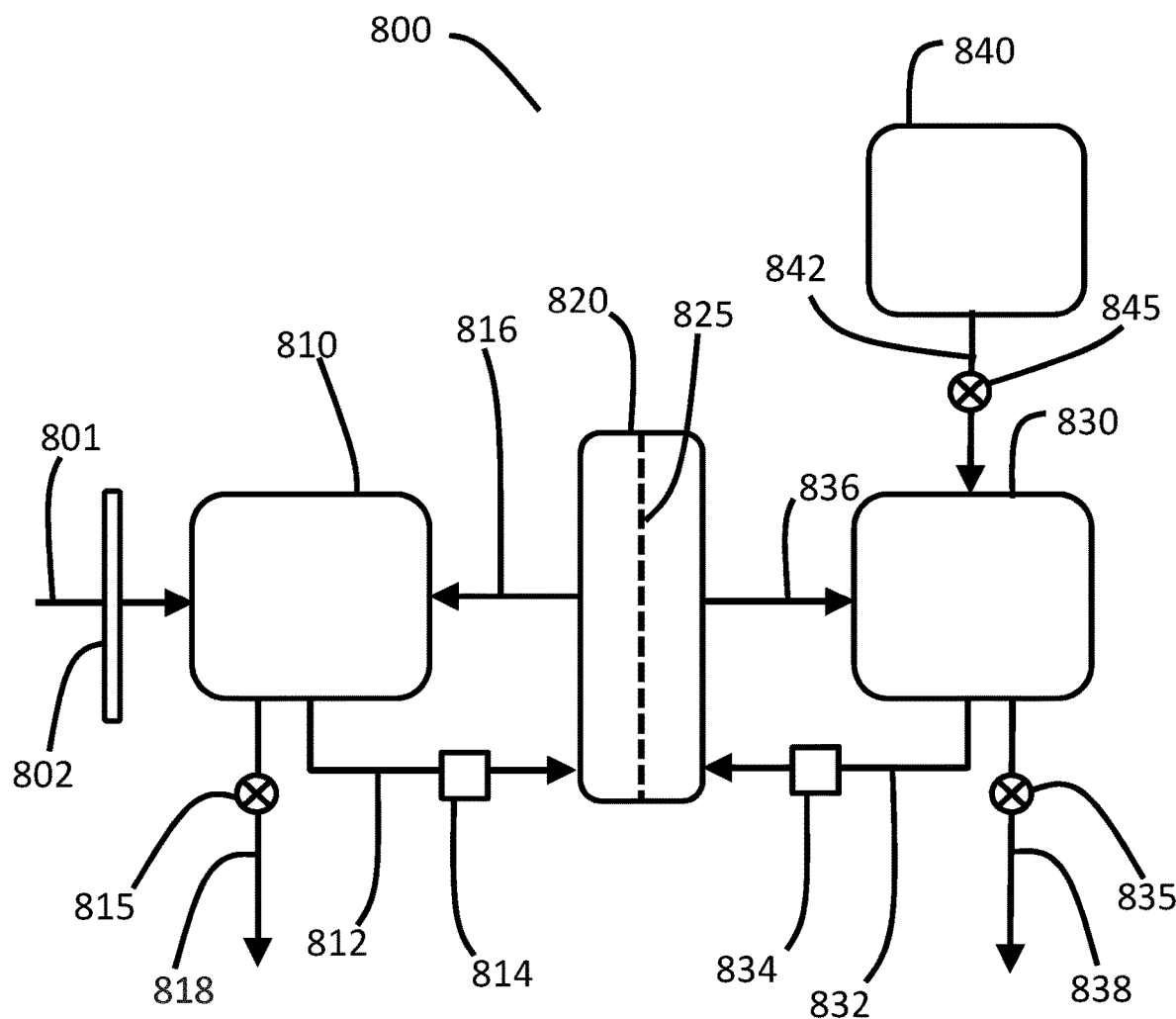
FIG. 7 schematically depicts an exemplary system for obtaining a high-molecular-weight fucan from a starting fucan composition by dialysis, the starting fucan having a broad molecular weight distribution.

Turning to FIG. 7, a membrane dialysis system 800 for obtaining a high-molecular-weight fucan from a starting fucan composition is shown. System 800 comprises a dialysis cell 820 having a dialysis membrane 825 that allows low molecular weight fucan molecules to pass through it. The starting fucan composition in a suitable solvent enters membrane dialysis system 800 and passes into fucan container 810 via input supply line 801 and through pre-filter 802. The pre-filter may be, for example a 0.22 µm pre-filter to remove unwanted particulate matter.

The pre-filtered starting fucan composition is circulated through the dialysis cell 820 on a first side of the dialysis membrane 825 by way of dialysis system supply line 812 and dialyzed fluid return line 816 by dialysis system pump 814. A dialysate fluid is circulated from dialysate container 830 through the dialysis cell 820 on a second side of the dialysis membrane 825 by way of dialysate supply line 832 and dialysate fluid return line 836 by dialysate pump 834. The dialysate fluid is selected to flow freely through the dialysis membrane 825. Suitable dialysate fluids include but are not limited to deionized water and solutions of sodium chloride, phosphate buffer, sodium phosphate, phosphate buffered saline, tris-HCl buffer, sodium citrate, citrate buffer, sodium ascorbate, ascorbic acid, sodium sulfite and ethylenediamine-tetraacetic acid (EDTA). Suitable dialysis membranes have pore sizes chosen to preferentially stop passage of fucan molecules of molecular weight greater than 200 kDa. Further suitable dialysis membranes have pore sizes that preferentially prevent the passage of molecules of molecular weight greater than 300 kDa, 500 kDa, and 1000 kDa. Each of these membranes may be employed to obtain a corresponding high-molecular-weight fucan from a starting fucan composition comprising fewer fucan molecules with molecular weights smaller than the dialysis membrane pore size or cut-off molecular weight relative to the broad starting molecular weight distribution. The dialysis membrane may be, without limitation, one of a cellulose ester and a regenerated cellulose membrane. The concentration of the solution containing the starting fucan composition may be between 0.1% w/v and 30% w/v.

As fucan molecules pass through dialysis membrane 825 their concentration builds up in the dialysate fluid and this starts to oppose the dialysis process. At a desired point in time dialysate supply valve 845 may be opened to allow fresh dialysate fluid into dialysate container 830 from dialysate supply container 840 via dialysate supply line 842.

After a suitable dialysis period, dialyzed fluid output valve 815 may be opened to allow the dialyzed fucan composition to be drawn from dialysis system 800 via dialyzed fluid output line 818. Dialysate fluid output valve 835 may be opened to allow the dialysis fluid containing low molecular weight fucan molecules to be drawn on dialysate fluid output line 838.

Selective Precipitation

A high-molecular-weight fucan may be obtained from a broad molecular weight distribution starting fucan by selective precipitation. The methods can comprise: providing the starting fucan composition comprising a desired high-molecular-weight segment as a solution of the starting fucan composition in water; adding to the solution containing the starting fucan composition a fucan-precipitant to obtain a supersaturated fucan-solvent mix; triggering precipitation of a portion of the broad molecular weight distribution starting fucan by adding an ionic-precipitation triggering compound to the supersaturated fucan-solvent mix to produce a precipitated high-molecular-weight fucan from the starting fucan composition and a solution containing remaining fucans; and extracting the precipitated high-molecular-weight fucan from the mix. Suitable fucan-precipitants include solvents with a relative polarity of less than 0.765, for example, ethanol, isopropanol, propanol, acetone, methanol, dimethyl sulfoxide, dimethyl formamide, ethylene glycol, tetrahydrofuran, acetonitrile, glyme, diglyme and dioxane, the solubility of the fucan decreasing as the polarity of the precipitating fluid decreases. The values for relative polarity can be normalized from measurements of solvent shifts of absorption spectra. See for example Christian Reichardt, Solvents and Solvent Effects in Organic Chemistry, Wiley-VCH Publishers, 3rd ed., 2003. Suitable ionic-precipitation triggering compounds include but are not limited to salts and bases of monovalent, divalent and trivalent cations, for example, chlorides, bromides, iodides, fluorides, sulfates, sulfites, carbonates, bicarbonates, phosphates, nitrates, nitrites, acetates, citrates, silicates, hydroxides, oxides and/or cyanides of an alkali metal, alkaline earth metal, aluminum and/or ammonium. In some embodiments, the ionic precipitation triggering compound comprises at least one of NaCl, KCl, NaOH, $MgCl_2$ and $CaCl_2$). Suitable concentrations of the starting fucan composition in water are between 0.01% w/v and 30% w/v. Particular fucans lending themselves to the above method include but are not limited to fucoidan.

The methods may further comprise desalting the starting fucan composition before adding the fucan-precipitant. The desalting may comprise diafiltrating the starting fucan composition across a molecular weight cutoff filter. The diafiltrating may comprise diafiltrating the starting fucan composition with distilled water. The diafiltrating may comprise diafiltrating the starting fucan composition across a molecular weight cutoff filter having a molecular weight cutoff smaller than a desired molecular weight in the desired high-molecular-weight fucan, for example, a 5 kDa, 10 kDa, 30 kDa, 50 kDa, 70 kDa, 100 kDa, 200 kDa or 300 kDa molecular weight cut-off. The methods may further comprise pre-filtering a solution containing the starting fucan composition through a suitable pre-filter to remove undesired particulate matter.

Extracting the precipitated high-molecular-weight fucan from the mix may comprise at least one of centrifugation, sedimentation, filtration and hydrodynamic flow separation.

Anionic Adsorption

A high-molecular-weight fucan may be obtained from a broad molecular weight distribution starting fucan by anionic adsorption. The methods can comprise: providing dissolved in a starting solution, the starting fucan composition having a broad starting molecular weight distribution comprising a desired high-molecular-weight segment; subjecting the starting fucan composition in the starting solution to ion exchange with an ion-exchange macroporous resin having a pore size based on a desired separation molecular weight within the starting fucan molecular weight distribution to convert the starting fucan composition into a first ion exchange-treated fucan composition; collecting the first ion exchange-treated fucan composition comprising the desired high-molecular-weight fucan; after the ion exchange with the starting fucan composition subjecting the macroporous resin to a salt solution to extract fucan molecules from the resin into the salt solution, producing a low molecular weight fucan-rich salt solution; desalting the low molecular weight fucan-rich salt solution to form a second ion exchange-treated fucan composition; and collecting the second ion exchange-treated fucan composition comprising a low-molecular-weight fucan.

The methods may further comprise desalting the starting fucan composition before the subjecting to ion exchange. The desalting may comprise diafiltrating the starting fucan composition across a molecular weight cutoff TFF filter. The diafiltrating may comprise diafiltrating the starting fucan composition across a molecular weight cutoff TFF filter having a molecular weight cutoff smaller than a desired molecular weight in the high-molecular-weight fucan, for example a 5 kDa, 10 kDa, 30 kDa, 50 kDa, 70 kDa, 100 kDa and/or a 300 kDa molecular weight cutoff TFF filter.

In another embodiment, a method for producing from a starting fucan composition a desired high-molecular-weight fucan composition, can comprise: providing dissolved in a starting solution a starting fucan composition having a broad starting molecular weight distribution comprising a desired high-molecular-weight segment; subjecting the dissolved starting fucan composition to ion exchange with an ion-exchange macroporous resin having a pore size based on a desired separation molecular weight within the starting fucan molecular weight distribution to convert the starting fucan composition into a first ion exchange-treated fucan composition; and collecting the first ion exchange-treated fucan composition comprising the desired high-molecular-weight fucan. The further embodiments may further comprise desalting the starting fucan composition before the subjecting to ion exchange. The desalting may comprise diafiltrating the starting fucan composition across a molecular weight cutoff TFF filter. The diafiltrating may comprise diafiltrating the starting fucan composition across a molecular weight cutoff TFF filter having a molecular weight cutoff smaller than a desired molecular weight in a molecular weight distribution of the desired high-molecular-weight fucan for example a 5 kDa, 10 kDa, 30 kDa, 50 kDa, 70 kDa, 100 kDa and/or a 300 kDa molecular weight cutoff TFF filter.

Subjecting the macroporous resin to a salt solution may comprise subjecting the macroporous resin to a sodium salt solution, for example a solution comprising at least one of a chloride, bromide, iodide, fluoride, sulfate, sulfite, carbonate, bicarbonate, phosphate, nitrate, nitrite, acetate, citrate, silicate and/or cyanide of an alkali metal, alkaline earth metal, aluminum and/or ammonium. Subjecting the macroporous resin to a sodium salt solution may comprise subjecting the macroporous resin to a sodium chloride solution. Desalting the low molecular weight fucan-rich salt solution may comprise diafiltrating the low molecular weight fucan-rich salt solution across a molecular weight cutoff TFF filter. The diafiltrating may comprise diafiltrating the low molecular weight fucan-rich salt solution across a molecular weight cutoff TFF filter having a molecular weight cutoff smaller than a desired molecular weight in a molecular weight distribution of the desired low molecular weight fucan-rich salt solution for example a 5 kDa, 10 kDa, 30 kDa, 50 kDa, 70 kDa and/or 100 kDa molecular weight cutoff TFF filter.

Subjecting the dissolved starting fucan composition to ion exchange with an ion-exchange macroporous resin may comprise adjusting a ratio of the starting fucan to resin to a predetermined mass ratio. The predetermined mass ratio may be between about 1:100 fucan:resin and about 10:1 fucan:resin, 5:1 fucan:resin, or 2:1 fucan:resin. In other embodiments, the predetermined mass ratio may be between about 1:100 fucan:resin and about 1:1 fucan:resin. In yet other embodiments, the predetermined mass ratio may be between about 1:100 fucan:resin and about 1:2 fucan:resin. In yet further embodiments, the predetermined mass ratio may be between about 1:50 fucan:resin and about 1:5 fucan:resin. In yet further embodiments, the predetermined mass ratio may be between about 1:20 fucan:resin and about 1:1 fucan:resin, for example, about 1:2 fucan:resin, 1:4 fucan:resin, 1:6 fucan:resin, 1:8 fucan:resin and 1:10 fucan:resin.

Subjecting the dissolved starting fucan composition to ion exchange with an ion-exchange macroporous resin may comprise subjecting the dissolved starting fucan composition to ion exchange with the resin for a predetermined period of time. The predetermined period of time may be between zero and 300 hours. In other embodiments, the predetermined period of time may be between zero and 100 hours. In further embodiments, the predetermined period of time may be between 5 minutes and 30 hours, for example between about 8 hours and about 24 hours. In yet further embodiments, the predetermined period of time may be between 1 and 10 hours, for example between about 4 hours and about 10 hours. In yet further embodiments, the predetermined period of time may be between about 2 and about 5 hours.

Subjecting the dissolved starting fucan composition to ion exchange with an ion-exchange macroporous resin may comprise subjecting the dissolved starting fucan composition to ion exchange with an anion-exchange macroporous resin. Subjecting the dissolved starting fucan composition to ion exchange with an anion-exchange macroporous resin may comprise subjecting the dissolved starting fucan composition to ion exchange with a strong base anion-exchange macroporous resin. Subjecting the dissolved starting fucan composition to ion exchange with an anion-exchange macroporous resin may comprise subjecting the dissolved starting fucan composition to ion exchange with a weak base anion-exchange macroporous resin. "Strong base" and "weak base" are used according to their ordinary meanings, for example a "strong base" being a resin that does not lose charge under any typical ion-exchange circumstances, for example a quaternary amine functionalized resin, and a weak base being a resin that does lose charge under high pH conditions, for example, a primary, secondary or tertiary amine functionalized resin. Subjecting the dissolved starting fucan composition to ion exchange may comprise subjecting the dissolved starting fucan composition to ion exchange with a mixed charge macroporous resin.

Subjecting the dissolved starting fucan composition to ion exchange with an anion-exchange macroporous resin may comprise subjecting the dissolved starting fucan composition to ion exchange with a macroporous resin comprising at least one of primary, secondary, tertiary and quaternary amine groups. The primary amine groups may be $NH_2$ groups. The secondary amine groups may be at least one of, for example without limitation, benzylamine groups and dimethyl amine groups. The tertiary amine groups may be at least one of, for example without limitation, diethylaminoethyl groups and dimethylaminoethyl groups. The quaternary amine groups may be for example without limitation trimethyl ammonium and triethyl ammonium groups. The resin may comprise, but is not limited to, one or more of styrene, agarose, dextran, acrylate, methacrylate, methyl methacrylate, butyl methacrylate, divinylbenzene, cellulose, silica, and ceramic.

Subjecting the dissolved starting fucan composition to ion exchange with an ion-exchange macroporous resin may comprise subjecting the dissolved starting fucan composition to ion exchange with an ion exchange resin having a pore size between 5 nm and 1000 nm, for example between 5 nm and 100 nm, between 10 nm or 15 nm and 50 nm, between 20 nm and 80 nm, between 5 nm and 30 nm, between 100 nm and 500 nm, between 300 nm and 900 nm or between 200 nm and 400 nm. Subjecting the dissolved starting fucan composition to ion exchange with an ion-exchange macroporous resin may comprise subjecting the dissolved starting fucan composition to ion exchange with an ion exchange resin has an exclusion limit of between 50 kDa and 50,000 kDa, for example between 50 kDa and 10,000 kDa, between 100 kDa and 5,000 kDa, between 10,000 kDa and 40,000 kDa, between 1,000 kDa and 9,000 kDa, between 2,000 kDa and 7,000 kDa or between 500 kDa and 2,000 kDa. The exclusion limit can be based on the exclusion limit for globular proteins.

Figure 8:
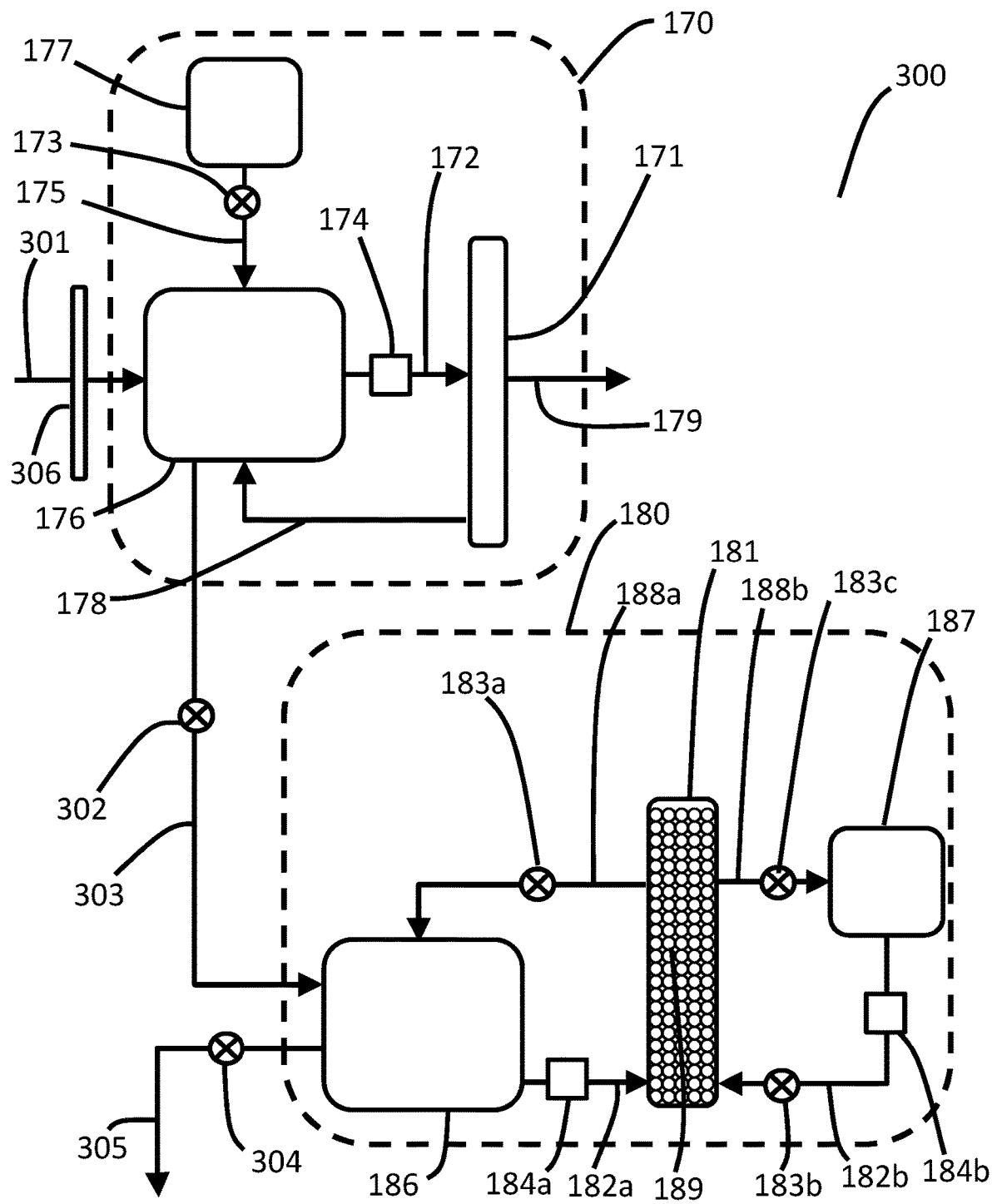
FIG. 8 schematically depicts an exemplary system for obtaining a desired high-molecular-weight fucan from a starting fucan composition using ion adsorption, the starting fucan having a broad molecular weight distribution.

FIG. 8 shows a schematic diagram of an exemplary ion adsorption system 300 for the segmentation of a fucan on the basis of molecular weight. A solution containing the starting fucan composition is supplied via input supply line 301 and pre-filter 306 to TFF subsystem fucan container 176. In a desalting process, tangential flow filtration (TFF) subsystem pump 174 pumps the starting fucan composition to TFF filter 171 of TFF subsystem 170 via TFF subsystem filter supply line 172. The format of the TFF filter 171 may be without limitation any one of a plate and frame system; a spiral wound cartridge system; a hollow fiber system; a flow cell system; and centrifugal filter system.

In the system of FIG. 8, TFF subsystem 170 serves as a desalination subsystem. TFF filter 171 is typically supplied as a cassette designed to allow an input fluid supplied to it to pass over its filter on its retentate side, while allowing a permeate to exit via one output line and treated input fluid to leave as retentate via another output line. For the present method, the cut off molecular weight of TFF filter 171 is chosen to allow permeation of salt components in the starting fucan solution while retaining the fucan in the retentate for subsequent ion adsorption treatment in ion exchange subsystem 180. TFF subsystem pump 174 maintains a level of pressure over TFF filter 171 between its retentate and permeate sides. In FIG. 8, the retentate of TFF filter 171 is returned to TFF subsystem fucan container 176 via TFF subsystem retentate line 178, while permeate containing the unwanted non-fucan salt components is produced via TFF subsystem permeate output line 179 for use outside TFF subsystem 170 or to be discarded.

While TFF subsystem pump 174 recirculates the starting fucan composition and retentate over TFF filter 171, water or a low conductivity flush solution from TFF subsystem solvent container 177 may be supplied via TFF subsystem solvent supply line 175. The flush solution is used to replenish retentate solution lost via the permeate on TFF subsystem permeate output line 179 and/or to ensure that a predetermined number of diavolumes of input starting fucan and solvent are circulated over the TFF filter 171. By controlling TFF subsystem solvent supply valve 173, flush solution may be added in a pulse process. In other embodiments, the solvent may be added in a continuous mode. The continuous mode of adding the solvent has efficiency benefits. The number of diavolumes of solvent to process over TFF filter 171 may be predetermined. In some embodiments, the solvent may be deionized water.

Inter-subsystem valve 302 may be shut during the above processing, and retentate of TFF filter 171 of TFF subsystem 170 collected into a container (not shown) before being supplied to ion exchange subsystem fucan container 186 of ion exchange subsystem 180. The collected retentate may then be supplied to ion exchange subsystem fucan container 186 of ion exchange subsystem 180 via TFF subsystem retentate output line 303. In other embodiments, the collected retentate may be transferred in a container (not shown) to ion exchange subsystem fucan container 186. In yet other embodiments of the system, the inter-subsystem valve 302 may be maintained open and the retentate of TFF filter 171 may be supplied via TFF subsystem retentate output line 303 on a continuous basis to ion exchange subsystem fucan container 186. The retentate supplied to ion exchange subsystem 180 may be anticipated to have a lower salt content remaining that may interfere with the processing of fucan in ion exchange subsystem 180 and is a desalinated fucan composition.

Ion exchange container 181 of ion exchange subsystem 180 contains a volume of macroporous ion exchange resin 189. In some embodiments, the macroporous ion exchange resin is an anion exchange resin. In some embodiments, the macroporous ion exchange resin is a mixed charge resin. The pore size of the macroporous ion exchange resin 189 is chosen to preferentially adsorb fucan molecules of molecular weight below a predetermined value from a solution containing a broad molecular weight distribution starting fucan, preferentially leaving behind in the solution fucan molecules that have a greater molecular weight than the predetermined value. One form of this category of resin is based on substantially spherical particles of styrene cross-linked with divinylbenzene and having pores containing quaternary ammonium groups. In some embodiments, the pore size may be between 10 nm and 100 nm. The fucan molecules may or may not be preferentially adsorbed into the pores of the resin based on the hydrodynamic size of the fucan molecules.

During the processing of the desalinated fucan composition from TFF subsystem 170 in ion exchange container 181, ion exchange subsystem output valve 304 controlling the ion exchange subsystem output line 305 from ion exchange subsystem fucan container 186 may be closed. Ion exchange subsystem salt solution supply valve 183b and ion exchange subsystem salt solution return valve 183c may similarly be closed and ion exchange subsystem fucan return valve 183a opened. While ion exchange subsystem fucan pump 184a recirculates a solution containing the desalinated fucan composition through ion exchange container 181 via ion exchange subsystem fucan supply line 182a and ion exchange subsystem fucan pump 184a, macroporous ion exchange resin 189 adsorbs the lower molecular weight fucan molecules, thereby causing the solution in ion exchange subsystem fucan return line 188a to contain the desired high-molecular-weight fucan. After flowing through the ion exchange container 181, the solution containing the desired high-molecular-weight fucan is returned to ion exchange subsystem fucan container 186 via ion exchange subsystem fucan return line 188a.

The average molecular weight of the fucans in ion exchange subsystem fucan container 186 may be measured or monitored. When the solution in ion exchange subsystem fucan container 186 has been circulated for a suitable period of time, or when the fucans in the solution have attained a predetermined desired average molecular weight value, ion exchange subsystem output valve 304 may be opened to produce a first ion exchange treated fucan composition as the first output product of ion adsorption system 300 via ion exchange subsystem output line 305. This first output product comprises, for example, a high-molecular-weight fucan with a molecular weight distribution wherein the quantity of the input starting fucan broad molecular weight distribution at the low molecular weight end has been suppressed or attenuated such that the resulting molecular weight distribution is displaced towards the higher end of the molecular weight distribution of the input starting fucan composition supplied to ion adsorption system 300 on input supply line 301.

Ion exchange subsystem output valve 304 may be closed again, as may ion exchange subsystem fucan return valve 183a, and ion exchange subsystem salt solution supply valve 183b and ion exchange subsystem salt solution return valve 183c opened to allow salt solution from ion exchange subsystem salt solution container 187 to enter the circulation in ion exchange subsystem 180 via ion exchange subsystem salt solution supply line 182b. Ion exchange subsystem salt solution pump 184b now circulates salt solution via ion exchange subsystem salt solution supply line 182b through the macroporous ion exchange resin 189 in ion exchange container 181 and back to ion exchange subsystem salt solution container 187 via ion exchange subsystem salt solution return line 188b and ion exchange subsystem salt solution return valve 183c. In this process, the salt displaces the fucan adsorbed within the pores of the macroporous ion exchange resin and releases the freed fucan into the salt solution in circulation in ion exchange subsystem 180. The salt solution may be circulated for a predetermined time. In other embodiments, the average molecular weight of the fucan in the salt solution in ion exchange subsystem 180 may be measured and the recirculation of the salt solution terminated when the average molecular weight of the fucan in salt solution reaches a predetermined desired value.

In some embodiments, a predetermined amount of a low ionic content solution may be used to wash the resin prior to initiating the circulation of salt solution from ion exchange subsystem salt solution container 187. In some embodiments, this low ionic content solution may be deionized water.

At this point ion exchange subsystem output valve 304 may be opened again and the pumps and valves of ion exchange subsystem 180 suitably operated to allow the second product of ion adsorption system 300 drawn from ion exchange subsystem output line 305 in the form of a low molecular weight fucan-rich salt solution. The second product may be filtered, for example without limitation in a centrifuge over a suitable centrifugal filter or tangential flow filtration filter, to separate the low-molecular-weight fucan from the unwanted salt. This produces a second output low-molecular-weight fucan. This second output low-molecular-weight fucan, in contrast with the first output high-molecular-weight fucan discussed above, has a fucan molecular weight distribution wherein a portion of the input starting fucan broad molecular weight distribution at the high-molecular-weight end has been suppressed or attenuated such that the resulting molecular weight distribution is displaced towards the lower end of the molecular weight distribution of the input starting fucan composition supplied to ion adsorption system 300 on input supply line 301.

Given the width and complexity of the starting fucan molecular weight distribution and the vagaries of polymer behavior and ion exchange resins, the two output fucan molecular weight distributions may not peak where anticipated from a consideration of the pore size of the macroporous ion exchange resin. If that occurs, however, the two output fucan molecular weight distributions will still be displaced with respect to each other, representing the segmentation of the starting fucan composition into a comparatively higher molecular weight fucan corresponding to the first product, and a comparatively lower molecular weight fucan corresponding to the second product. The first product corresponds to large and heavy fucan molecules preferentially not adsorbed by the resin, while the second product conversely corresponds to fucan molecules preferentially adsorbed by the resin and are on average smaller and lighter than those not adsorbed.

Preparative Gel Permeation Chromatography

A high-molecular-weight fucan may be obtained from a broad molecular weight distribution starting fucan by preparative gel permeation chromatography. The methods can comprise providing packed in a column format a gel media specified for gel permeation chromatography (GPC) of polymers in an aqueous solution; providing a starting fucan composition comprising a desired high-molecular-weight segment dissolved in an aqueous solvent suitable for gel permeation chromatography on the gel media; subjecting the solution containing the starting fucan composition to preparative gel permeation chromatography, wherein the fucan is displaced according to molecular weight across the gel media in the column at a predetermined flow rate between a first input end of the column and a second output end of the column; collecting eluent from the second output end of the column in pre-determined aliquots based on a desired segmentation of the starting fucan composition, each aliquot comprising a segmented fucan composition; pooling the desired aliquots based on the desired segmentation of the starting fucan composition to obtain a pooled GPC aliquot composition comprising the desired high-molecular-weight fucan.

Subjecting the solution containing the starting fucan composition to preparative gel permeation chromatography may comprise first pre-filtering the starting fucan composition in solution through a pre-filter to remove undesired particulate matter. Subjecting the solution containing the starting fucan composition to preparative gel permeation chromatography may comprise preparing the starting fucan composition in a solution at a concentration of between 0.1% w/v and 20% w/v. Subjecting the solution containing the starting fucan composition to preparative gel permeation chromatography may comprise using at least one of a peristaltic pump, isocratic pump, binary pump, quaternary pump and gradient pump to accomplish the displacement across the column containing gel media. Subjecting the solution containing the starting fucan composition to preparative gel permeation chromatography may comprise displacing the solution across the column containing the gel media at a predetermined flow rate of between 0.0005 milliliters per minute per gel media surface area ($mL/min/cm^2$) to 5 $mL/min/cm^2$, between 0.005 $mL/min/cm^2$ to 0.5 $mL/min/cm^2$, between 0.01 $mL/min/cm^2$ to 0.25 $mL/min/cm^2$, 0.05 $mL/min/cm^2$, 0.1 $mL/min/cm^2$, 0.15 $mL/min/cm^2$ and 0.2 $mL/min/cm^2$.

Collecting eluent from the second output end of the column may comprise collecting aliquots of eluent between about 0.1 mL and 1000 mL, between about 1 mL and 100 mL, between about 5 mL and 50 mL, about 10 mL, about 20 mL, about 30 mL and about 40 mL. Collecting the aliquots from the second output end of the column may comprise measuring the molecular weight distributions of the aliquots by analytical GPC. Measuring the aliquots by analytical GPC may be done simultaneously with the collecting of the column eluent.

Pooling the desired aliquots may involve measuring the molecular weight distributions of the aliquots by analytical GPC and pooling only aliquots with desired molecular weight distributions. Pooling the desired aliquots may be done simultaneously with the collecting of the column eluent.

The gel media used may comprise at least one of polyhydroxymethacrylate, sulfonated styrene-divinylbenzene, silica, a hydrophilic bonded phase or polymer, polystyrene, divinylbenzene, methacrylate, methyl methacrylate, butyl methacrylate, cellulose, ceramic, agarose and dextran. The gel media used may have pores with diameters of at least one of about 3 nm, 5 nm, 10 nm, 20 nm, 50 nm, 100 nm, 200 nm, 500 nm, 1,000 nm, 2,000 nm, 3,000 nm, 5,000 nm and 10,000 nm. The gel media used may have pores with exclusion limits of at least one of about 100 Da, 100 kDa 1,000 kDa, 5,000 kDa, 10,000 kDa, 30,000 kDa, 50,000 kDa and 100,000 kDa. The exclusion limits may be based on the exclusion limit for globular proteins, or a polysaccharide, for example, dextran and/or pullulan.

The solvent used to dissolve the starting fucan composition may comprise at least one of water, sodium nitrate, lithium nitrate, monosodium phosphate, disodium phosphate, trisodium phosphate, lithium chloride, lithium bromide, lithium iodide sodium chloride, sodium bromide, sodium iodide, potassium chloride, potassium bromide, potassium iodide, sodium hydroxide, lithium hydroxide, potassium hydroxide, sodium sulfate, sodium sulfite, methanol, ethanol and acetonitrile.

Chemical Structural Modification

The methods, systems etc. discussed herein can comprise chemical structural modification of the fucan composition, particularly the fucans in the fucan composition. The chemical structural modification may involve removal of functional groups from the fucan, for example, 0-acetyl, N-acetyl, methoxy, hydroxyl, carboxylic and/or sulfate functional groups from the fucan structure. The chemical structural modification may involve the use of a wide variety of chemical reagents, for example, acids, bases, detergents and/or oxidizing agents.

Diseases and Conditions
Fibrous Adhesions

A fibrous adhesion is a type of scar that forms between two parts of the body, usually after surgery (surgical adhesion). Fibrous adhesions can cause severe problems. For example, fibrous adhesions involving the female reproductive organs (ovaries, Fallopian tubes) can cause infertility, dyspareunia and severe pelvic pain. Fibrous adhesions that occur in the bowel can cause bowel obstruction or blockage, and fibrous adhesions can also form in other places such as around the heart, spine and in the hand. In addition to surgery, fibrous adhesions can be caused for example by endometriosis, infection, chemotherapy, radiation, trauma and cancer.

A variety of fibrous adhesions are discussed in this document. Terms such as surgical adhesions, post-surgical adhesions, postoperative adhesions, adhesions due to pelvic inflammatory disease, adhesions due to mechanical injury, adhesions due to radiation, adhesions due to radiation treatment, adhesions due to trauma, and adhesions due to presence of foreign material all refer to adherence of tissues to each other due to a similar mechanism and are all included in the term fibrous adhesions.

Fibrous adhesion formation is a complex process in which tissues that are normally separated in the body grow into each other. Surgical adhesions (also known as post-surgical adhesions) develop from the otherwise normal wound healing response of the tissues to trauma and have been reported to occur in over two-thirds of all abdominal surgical patients (Ellis, H., Surg. Gynecol. Obstet. 133: 497 (1971)). The consequences of these fibrous adhesions are varied and depend upon the surgical site or other site, such as a disease site, involved. Problems may include chronic pain, obstruction of the intestines and even an increased risk of death after cardiac surgery (diZerega, G. S., Prog. Clin. Biol. Res. 381: 1-18 (1993); diZerega, G. S., Fertil. Steril. 61:219-235 (1994); Dobell, A. R., Jain, A. K., Ann. Thorac. Surg. 37: 273-278 (1984)). In women of reproductive age, fibrous adhesions involving the uterus, fallopian tubes or ovaries are estimated to account for approximately 20% of all infertility cases (Holtz, G., Fertil. Steril. 41: 497-507 (1984); Weibel, M. A. and Majno, G. Am. J. Surg. 126: 345-353 (1973)).

The process of fibrous adhesion formation initially involves the establishment of a fibrin framework and normal tissue repair. The normal repair process allows for fibrinolysis alongside mesothelial repair. However, in fibrous adhesion formation the fibrin matrix matures as fibroblasts proliferate into the network and angiogenesis occurs resulting in the establishment of an organized fibrous adhesion within about 3 to 5 days (Buckman, R. F., et al., J. Surg. Res. 21: 67-76 (1976); Raferty, A. T., J. Anat. 129: 659-664 (1979)). Inflammatory processes include neutrophil activation in the traumatized tissues, fibrin deposition and bonding of adjacent tissues, macrophage invasion, fibroblast proliferation into the area, collagen deposition, angiogenesis and the establishment of permanent fibrous adhesion tissues.

Various attempts have been made to prevent surgical adhesions. These involve pharmacological approaches targeted at influencing the biochemical and cellular events that accompany surgical traumas well as barrier methods for the separation of affected tissues. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Currently, preventive therapies also include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran (Adhesion Study Group, Fertil. Steril. 40:612-619 (1983)), or carboxymethyl cellulose (Elkins, T. E., et al., Fertil. Steril. 41:926-928 (1984)), into the surgical space in an attempt to keep the organs apart. Synthetic barrier membranes made from oxidized regenerated cellulose (e.g., Interceed™), polytetrafluoroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans (Burns, J. W., et al., Eur. J. Surg. Suppl. 577: 40-48 (1997); Burns, J. W, et al., Fertil. Steril. 66:814-821 (1996); Becker, J. M., et al., J. Am. Coll. Surg. 183:297-306 (1996)). The success of these HA/CMC membranes may derive from their ability to provide tissue separation during the peritoneal wound repair process when fibrous adhesions form. The membranes were observed to form a clear viscous coating on the injured tissue for 3-5 days after application, a time period that is compatible with the time course of post-surgical adhesion formation (Ellis, H., *Br. J. Surg.* 50: 10-16 (1963)). Unfortunately, limited success has been seen with these methods.

Peritonitis involves inflammation of the peritoneum. Peritonitis can cause severe problems. For example, abdominal pain, abdominal tenderness and abdominal guarding. Peritonitis may involve spontaneous, anatomic and/or peritoneal dialysis related inflammation. Peritonitis may involve an infection, for example, perforation of a hollow viscus, disruption of the peritoneum, spontaneous bacterial peritonitis, and systemic infections may result in infection and peritonitis. Peritonitis may also not involve an infection, for example, leakage of sterile body fluids into the peritoneum, and sterile abdominal surgery may result in peritonitis. Various attempts have been made to prevent and/or treat peritonitis. For example, general supportive measures such as intravenous rehydration, antibiotics, and surgery. There is an unmet need for compounds, compositions, methods and the like (including delivery approaches) to inhibit, or otherwise treat and/or prevent, peritonitis, preferably more effectively with few side effects.

The high-molecular-weight fucans discussed herein can be used to treat fibrous adhesions in a patient and can be included as a component of, or be, a high-molecular-weight fucan medical composition, medical device, combination or pharmaceutical product configured and can be composed to treat fibrous adhesions. For example, a high-molecular-weight fucan medical composition or medical device comprising between about 0.02 mg/mL to about 100 mg/mL, for example 0.1 mg/mL, 0.2 mg/mL, 0.3 mg/mL, 0.5 mg/mL, 0.9 mg/mL, 1 mg/mL, 2.5 mg/mL, 5 mg/mL 7.5 mg/mL, of a high-molecular-weight fucan herein dissolved in a physiological salt solution. The physiological salt solution can be, for example, Lactated Ringer's Injection USP (LRS), normal saline and physiological Dextran solution.

The high-molecular-weight fucan medical compositions and medical devices, which can be liquid medical compositions and devices, herein can contain pharmaceutically acceptable excipients such as buffers, stabilizers, preservatives, adjuvants, etc. Such high-molecular-weight fucan medical compositions and medical devices can be used to treat fibrous adhesions pre-, during, or post-surgery by administering between about 0.01 mL/kg (per kilogram bodyweight of the patient or target) to about 10 mL/kg or 15 mL/kg of the fucan medical compositions or devices in the preceding paragraph. Doses and device quantities include, for example, about 0.03 mL/kg, 0.1 mL/kg, 0.2 mL/kg, 0.4 mL/kg, 0.5 mL/kg, 0.6 mL/kg, 1 mL/kg, 1.2 mL/kg, 2 mL/kg, 3 mL/kg, 4 mL/kg, 5 mL/kg, 8 mL/kg, 10 mL/kg and 15 mL/kg of the high-molecular-weight fucan medical composition or medical device to the surgical site of the patient. In further embodiments, such high-molecular-weight fucan medical compositions and medical devices can be used to treat fibrous adhesions at any selected target site, for example lesions, abrasions, injury sites, surgical sites and post-surgical sites by administering between about 0.04 mg/kg or 0.1 mg/kg to about 25 mg/kg or 50 mg/kg. Some examples of such doses include, for example, about 0.04 mg/kg, 0.075 mg/kg, 0.1 mg/kg, 0.2 mg/kg, 0.5 mg/kg, 1 mg/kg, 1.3 mg/kg, 2 mg/kg, 3 mg/kg, 4 mg/kg, 5 mg/kg, 7.5 mg/kg, 8 mg/kg, 10 mg/kg, 15 mg/kg, 20 mg/kg, 25 mg/kg and 50 mg/kg of the fucans herein, including for example the high-molecular-weight fucans herein, to the surgical site of the patient. The administering can be accomplished, for example, by instilling a liquid medical composition or medical device generally throughout the target area; directing the liquid medical composition or medical device at a specific location(s) within the target area; spraying the liquid medical composition or medical device generally or at a specific location(s) within the target area; or, spraying or otherwise delivering the liquid medical composition or medical device via an applicator, which can be a spray applicator through a trocar, catheter, endoscope or other minimally invasive device, onto a specific location(s) that a surgeon or other practitioner has identified as particularly susceptible to or concerning for development of fibrous adhesions. In another aspect, the administering can be done after opening of the surgical wound but before the surgical procedure; during the surgical procedure, or after the surgical procedure but before the surgical wound has been closed. If desired, the liquid medical composition or medical device can also be administered after the surgery is completed (for example through a syringe and needle) and can be administered to non-surgical target sites as well. The surgical site of the patient can be, for example, at least one of the pelvic cavity, abdominal cavity, dorsal cavity, cranial cavity, spinal cavity, ventral cavity, thoracic cavity, pleural cavity, pericardial cavity, skin, joints or muscles. The administering of the high-molecular-weight fucan medical composition or medical device into the surgical site of the patient can be accomplished in less than about 15 minutes, 10 minutes, 8 minutes, 6 minutes, 5 minutes, 4 minutes, 3 minutes, 2 minutes, 1 minute, 45 seconds, 30 seconds, 20 seconds, 15 seconds, 10 seconds and 5 seconds.

Examples of administering the high-molecular-weight fucan medical composition or medical device to a surgical site include without limitation administering the high-molecular-weight fucan medical composition or medical device at the surgical site of a Cesarean section surgical procedure; a microvascular free flap reconstruction surgical procedure, a full thickness skin graft surgical procedure, a V-Y advancement flap surgical procedure, a fasciocutaneous rotation flap surgical procedure, an arthroplasty surgical procedure, a mastectomy surgical procedure, a sequestrectomy surgical procedure, a saucerization surgical procedure, an osteotomy surgical procedure, an osteoplasty surgical procedure, a patellectomy surgical procedure, a synovectomy surgical procedure, a capsulectomy surgical procedure, a tendon or ligament repair surgical procedure, a tenolysis surgical procedure, a tenotomy surgical, a fasciotomy surgical procedure, a meniscal repair surgical procedure, a vertebrectomy surgical procedure, a ethmoidectomy surgical procedure, a Caldwell Luc's operation surgical procedure, a dacryocystorhinostomy surgical procedure, a lysis nasal synechia surgical procedure, a thymectomy surgical procedure, a pneumonolysis surgical procedure, a pneumonectomy surgical procedure, thoracoplasty surgical procedure, a bilobectomy surgical procedure, a portal hypertension surgery surgical procedure, a splenectomy surgical procedure, a esophagectomy surgical procedure, a peritonitis surgery surgical procedure, a gastrectomy surgery surgical procedure, a jejunojejunostomy surgery surgical procedure, a laparoscopic cholecystectomy surgery surgical procedure, a laparoscopic common bile duct exploration surgical procedure, a gastroenterostomy surgical procedure, a bariatric surgery surgical procedure, a bowel resection & anastomosis surgical procedure, a segemental hepatectomy surgical procedure, a lobectomy surgical procedure, a pancreatomy surgical procedure, a pancreaticoduodenectomy surgical procedure, a tumor resection surgical procedure, a laparoscopic nephrectomy surgical procedure, a cystectomy surgical procedure, an abdominal or pelvic adhesion lysis surgical procedure, a hysterosalpingostomy surgical procedure, a salpingoplasty surgical procedure, an ectopic pregnancy laparoscopic surgery surgical procedure, a joint replacement surgery surgical procedure, a broken bone repair surgical procedure, a hysterectomy surgical procedure, a gallbladder removal surgical procedure, a heart bypass surgical procedure, an angioplasty surgical procedure, an atherectomy surgical procedure, a breast biopsy surgical procedure, a carotid endarterectomy surgical procedure, a cataract surgery surgical procedure, a coronary artery bypass surgical procedure, a dilation and curettage surgical procedure, a hernia repair surgical procedure, a lower back pain surgery surgical procedure, a partial colectomy surgical procedure, prostatectomy surgical procedure and a tonsillectomy surgical procedure, after opening the surgical wound, during surgery, before closing the surgical wound and/or after closing the surgical wound.

Cancers Generally

Cancer has been the second leading cause of death in the U.S. and accounts for over 20% of all mortalities. Cancer is a proliferative disease and is characterized by the uncontrolled division of certain cells, which may lead to the formation of one or more tumors. A number of methods are used to treat cancer, including surgery, radiation, chemotherapy and combinations thereof. Although surgery is a relatively common method used for some localized tumors, there is still a significant chance of tumor recurrence after tumor excision.

Treating cancers and other proliferative diseases has been limited by the potential for damage or toxicity to non-cancerous, healthy tissues. In radiation and surgical treatments, the procedure has been generally confined to and proximal to the tumor sites. However, there can be significant risk to patients undergoing surgical removal of cancerous tissues (e.g., in removal of prostate or brain tumors there can be a significant risk of non-repairable damage to surrounding vital tissues, for example via potential reduced need for resection of non-tumor tissues. Furthermore, in focused radiation treatment, which has been given as a first line treatment for prostate cancer, there are similar risks. In the chemotherapeutic treatment of cancer, the drug has been administered systemically, so that the whole body is exposed to the drug. These drugs are designed to be toxic to cancer cells, but they are also (generally) toxic to non-cancerous cells so that patients become quite ill when undergoing drug treatments for cancer. Through experience, oncologists are able to give doses of these drugs that may be tolerated by some patients. However, these doses are often not successful in treating cancers.

One problem with any method of treating cancer has been the local recurrence of the disease. For example, approximately 700,000 Americans are diagnosed with localized cancer annually (approximately 64% of all cancer patients) and almost half a million are treated using surgical methods. Unfortunately, 32% of patients treated with surgery relapse after the initial treatment (approximately 21% relapse at the initial surgical site and 11% at distant metastatic sites). Almost 100,000 patients die annually due to localized recurrence of cancer. This has been especially true in breast cancer where 39% of patients undergoing lumpectomy will experience local recurrence of the disease.

Staging is a method of judging the progress of the cancer (solid tumor) in a patient. A simplified approach puts patients into three groups or stages based on how far the cancer has advanced:

Stage 1: The cancer can be treated by surgically removing part of the organ. This is also known as the resectable stage.

Stage 2: The cancer has advanced past the point of being resectable but is still confined to the organ itself.

Stage 3: The tumor has spread to other organs.

Many cancers are treated with anti-proliferative agents including, for example, 5-fluorouracil (Efudex®), vinca alkaloids (for example, vincristine (Oncovin®)), anthracyclines (for example, doxorubicin (Adriamycin®)), cisplatin (Platinol-AQ®), gemcitabine hydrochloride (Gemzar®), methotrexate and paclitaxel. Some examples of the toxicities associated with the anti-proliferative agents, methotrexate and paclitaxel, are discussed elsewhere herein. Methotrexate has been used to treat several cancers including, for example, bladder, breast, cervical, head and neck, hepatic, lung, and testicular cancers. Paclitaxel has been used to treat several cancers including, for example, ovarian, breast, and non-small cell lung cancers (*Compendium of Pharmaceutical and Specialties Thirty-fifth Edition*, 2000).

Toxicities due to 5-fluorouracil can include cardiovascular toxicity such as myocardial ischemia; central nervous system toxicities such as euphoria, acute cerebellar syndrome and ataxia; dermatologic toxicities such as alopecia and dermatitis; gastrointestinal toxicities such as nausea, vomiting and oral or gastrointestinal ulceration; hematologic toxicities such as leukopenia, thrombocytopenia and anemia; hypersensitivity toxicities such as anaphylaxis and contact hypersensitivity; ocular toxicities such as increased lacrimation, photophobia and conjunctivitis; and, other toxicities such as fever. 5-fluorouracil has been used to treat many cancers including, for example, breast, colorectal, gastric, hepatic, bladder, head and neck, non-small cell lung, ovarian, pancreatic, and prostate cancers (*Compendium of Pharmaceutical and Specialties Thirty-fifth Edition*, 2000).

Toxicities due to vincristine include central nervous system toxicities such as seizures in children and hallucinations; dermatologic toxicity such as alopecia; extravasation toxicity such as vesicant; gastrointestinal toxicities such as nausea, vomiting, constipation and stomatitis; hematologic toxicity such as myelosuppression; neurologic toxicities such as peripheral neuropathy and autonomic neuropathy; ocular toxicities such as double vision, transient blindness and optic atrophy; renal/metabolic toxicities such as urinary retention, hyperuricemia and bladder atony; respiratory toxicity such as shortness of breath; and, other toxicity such as fever in children. This anti-proliferative agent has been used to treat several cancers including, for example, Hodgkin's disease, small cell lung, Wilm's tumor, and testicular cancers (*Compendium of Pharmaceutical and Specialties Thirty-fifth Edition*, 2000).

Toxicities due to doxorubicin include cardiovascular toxicities such as electrocardiographic abnormalities and cardiomyopathy; dermatologic toxicities such as alopecia and nail changes; extravasation hazard toxicity such as vesicant; gastrointestinal toxicities such and nausea, vomiting and stomatitis; genitourinary toxicity such as red coloration of urine; hematologic toxicity such as myelosuppression; hypersensitivity toxicities such as anaphylaxis and skin rash; ocular toxicity such as conjunctivitis; reproductive toxicity such as infertility; and, other toxicity such as hyperuricemia. This anti-proliferative agent has been used to treat several cancers including, for example, breast, small cell lung, and ovarian cancers (*Compendium of Pharmaceutical and Specialties Thirty-fifth Edition*, 2000).

Toxicities due to cisplatin include cardiovascular toxicity such as electrocardiographic changes; dermatologic toxicity such as hyperpigmentation; extravasation hazard toxicity such as irritant; gastrointestinal toxicities such as nausea and vomiting; hematologic toxicities such as myelosuppression and hemolytic anemia; hypersensitivity toxicity such as anaphylactic; neuromuscular toxicity such as peripheral neuropathy and acute encephalopathy; ocular toxicity such as retrobulbar neuritis; otologic toxicities such as hearing loss and tinnitus; renal/metabolic toxicities such as toxic nephropathy and hypokalemia; and, other toxicity such as infertility. This anti-proliferative agent has been used to treat several cancers including, for example, bladder, small cell lung, ovarian, testicular, brain, breast, cervical, head and neck, hepatoblastoma, and thyroid cancers (*Compendium of Pharmaceutical and Specialties Thirty-fifth Edition,* 2000). Toxicities due to gemcitabine hydrochloride include, for example, hematologic toxicities such as myelosuppression; gastrointestinal toxicities such as nausea, vomiting and stomatitis; hepatic toxicities such as transient elevations of serum transaminases; renal toxicities such as proteinuria, hematuria, hemolytic uremic syndrome and renal failure; dermatologic toxicity such as rash and alopecia; edema toxicities such as edema and peripheral edema; and, other toxicity such as fever. This anti-proliferative agent has been used to treat pancreatic and non-small cell lung cancers (*Compendium of Pharmaceutical and Specialties Thirty-fifth Edition,* 2000).

The present discussion comprises prevention or treatment of localized cancers or solid tumors that can be treated include those of the prostate, breast, pancreas, liver, kidney, genitourinary system, brain, gastrointestinal system, respiratory system, and head and neck. The compositions, etc., herein may prevent or treat cancers, including metastases, by allowing controlled release of high-molecular-weight fucan at a site somewhat distant from the target tumors by allowing effective concentrations of the high-molecular-weight fucan to reach the tumors and/or metastases by diffusion or even systemic transport. Some of these cancers are discussed further in the following paragraphs.

Prostate Cancer

Prostate cancer is a malignant tumor that arises in the cells lining the prostate gland. In the U.S., an estimated 200,000 patients will develop prostate cancer this year, and more than 30,000 will die of the disease. Prostate cancer has a death to new cases ratio of ~15%. The cancer may remain within the prostate, or it may spread to surrounding tissues or to distant sites (most often lymph nodes and bone). Usually prostate cancer spreads silently, producing symptoms only when it has progressed beyond the prostate. If prostate cancer has been diagnosed and treated during early stages, in some studies patients have had a 5-year survival rate of 94%.

Prostate cancer is often discussed as a disease of men over age 50. In fact, 80% of men with prostate cancer are 60 years of age and older. A man's chances of being diagnosed with prostate cancer during his lifetime are about 1 in 10, roughly the same as a woman's chances of having breast cancer. The number of reported new cases has risen dramatically in recent years as a result of improved tests that can detect the disease early in its development, often long before symptoms appear. The likelihood of developing prostate cancer in any given year increases with age but rises dramatically after age 50.

Current treatment options for prostate cancer depend upon the extent of disease progression, the patient's age and overall health. Elderly patients, who have only early stage cancer or who suffer from additional, more serious diseases, may be treated conservatively, whereas those whose cancer is advanced may undergo more aggressive treatment. Prostate cancer has been treated by various methods, including radiation therapy (external beam radiation or brachytherapy), hormone withdrawal or castration (surgical or chemical), anti-proliferative agents, surgery, and expectant therapy (that is, "watchful waiting"). No treatment guarantees an absolute cure, and some have considerable side effects.

Early stage prostate cancer (that is, the tumor is localized to the prostate) may be treated with "watchful waiting". Surgery for prostate cancer has been recommended for patients whose overall health has been otherwise good and the tumor is confined to the prostate gland. A common treatment for localized cancer of the prostate in men under the age of 70 has been radical prostatectomy (that is, surgical removal of the prostate).

Patients whose cancer is localized in the prostate area are commonly treated with external beam radiation (EBR). The radiation kills cancer cells and shrinks tumors. EBR accounts for less than 20% of localized prostate cancer treatment, with approximately 50% of these patients experiencing post radiation recurrences of the disease. Combined with early stage prostate cancer detection and increased demand from patients, brachytherapy (i.e., local radiation therapy) use has been expected to grow. In 1995, only 2.5% of newly diagnosed patients were treated using brachytherapy. Brachytherapy involves the implantation of radioactive metal "seeds" in the prostate tumor.

Treatment for prostate cancer that has spread involves removal of the testicles or hormone therapy. Both are used to inhibit or stop the production of the testosterone that has been driving the cancer growth. Approximately 20% of all prostate cancer patients undergo hormone withdrawal therapy. Hormone therapies include goserelin acetate (Zoladex®) or leuprolide acetate (Lupron®). Anti-proliferative agents used to treat prostate cancer have included 5-fluorouracil.

Breast Cancer

In the U.S., breast cancer has been the most common cancer among women, with about 180,000 new cases diagnosed every year (male breast cancer accounts for about 5% of all diagnosed breast cancers). It has been surpassed only by lung cancer as a cause of death in women, and it has been responsible for approximately 50,000 deaths annually. An American woman has a one in eight (or about 13%) chance of developing breast cancer during her lifetime. Over the past decade, most reported breast cancers were small, primary (arising independently; not caused by a metastasis) tumors. Roughly 70% to 80% of newly diagnosed patients exhibited early-stage disease (Stage 1 or 2), and a majority had no involvement of the axillary (underarm) lymph nodes.

Most breast cancers are carcinomas (that is, malignant tumors that grow out of epithelial tissues). Less than 1% of breast cancers are sarcomas, or tumors arising from connective tissue, bone, muscle or fat. In addition, most breast cancers (about 75%) are ductal carcinomas, arising in the tissues that line the milk ducts. A much smaller number of cancers (about 7%) are found within the breast lobules and are called lobular carcinomas. Paget's disease (cancer of the areola and nipple) and inflammatory carcinoma account for nearly all other forms of breast cancer.

Breast cancer treatment has been complicated and depends on many factors. Two important factors are the type of tumor and the stage of progression. Tumor characteristics, in particular, help to separate individuals into two groups: (1) those who are at low risk of cancer recurrence and (2) those who are at high risk of cancer recurrence. Specific prognostic factors place patients in either of these groups. These factors include tumor size; presence of female sex hormone estrogen and progesterone (ER/PR) receptors; cellular growth cycle phase (whether tumor cells are actively dividing or are in "S-phase"); presence of a protein known as "her-2-neu protein"; tumor grade, an indicator of tumor cell differentiation or change; and, tumor ploidy, the number of sets of genetic material within tumor cells.

Treatment of primary disease without significant lymph node involvement has been by lumpectomy and radiotherapy. More significant lymph node involvement may warrant mastectomy and removal of auxiliary lymph nodes. At this stage the chance of metastasis and local recurrence has been high. Treatment of metastatic disease has been palliative, involving radiation therapy and chemotherapy, which are immunosuppressive, cytotoxic and leukopenia. Anti-proliferative agents including, for example, 5-fluorouracil, doxorubicin, methotrexate, and paclitaxel, have been approved for use against breast cancer.

Pancreatic Cancer

The pancreas is an organ of the digestive system located near the stomach and small intestine. It has two major functions: the production of enzymes and hormones. Cancers of the pancreas can occur in the exocrine (i.e., enzymes) pancreas (e.g., classic pancreatic adenocarcinomas) or can occur in the endocrine (i.e., hormones) pancreas.

Cancers of the exocrine pancreas are a very serious health issue. In the U.S., approximately 28,000 patients are diagnosed with pancreatic cancer, while about the same number die annually from this disease. Pancreatic cancer occurs equally in males and females. Due to difficulties in diagnosis, the intrinsic aggressive nature of pancreatic cancers, and the sparse systemic treatment options available, only approximately 4% of patients diagnosed with pancreatic adenocarcinoma live for 5 years after diagnosis. Pancreatic cancer has been the $5^{th}$ leading cause of cancer death, following breast, lung, colon, and prostate cancer.

The choice of treatment for pancreatic cancer depends largely on the stage of the tumor. Possible treatments include surgery, anti-proliferative agents, radiation, and biological therapy. Surgery has been usually reserved for Stage 1 patients whose cancer is deemed resectable. Sometimes a combination of therapies, such as radiation and anti-proliferative agent given before or after surgery, can increase a patient's chances of survival. Pancreatic cancer that is deemed unresectable (usually Stage II or later) may be treated using anti-proliferative agents in clinical trials. Anti-proliferative agents, such as, for example, gemcitabine or 5-fluorouracil have had some effect against pancreatic cancer and gemcitabine has been used as a palliative agent. Toxicities due to these anti-proliferative agents are discussed elsewhere herein. Radiation therapy has some effect against pancreatic cancer when used in combination with chemotherapy. Radiation therapy alone may subdue symptoms. This form of treatment has also been used in Stage II or later pancreatic cancers.

Bladder Cancer

In 1998, it was estimated that over 54,000 new cases of bladder cancer would be diagnosed in the U.S. and about 15,000 deaths would be attributed to the disease. Bladder cancer has been the fourth most common cancer among American men and the ninth most common cancer among American women. It occurs three times more frequently in men than in women. Primarily a disease of older men, bladder cancer has been a significant cause of illness and death. The risk of bladder cancer increases steeply with age (80% of cases occur in people older than 50 years), with over half of all bladder cancer deaths occurring after age 70. In white men over 65, the annual disease rate of bladder cancer has been approximately 2 cases per 1,000 persons; this contrasts with a rate of 0.1 cases per 1,000 persons under 65. During one's lifetime, the probability of developing bladder cancer has been greater than 3%; however, the probability of dying, from bladder cancer has been small (<1%). Bladder cancer rarely occurs in people who are younger than 40 years of age.

Recent studies suggest that certain genes and inherited metabolic abilities may play a role in bladder cancer. Transitional cell carcinoma (TCC) has been the most common form of bladder cancer. TCC usually occurs as a superficial (surface), papillary (wart-like), exophytic (outward-growing) mass upon a stalk-like base. In some cases, though, TCC may be attached on a broad base or it may appear ulcerated (within an indented lesion). Papillary TCCs often start out as areas of hyperplasia that later dedifferentiate or lose individual cell characteristics. Only about 10% to 30% of papillary TCCs develop into invasive cancers. By contrast, nonpapillary forms of TCC are more likely to become invasive. As noted, such TCCs may appear ulcerated or flat. Flat, nonpapillary TCC that has been made up of anaplastic epithelium has been classified as carcinoma in situ (CIS or TIS). The tissue of CIS contains cells that are large, have noticeable nucleoli (round body within a cell; involved in protein synthesis), and lack normal polarity.

The treatment of bladder cancer depends upon many factors. The most important of these factors are the type of tumor that is present and its stage. Common treatments include transurethral resection (TUR), electrosurgery, laser surgery, intravesical therapy, anti-proliferative agents, surgical therapy, cystectomy, and radiation therapy. Examples of anti-proliferative agents used to treat bladder cancer include, for example, 5-fluorouracil, cisplatin and methotrexate. Toxicities due to the anti-proliferative agents, 5-fluorouracil, cisplatin, and methotrexate, are discussed elsewhere herein.

Brain Cancer

Brain tumors are often inoperable and more than 80% of patients die within 12 months of diagnosis. Approximately 18,000 new cases of primary intracranial (brain) cancer are diagnosed each year in the U.S. This represents about 2 percent of all adult cancers. More than 50 percent of these are high-grade gliomas (i.e., glioblastoma multiform and anaplastic astrocytoma tumors). Patients with these tumors often suffer from severe disabilities such as motor dysfunction, seizures, and vision abnormalities.

Tumors that begin in brain tissue are known as primary brain tumors. Primary brain tumors are classified by the type of tissue in which they begin. The most common brain tumors are gliomas, which begin in the glial (supportive) tissue. Others include astrocytomas, brain stem gliomas, ependymomas and oligodendrogliomas.

Surgical removal of brain tumors has been recommended for most types and in most locations and should be as complete as possible within the constraints of preservation of neurologic function. An exception to this rule has been for deep-seated tumors, such as pontine gliomas, which are diagnosed on clinical evidence and are treated without initial surgery approximately 50% of the time. In many cases, however, diagnosis by biopsy is performed. Stereotaxic biopsy can be used for lesions that are difficult to reach and resect. Patients who have brain tumors that are either infrequently curable or unresectable should be considered candidates for clinical trials that evaluate radiosensitizers, hyperthermia, or interstitial brachytherapy used in conjunction with external-beam radiation therapy to improve local control of the tumor or for studies that evaluate new drugs and biological response modifiers.

Radiation therapy has a major role in the treatment of most tumor types and can increase the cure rate or prolong disease-free survival. Radiation therapy may also be useful in the treatment of recurrences in patients treated initially with surgery alone. Chemotherapy may be used before, during, or after surgery and radiation therapy. Recurrent tumors are treated with chemotherapy as well. Anti-proliferative agents used in the treatment of brain cancers include cisplatin. Examples of the toxicities associated with this anti-proliferative agent are discussed elsewhere herein.

Restenosis

Restenosis is a form of chronic vascular injury leading to vessel wall thickening and loss of blood flow to the tissue supplied by the blood vessel. This inflammatory disease can occur in response to vascular reconstructive procedures including any manipulation that relieves vessel obstruction. Thus, restenosis has been a major restrictive factor limiting the effectiveness of these procedures.

The present discussion comprises prevention or treatment of restenosis, for example by administering to a blood vessel a therapeutically effective amount of the combination of an oligonucleotide therapeutic and an anti-inflammatory agent. Suitable compositions include a polymeric carrier that can be surgically implanted at a restenosis site, or potential restenosis site, or can be injected via a catheter as a polymeric paste or gel. Suitable compositions may comprise high-molecular-weight fucans discussed herein.

Arthritis

Rheumatoid arthritis (RA) is a debilitating chronic inflammatory disease characterized by pain, swelling, synovial cell proliferation (pannus formation) and destruction of joint tissue. In the advanced stage, the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment has been recommended with disease modifying anti-rheumatic drugs (DMARDs) such as methotrexate, which drug is discussed elsewhere herein.

Crystal induced arthritis has been characterized by crystal induced activation of macrophages and neutrophils in the joints and is followed by excruciating pain for many days. The disease progresses so that the intervals between episodes gets shorter and morbidity for the patient increases. This disease has been generally treated symptomatically with non-steroidal anti-inflammatory drugs (NSAIDs) such as diclofenac sodium (Voltaren®). This anti-inflammatory agent has toxicities which include central nervous system toxicities such as dizziness and headache; dermatologic toxicities such as rash and pruritus; gastrointestinal toxicities such as exacerbated ulcerative colitis and Crohn's disease; genitourinary toxicities such as acute renal failure and renal papillary necrosis; hematologic toxicities such as agranulocytosis, leukopenia and thrombocytopenia; hepatic toxicities such as elevated liver transaminases and hepatitis; and, other toxicities such as asthma and anaphylaxis.

The present discussion comprises prevention or treatment of rheumatoid arthritis, for example via administering to a patient a therapeutically effective amount of an oligonucleotide therapeutic and optionally an anti-inflammatory agent. Suitable compositions include a polymeric carrier that can be injected into a joint as a controlled release carrier of the anti-inflammatory agent and microparticulates as controlled release carriers of the oligonucleotide therapeutic (which in turn has been incorporated in the polymeric carrier). Suitable compositions may comprise high-molecular-weight fucans discussed herein. Such polymeric carriers may take the form of polymeric microspheres, pastes or gels.

Inflammatory Conditions

The compositions, etc., herein may optionally inhibit or treat inflammatory conditions involving neutrophils for example comprising administering to a patient compositions containing an oligonucleotide therapeutic and an anti-inflammatory agent. Examples of such conditions include crystal-induced arthritis; osteoarthritis; non-rheumatoid inflammatory arthritis; mixed connective tissue disease; Sjögren's syndrome; ankylosing spondylitis; Behçet's syndrome; sarcoidosis; psoriasis; eczema; inflammatory bowel disease; chronic inflammatory lung disease; neurological disorders; and, multiple sclerosis. Some of these diseases are discussed further in the following paragraphs.

Chronic Inflammatory Skin Diseases (Including Psoriasis and Eczema)

Psoriasis is a common, chronic inflammatory skin disease characterized by raised, thickened and scaly lesions which itch, burn, sting and bleed easily. While these diseases have cellular proliferation and angiogenic components in later stages of the disease, patients often have accompanying arthritic conditions. Symptoms may be treated with steroidal anti-inflammatory agents such as prednisone or anti-proliferative agents such as methotrexate, which agents are discussed elsewhere herein. The compositions herein may also be used to inhibit or otherwise treat and/or prevent chronic inflammatory skin diseases, for example psoriasis and/or eczema.

The following provides some additional representative examples of inflammatory diseases that can be treated with compositions discussed herein, include, for example, arterial embolization in arteriovenous malformations (vascular malformations); menorrhagia; acute bleeding; central nervous system disorders; and, hypersplenism; inflammatory skin diseases such as psoriasis; eczematous disease (atopic dermatitis, contact dermatitis, eczema); immunobullous disease; and, inflammatory arthritis which includes a variety of conditions including rheumatoid arthritis, mixed connective tissue disease, Sjögren's syndrome, ankylosing spondylitis, Behçet's syndrome, sarcoidosis, crystal induced arthritis and osteoarthritis (all of which feature inflamed, painful joints as a prominent symptom).

Ischemia

Ischemia or ischaemia involves a restriction in blood supply, which may include a shortage of supply of oxygen, glucose and other components required for proper tissue function, resulting in damage and/or dysfunction of tissue. Ischemia can cause severe problems. For example, tissues can become anoxic, necrotic, and clots can form. Various attempts have been made to prevent and/or treat ischemia. For example, restoration of blood flow, or reperfusion. Restoration of blood, however, involves the reintroduction of oxygen, which can cause additional damage due to the production of free radicals, resulting in reperfusion injury. Reperfusion injury can cause severe problems. The compositions herein may be used to inhibit or otherwise treat and/or prevent, ischemia, and/or reperfusion injury.

Endotoxemia

Endotoxemia is the presence of endotoxins in the blood. Endotoxemia can cause severe problems. For example, endotoxemia can lead to septic shock. The compositions herein may be used to inhibit, or otherwise treat and/or prevent, endotoxemia.

Keloid Scarring

Keloid trait causes wounds to heal with raised scars. Keloid traits' raised scars involve abnormal fibrous scarring. Keloid trait causes severe problems, for example, pain and disfigurement. The compositions herein may be used to inhibit, or otherwise treat and/or prevent, keloid trait and its resulting raised scars.

Keloid (keloid scar) is a type of scar that expands in growths over normal skin. Keloids involve abnormal collagen growth, including type I and type III collage abnormal growth. Keloids cause severe problems, for example, pain, itchiness, and if infected may ulcerate. Attempts have been made to treat or prevent keloids including the use of surgery, dressings, steroid injections and laser therapy. The compositions herein may be used to inhibit, or otherwise treat and/or prevent, keloids.

Dermatitis

Dermatitis includes inflammation of the skin including atopic dermatitis and contact dermatitis. For example, contact dermatitis involves localized rash and/or irritation of the skin following contact of the skin with a foreign substance. For example, atopic dermatitis is a chronically relapsing, pruritic skin disease. Atopic dermatitis is sometimes called prurigo Besnier, neurodermitis, endogenous eczema, flexural eczema, infantile eczema, childhood eczema and prurigo diathsique. Eczema is a disease in a form of dermatitis. Other types of dermatitis include spongiotic dermatitis, seborrhoeic dermatitis (dandruff), dyshidrotic dermatitis (pompholyx), urticaria, vesicular dermatitis (bullous dermatitis), and popular urticaria. Dermatitis can cause severe problems. For example, dry skin, skin rashes, skin edema, skin redness, skin itchiness, skin crusting, cracking, blistering, oozing and bleeding. Attempts have been made to treat or prevent dermatitis including the use of corticosteroids and coal tars. The compositions herein may be used to inhibit, or otherwise treat and/or prevent, dermatitis including atopic dermatitis, eczema, contact dermatitis, spongiotic dermatitis, seborrhoeic dermatitis, dyshidrotic dermatitis, urticaria, vesicular dermatitis, and popular urticaria.

Rosacea

Rosacea is a chronic disease or condition typically characterized by facial erythema. Rosacea can cause severe problems. For example, rosacea typically begins as redness on the forehead, nose or cheeks and can also cause redness on the neck, ears, scalp and chest. For example, rosacea can cause additional symptoms including telangiectasia, papules, pustules, painful sensations, and in advanced cases rhinophyma (red lobulated nose) may develop. Rosacea subtypes include erythematotelangiectatic rosacea, papulopustular rosacea, phymatous rosacea, and ocular rosacea. Attempts have been made to treat or prevent rosacea including the use of anti-inflammatories and antibiotics. The compositions herein may be used to inhibit, or otherwise treat and/or prevent, rosacea including its erythematotelangiectatic, papulopustular, rosacea and ocular subtypes.

Medical Device, Medical Material, Combination, and Pharmaceutical Products

The discussion herein also provides medical devices, medical materials, combination, and pharmaceutical products, comprising compositions as discussed herein in a medical device, medical material, combination product or pharmaceutically acceptable container. The products can also include a notice associated with the container, typically in a form prescribed by a governing agency regulating the manufacture, use, or sale of medical devices, medical materials, combination, and pharmaceuticals or biopharmaceuticals, whereby the notice is reflective of approval by the agency of the compositions, such as a notice that a high-molecular-weight fucan has been approved as an anti-proliferative agent or anti-inflammatory agent, e.g., for human or veterinary administration to treat proliferative diseases or inflammatory diseases (such as, for example, inflammatory arthritis, restenosis, surgical adhesions, psoriasis and peritonitis). Instructions for the use of the high-molecular-weight fucan herein may also be included. Such instructions may include information relating to the dosing of a patient and the mode of administration.

The present application is further directed to methods of making the various elements of the high-molecular-weight fucan, systems etc., discussed herein, including making the compositions themselves, as well as to methods of using the same, including for example treatment of the conditions, diseases, etc., herein.

The present application further comprises medical devices, medical materials, medical combination products, and pharmaceutical products for treatment of fibrous adhesions, arthritis, psoriasis or other diseases as desired comprising high-molecular-weight fucans presented herein. The materials, etc., can be used in a medicament for treating fibrous adhesions, such as a surgical adhesions, arthritis, psoriasis or other diseases as desired. Also provided are methods of manufacturing and using such medicaments able to reduce symptoms associated with at least one of fibrous adhesions, arthritis, and psoriasis in a patient including a human patient, comprising combining a pharmaceutically effective amount of a fucan such as fucoidan as discussed herein with a pharmaceutically acceptable excipient or buffer.

The following Examples provide exemplary discussions of certain embodiments herein but the disclosure and claims are not limited thereto.

Example 1: Chemical Structural Modification

An exudate-extract was obtained from *Laminaria Hyperborea*. The exudate-extract was filtered and small molecules were removed by tangential flow filtration (TFF) over a 100 kDa filter. A sample of the resulting retentate was lyophilized to obtain otherwise unmodified sample A. The resulting retentate was brought to 0.25 M NaOH by addition of 10 M NaOH solution and left at room temperature for 16 hours. The resulting sample was then centrifugally filtered over a 50 kDa filter and the resulting retentate collected and lyophilized to obtain base-treated sample B. Both unmodified sample A and base-treated sample B were analyzed by proton nuclear magnetic resonance spectroscopy ($^1$H-NMR) and the resulting $^1$H-NMR spectrum are shown in FIG. 9A.

Figure 9A:
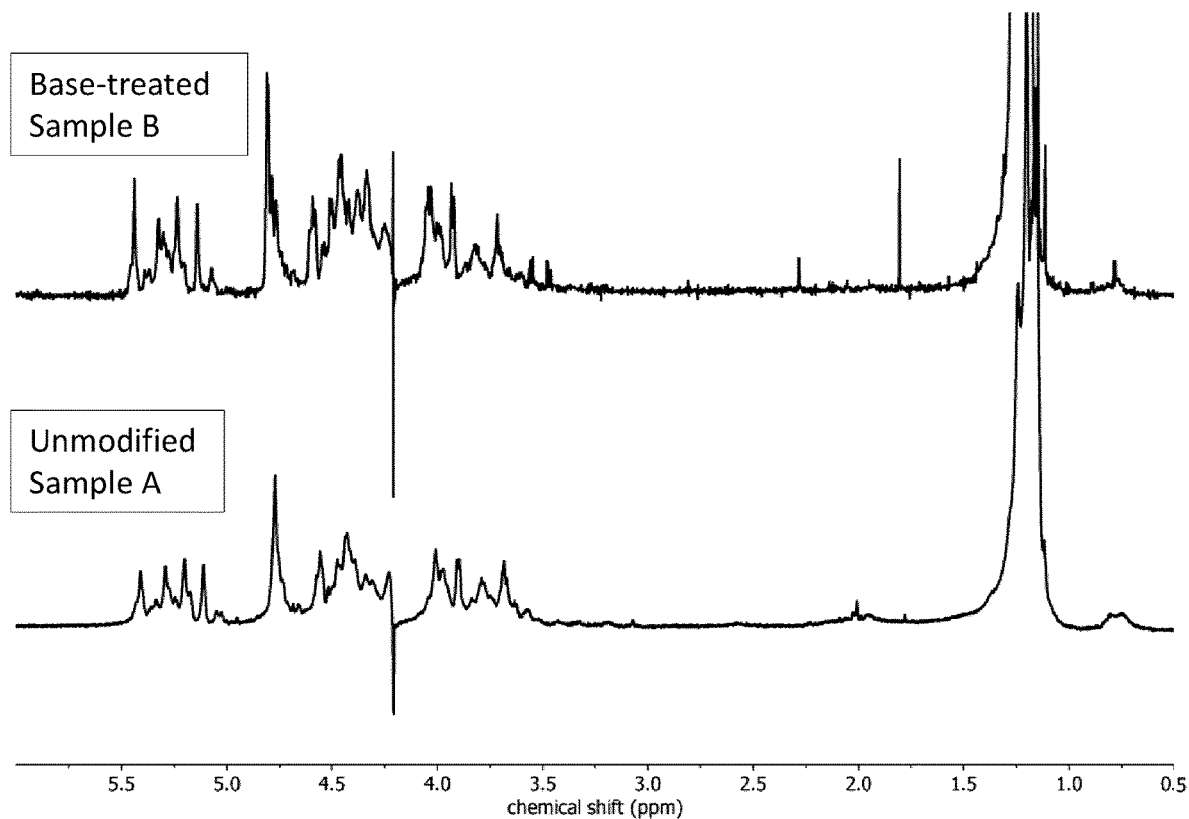
FIG. 9A depicts NMR results demonstrating that certain fucans treated according to methods herein undergo structural changes to the fucans.

FIG. 9A demonstrates the chemical structural modification of the fucan accomplished, the broad peak with a chemical shift about 2.0 ppm that is present in the unmodified sample A is not present in the base-treated sample B.

Unmodified sample A and base-treated/modified sample B were further analyzed by 2D $^1$H-$^{13}$C heteronuclear multiple quantum coherence (HMQC). The HMQC spectra, shown in FIG. 9B, were acquired at 70° C. with solvent signal suppression on a 600 MHz spectrometer equipped with 5-mm cold probe. A high number of scans of the HMQC spectra were acquired in the range from 10-30 ppm in the carbon dimension in 8 increments of 256-512 scans each; such scans were combined to create the spectra in FIG. 9B.

Figure 9B:
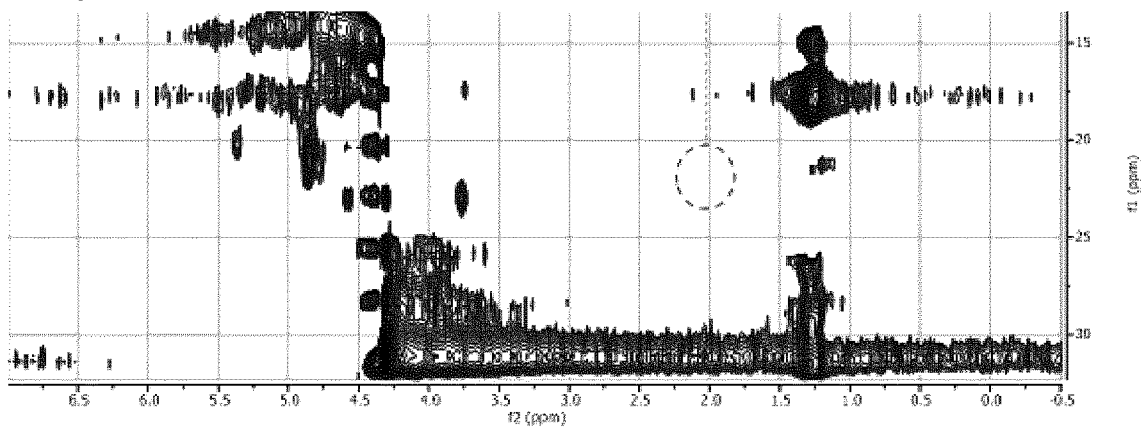
FIG. 9B depicts 2-D NMR results demonstrating that certain fucans treated according to methods herein undergo chemical structural changes to the fucans.
Figure 9B:
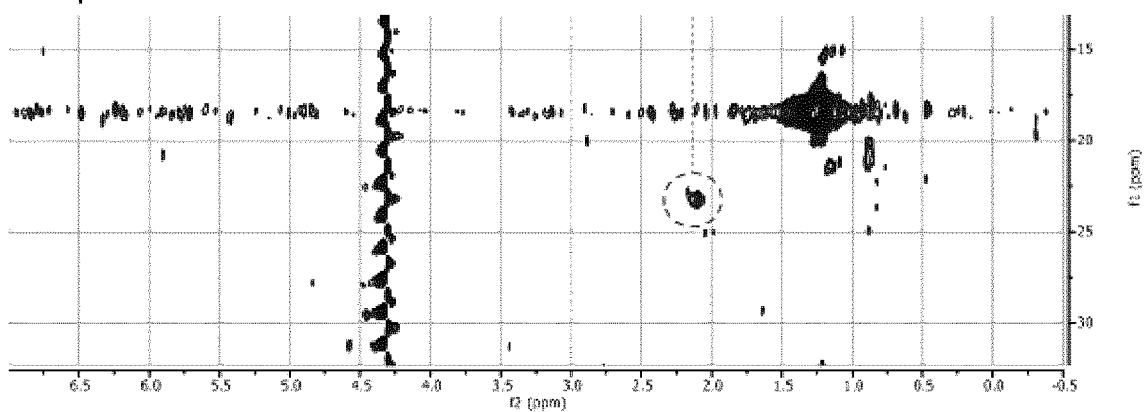

The HMQC spectra for unmodified sample A has a cross-peak corresponding to O-acetyl groups, indicated by the signal circled in FIG. 9B. This cross-peak is not present in the spectra for base-treated sample B. This demonstrates the removal of acetyl groups from the fucan, and thus chemical structural modification of the fucan in base-treated sample B by the NaOH treatment.

Example 2: Tangential Flow Filtration

A high-molecular-weight fucan may be obtained by tangential flow filtration. A broad distribution starting fucan is dissolved in distilled water at 50 mg/mL. In this example, the broad distribution fucan is diafiltered against distilled water over a 100 kDa molecular weight cut-off (MWCO) tangential flow filter (TFF) cassette for 4 diavolumes to remove unwanted lower molecular weight components and the retentate of the TFF process is collected comprising the high-molecular-weight fucan. The diafiltration may be accomplished with any desired MWCO TFF filter, for example a 50 kDa, 70 kDa, 100 kDa, 300 kDa, 500 kDa and 1000 kDa MWCO TFF cassette. The resulting high-molecular-weight fucan has a higher average molecular weight than the broad molecular weight distribution starting fucan.

Example 3: Sequential Tangential Flow Filtration Segmentation

An input broad molecular weight distribution starting fucoidan having a weight average molecular weight of 365.6 kDa and Polydispersity index (PDI)=3.58 that had been pre-filtered through a 0.22 micron filter was provided. A TFF filter cassette of 100 kDa MWCO supplied by Pall of Port of Washington was employed as the higher MWCO TFF cassette and a 50 kDa TFF cassette supplied by Pall of Port of Washington employed as the lower MWCO TFF cassette. The process was repeated for the following TFF cassette pairs: a TFF filter of MWCO 300 kDa supplied by Millipore of Burlington, Mass. and a TFF filter of MWCO 100 kDa supplied by Pall of Port of Washington, a TFF filter of MWCO 50 kDa supplied by Pall of Port of Washington and a filter of 30 kDa supplied by Pall of Port of Washington, a TFF filter of 30 kDa supplied by Pall of Port of Washington and a TFF filter of 10 kDa supplied by Pall of Port of Washington. The cassettes were all of the Polyethersulfone (PES) type.

After sequential tangential low filtration as discussed above, the various obtained fucans, including high-molecular-weight fucans comprising high-molecular-weight segments of the starting fucan molecular weight distribution, were analyzed using gel permeation chromatography (GPC). The results are shown in Table 1 below.

Example 4: Cation Augmented Tangential Flow Filtration

A broad molecular weight distribution input starting fucoidan composition in a starting solution having a weight average molecular weight of 436.4 kDa with a polydispersity index (PDI) of 3.24 that had been pre-filtered through a 0.22 micron filter was provided. Choline, a biocompatible water-soluble quaternary ammonium salt, was selected as the chemical additive. Choline was added in a 1:2 choline: fucoidan mass ratio to the pre-filtered starting solution and the resulting mixture stirred until the choline was dissolved. The choline may or may not bind to the sulfate sites on the fucoidan molecules. In a first TFF process, the choline treated-fucoidan solution was then subjected to tangential flow filtration over a 300 kDa filter cassette to obtain a first retentate comprising a choline bound high-molecular-weight fucoidan, being a choline-treated retentate. During this first choline-augmented TFF process, the choline treated-fucoidan solution was diafiltered with four diavolumes of 1% w/v choline flush solution. The choline-treated retentate of the first TFF process was collected and subjected to a second TFF process to replace the choline cations with sodium cations.

The second TFF process, being a decholinating TFF process, comprised diafiltering the choline-treated retentate of the first TFF process over a 50 kDa filter cassette while treating the retentate with NaCl to replace the choline cations with sodium cations. In this example, the choline-treated retentate was diafiltered with 4 volumes of 2 M NaCl to remove the choline additive from the high-molecular-weight fucoidan. The decholinated retentate of this second TFF process was then diafiltered with deionized water until the conductivity of the permeate had dropped to below 5 mS/cm to indicate the removal of excess NaCl. After cation augmented TFF as discussed above, samples of the various retentates in the process comprising the high-molecular-weight fucan were analyzed using gel permeation chromatography (GPC). The results are shown in Table 2 below.

TABLE 1

| | TFF segmentation of fucoidan | | | | | | | |
|---|---|---|---|---|---|---|---|---|
| | GPC PRT (Mins) | PMW (kDa) | WAMW (kDa) | NAMW (kDa) | % dist. MW >100 kDa | % dist. MW >200 kDa | % dist. MW >500 kDa | PDI |
| Input | 25.51 | 299.6 | 365.6 | 102.2 | 76.3 | 57.2 | 23.1 | 3.58 |
| MWCO of TFF filter pairs (kDa) | | | | | | | | |
| 300-100 | 25.62 | 278.3 | 394.2 | 151.9 | 83.5 | 63.3 | 24.9 | 2.60 |
| 100-50 | 27.96 | 59.8 | 125.1 | 42.6 | 37.3 | 17.4 | 3.3 | 2.94 |
| 50-30 | 30.33 | 12.6 | 20.6 | 9.8 | 1.6 | 0.3 | 0.0 | 2.11 |
| 30-10 | 34.22 | 1.0 | 2.1 | 1.2 | — | — | — | 1.66 |

TABLE 2

Cation-augmented TFF segmentation of fucoidan

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input MWCO of TFF filter retentate (kDa) | 24.67 | 436.4 | 490.7 | 151.3 | 82.3 | 66.1 | 34.8 | 3.24 |
| 300 | 24.71 | 423.6 | 525.5 | 206.7 | 88.5 | 72.6 | 37.3 | 2.54 |
| 100 | 24.10 | 639.8 | 740.7 | 411.0 | 97.9 | 90.6 | 59.1 | 1.80 |

Example 5: Centrifugal Precipitation

Figure 10:
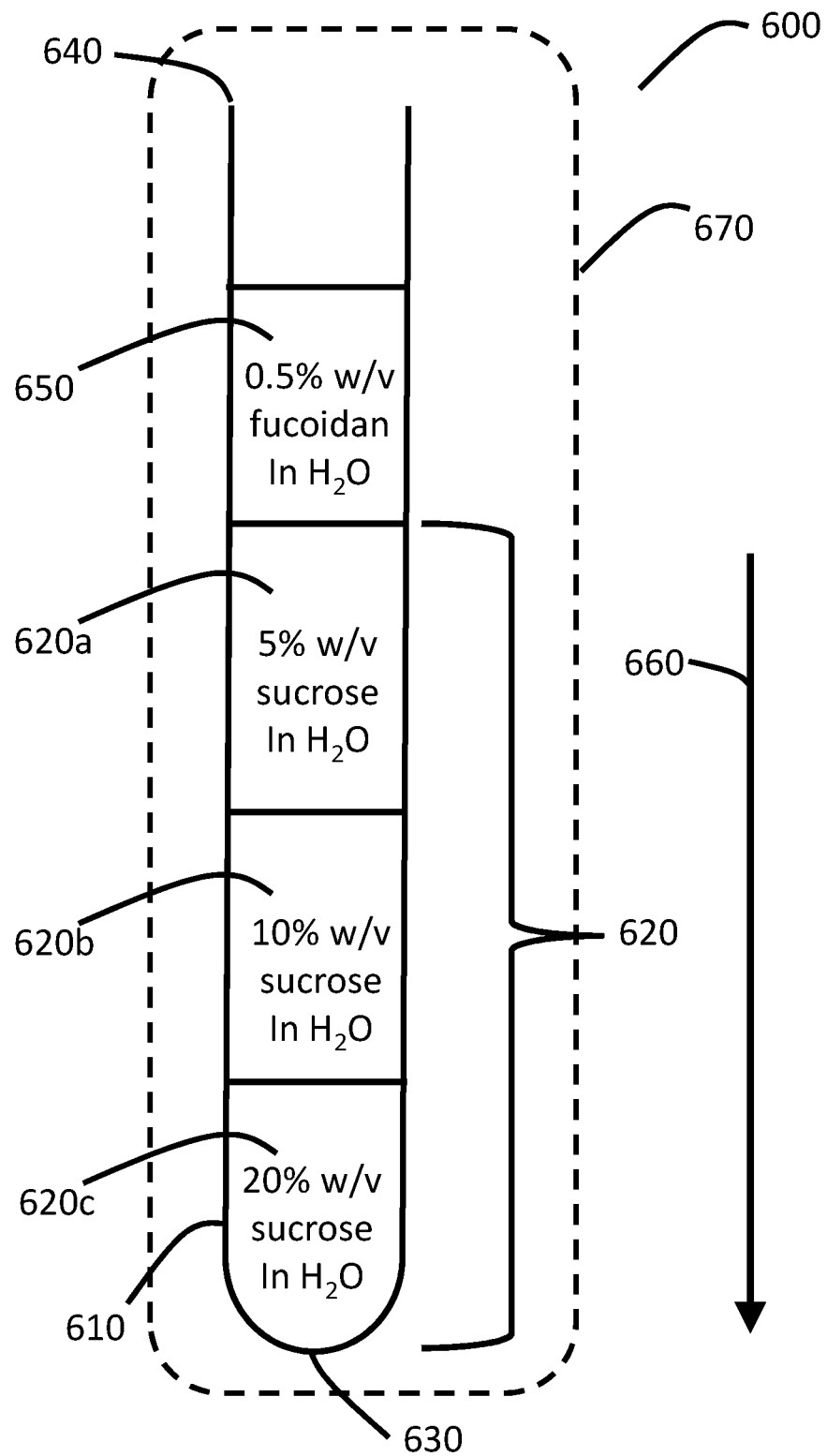
FIG. 10 shows an exemplary system for the centrifugal precipitation of a high-molecular-weight fucan from a starting fucan composition using a multi-segment sucrose barrier, the starting fucan having a broad molecular weight distribution.

A starting solution containing 0.5% w/v starting fucoidan composition that had been pre-filtered through a 0.22 μm pre-filter was provided. A step gradient of 20%, 10%, and 5% w/v sucrose in water was created in a centrifuge tube, with 5% layer being the topmost layer and the 20% layer being in the bottom of the centrifuge tube. The 0.5% starting solution containing the starting fucoidan composition was then layered on top of the 5% w/v sucrose layer. The resulting layer structure is shown in FIG. 10. The tube with these four layers was then centrifuged at 190,000 gravities (g) for 6 hours. The supernatant solution was decanted and the precipitate remaining in the centrifuge tube, containing the desired high-molecular-weight fucan, was re-dissolved in water. The re-dissolved high-molecular-weight fucan was then analyzed by gel permeation chromatography (GPC). The results are shown in Table 3 below.

TABLE 3

Centrifugal precipitation of fucoidan using a 5%-10%-20% sucrose barrier

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input | 24.57 | 471.7 | 590.1 | 200.6 | 87.4 | 72.3 | 40.3 | 2.94 |
| Re-dissolved fucoidan precipitate | 22.95 | 1472.9 | 1113.0 | 492.3 | 98.2 | 91.0 | 69.1 | 2.26 |

Example 6: Gel Electrophoresis-Extraction

A starting fucoidan composition with a broad molecular weight distribution was provided. The starting fucoidan composition was dissolved at 50 mg/mL, pre-filtered through a 0.22 micron filter and loaded onto a 0.5% agarose gel cast from 380 mL of agarose. The loaded gel was submerged in a running buffer of 40 mM tris-acetate 1 mM EDTA, also known as TAE buffer. A voltage of 90 V was applied across the buffer for 50 minutes with the anode proximate the starting fucoidan composition well. This allowed the fucoidan to separate by mass to charge ratio through the gel. For visualization purposes, the gel was stained with methylene blue, a dye known to stain fucoidan. The agarose gel was then cut in 1 cm wide segments parallel to the well, starting 1 cm from the well. The segments of the gel were agitated in distilled water to extract the fucoidan segments from the gel by shaking the mixture.

The electrophoresis-extracted fucoidan segments, potentially comprising high-molecular-weight fucoidans, were analyzed by gel permeation chromatography (GPC). The results are shown in Table 4 below.

TABLE 4

GPC results of the electrophoresis-based separation of pre-filtered starting fucoidan across agarose gel with TAE buffer.

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input Distance of gel segment from well | 24.67 | 462.6 | 581.3 | 170.9 | 86.7 | 73.0 | 40.8 | 3.40 |
| 1-2 cm | 25.07 | 349.4 | 619.9 | 81.33 | 71.3 | 55.9 | 30.7 | 7.62 |
| 2-3 cm | 25.16 | 327.8 | 362.0 | 118.2 | 76.2 | 56.7 | 23.9 | 3.06 |

TABLE 4-continued

GPC results of the electrophoresis-based separation of pre-filtered starting fucoidan across agarose gel with TAE buffer.

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| 3-4 cm | 25.47 | 263.6 | 288.4 | 103.7 | 70.9 | 48.8 | 16.7 | 2.78 |
| 4-5 cm | 25.58 | 242.7 | 279.1 | 66.0 | 62.8 | 42.2 | 14.9 | 4.23 |

Example 7: Membrane Dialysis

A 5% w/v starting solution containing a starting fucoidan composition that had been pre-filtered through a 0.22 micron filter was provided. The starting solution was placed in a cellulose acetate dialysis tubing of nominal molecular weight cutoff 300 kDa. The dialysis tubing was sealed and placed in a container with 20 liters of deionized water. The deionized water was replaced with fresh deionized water every 12 hours to ensure continuous diffusion across the membrane pores. The dialysis process was allowed to continue for about 5 days.

The pre-filtered starting fucoidan composition and the post-dialysis, high-molecular-weight fucoidan in the dialysis tube were both analyzed using gel permeation chromatography (GPC). The results are shown in Table 5 below.

TABLE 5

GPC results of the dialysis of fucoidan against deionized water across a 300 kDa membrane.

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input | 24.57 | 471.7 | 590.1 | 200.6 | 87.4 | 72.4 | 40.3 | 2.94 |
| Dialyzed Fucoidan | 24.29 | 599.1 | 777.0 | 374.5 | 96.8 | 88.6 | 57.0 | 2.07 |

Example 8: Selective Precipitation

A starting fucoidan composition that had been pre-filtered through a 0.22 μm pre-filter and desalted via diafiltering with deionized water over a 100 kDa TFF cassette to remove unwanted low molecular weight salts that may interfere with the precipitation process was provided. A series of identical starting solutions of the prefiltered and desalted starting fucoidan in distilled water were prepared. The solvent compositions were brought up to different pre-determined concentrations of ethanol. This prepared the different solvent environments for the precipitation of the fucoidan from the solution compositions identified in Table 6 below. A minimal amount of an ionic agent in the form of NaCl was added to each solution composition to initiate the precipitation of fucoidan from the solution. The mixes of precipitate and solution composition were centrifuged at 2300 gravities for 10 minutes. The liquid supernatant was decanted in each case and the solid fucoidan collected.

The solid fucoidan were re-dissolved in distilled water and analyzed by gel permeation chromatography. The results are shown in Table 6 below.

TABLE 6

Selective precipitation of fucoidan using ethanol as precipitating solvent

| % Ethanol in the fucoidan solution | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| 40 | 24.85 | 394.1 | 447.0 | 133.5 | 76.6 | 62.5 | 31.3 | 3.35 |
| 50 | 25.96 | 182.1 | 347.9 | 149.2 | 80.8 | 53.9 | 20.3 | 2.33 |
| 60 | 25.43 | 263.1 | 335.5 | 119.1 | 73.9 | 51.9 | 20.0 | 2.82 |
| 70 | 24.91 | 376.1 | 382.6 | 117.2 | 75.7 | 56.8 | 25.4 | 3.26 |

Example 9: Anionic Adsorption

A starting solution containing about 500 mg of a broad molecular weight distribution desalted starting fucoidan was recirculated on about 14 mL of DEAE-Sepharose® resin for about 16 hours to bind the low molecular weight fucoidan to the active sites on the resin. After about 16 hours the recirculating solution was collected. This separated the high-molecular-weight fucoidan from the low molecular weight fucoidan that had bonded to the resin. 10% w/v NaCl was then recirculated on the resin for 4 hours to displace the low molecular weight fucoidan from the resin. The fucoidan rich-salt solution was then collected and desalted over a 5 kDa centrifugal filter to separate the collected low molecular weight fucoidan from the unwanted salt. GPC was performed on the desalted starting fucoidan, the high-molecular-weight fucoidan not adsorbed during the ion exchange process, and the low molecular weight fucoidan extracted from the resin. The results are shown in Table 7 below.

TABLE 7

| | \multicolumn{7}{c}{Anion exchange segmentation of fucoidan: DEAE-Sepharose as resin} | | | | | | |
|---|---|---|---|---|---|---|---|---|
| | GPC PRT (Mins) | PMW (kDa) | WAMW (kDa) | NAMW (kDa) | % dist. MW >100 kDa | % dist. MW >200 kDa | % dist. MW >500 kDa | PDI |
| Input | 24.57 | 462.4 | 576.6 | 198.0 | 87.1 | 71.9 | 39.6 | 2.91 |
| Fucoidan not adsorbed | 24.20 | 601.3 | 844.5 | 391.4 | 96.8 | 90.9 | 60.5 | 2.16 |
| Fucoidan adsorbed | 25.82 | 193.6 | 245.8 | 119.2 | 73.0 | 43.8 | 10.7 | 2.06 |

Example 10: Anionic Adsorption

A starting solution containing about 1 g of a broad molecular weight distribution desalted fucoidan was mixed with about 10 g Amberlyst® A26 resin for about 16 hours to bind the low molecular weight fucoidan to the active sites on the resin. The solution containing the high-molecular-weight fucoidan was subsequently separated from the resin by decanting. 20% w/v NaCl was then mixed with the resin for about 4 hours to displace the low molecular weight fucoidan from the resin. The fucoidan rich salt solution was then separated from the resin and desalted over a 5 kDa centrifugal filter to separate the collected low molecular weight fucoidan from the unwanted salt. GPC was performed on the desalted starting fucoidan, the high-molecular-weight fucoidan not adsorbed during the ion exchange process, and the low molecular weight fucoidan extracted from the resin. The results are shown in Table 8 below.

TABLE 8

| | \multicolumn{7}{c}{Anion exchange separation of fucoidan: Amberlyst™ A26 OH} | | | | | | |
|---|---|---|---|---|---|---|---|---|
| | GPC PRT (Mins) | PMW (kDa) | WAMW (kDa) | NAMW (kDa) | % dist. MW >100 kDa | % dist. MW >200 kDa | % dist. MW >500 kDa | PDI |
| Input | 25.02 | 517.7 | 536.9 | 148.2 | 82.7 | 67.7 | 38.1 | 3.62 |
| Fucoidan not adsorbed | 24.73 | 625.8 | 867.4 | 463.1 | 98.7 | 93.0 | 62.6 | 1.87 |
| Fucoidan adsorbed | 27.30 | 112.4 | 172.3 | 86.4 | 58.0 | 25.4 | 4.7 | 2.00 |

Example 11: Anionic Adsorption

A starting solution containing about 1 g of a broad molecular weight distribution desalted fucoidan was mixed with about 10 g of three different resins, being Amberlyst® A26 OH⁻, Ambersep® 900 OH⁻, and Lewatit® VPOC 1065 in three separate containers. The solution-resin mixtures were incubated for about 16 h to bind the low molecular weight fucoidan to the active sites on the resin. The solution containing the high-molecular-weight fucoidan was subsequently separated from the resin by decanting. The pores of the Amberlyst® and Ambersep® product had quaternary amine groups while the pores of the Lewatit product had primary benzylamine groups. The first two products were strongly basic anion exchange resins, while the third was a weakly basic anion exchange resin. The fucoidan not adsorbed during the ion-exchange process were then analyzed by GPC. The results are shown in Table 9 below.

TABLE 9

Anion exchange separation of fucoidan: comparison of fucoidans prepared by recirculation on 3 resins.

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input | 24.66 | 461.9 | 521.5 | 151.8 | 83.0 | 67.3 | 36.5 | 3.44 |
| Resin used | | | | | | | | |
| Ambersep® 900 OH⁻ | 24.51 | 513.0 | 609.1 | 323.6 | 96.1 | 85.5 | 47.3 | 1.88 |
| Amberlyst® A26 OH⁻ | 24.58 | 489.8 | 591.0 | 309.5 | 95.6 | 83.5 | 45.1 | 1.91 |
| Lewatit® VPOC 1065 | 24.54 | 501.2 | 585.6 | 219.6 | 89.5 | 75.3 | 42.4 | 2.67 |

Example 12: Anionic Adsorption

A starting solution containing about 1 g of a broad molecular weight distribution desalted fucoidan was mixed with about 10 g Ambersep® 900 OH⁻ for up to 53 hours. The fucoidan in the mixture not adsorbed during the ion-exchange process were then analyzed by GPC at various time points during the anion adsorption process. The results are shown in Table 10 below.

Example 13: Anionic Adsorption

A starting solution containing about 1 g of the broad molecular weight distribution desalted fucoidan was mixed with various amounts of Ambersep® 900 OH⁻ for about 16 hours to bind the low molecular weight fucoidan to the active sites on the resin. The solution containing the high-molecular-weight fucoidan was subsequently separated from the resin by decanting. The fucoidan not adsorbed

TABLE 10

Anion exchange separation of fucoidan: comparison of anion exchange times

| | GPC PRT (Mins) | PMW (kDa) | WAMW (kDa) | NAMW (kDa) | % dist. MW >100 kDa | % dist. MW >200 kDa | % dist. MW >500 kDa | PDI |
|---|---|---|---|---|---|---|---|---|
| Input | 26.71 | 624.2 | 955.9 | 339.9 | 95.2 | 84.6 | 56.3 | 2.81 |
| Ion exchange time (hours) | | | | | | | | |
| 1 | 26.66 | 642.4 | 1049.2 | 386.0 | 96.6 | 87.3 | 59.5 | 2.72 |
| 4 | 26.42 | 756.4 | 1151.7 | 470.9 | 98.2 | 91.7 | 65.5 | 2.45 |
| 24 | 26.33 | 801.9 | 1205.2 | 589.9 | 99.5 | 95.9 | 72.1 | 2.04 |
| 53 | 26.25 | 843.6 | 1257.9 | 656.9 | 99.8 | 97.5 | 75.6 | 1.91 | during the ion-exchange process were then analyzed by GPC. The results are shown in Table 11 below.

TABLE 11

Anion exchange separation of fucoidan: comparison of different fucoidan to resin ratios

| | GPC PRT (Mins) | PMW (kDa) | WAMW (kDa) | NAMW (kDa) | % dist MW >100 kDa | % dist. MW >200 kDa | % dist. MW >500 kDa | PDI |
|---|---|---|---|---|---|---|---|---|
| Input | 24.66 | 442.4 | 498.5 | 146.3 | 82.4 | 66.1 | 34.8 | 3.41 |
| Mass ratio of Fucoidan:resin | | | | | | | | |
| 1:1 | 24.51 | 491.1 | 548.1 | 203.2 | 87.6 | 72.0 | 39.0 | 2.70 |
| 1:5 | 24.48 | 500.9 | 633.9 | 306.6 | 95.3 | 82.9 | 46.6 | 2.07 |
| 1:10 | 24.41 | 523.8 | 688.1 | 376.4 | 98.0 | 88.8 | 51.9 | 1.83 |

Example 14: Preparative Gel Permeation Chromatography

A starting fucoidan composition with a broad molecular weight distribution is provided. The starting fucoidan composition is dissolved at 10 mg/mL in 60 mL 0.1 M sodium nitrate. 20 mL of the starting solution containing the starting fucoidan composition is pumped at 40 mL/min through each of a 50 mm inner diameter, 250 mm length column containing Sepax® SRT-10/10C SEC-1000, Agilent® PL Aquagel®-OH MIXED-H and TSKGel® G4000SW respectively, all of which contain modified silica-hydrophilic bonded phase gel media. Elution is carried out at the same flow rate using 0.1 M sodium nitrate. After 5 minutes of elution, 40 mL aliquots are collected until a total of 1000 mL, or 25 aliquots, have been collected. The molecular weight distribution of a sample of each aliquot is measured by analytical GPC. Aliquots containing weight average molecular weights between 200 kDa and 600 kDa are pooled. Aliquots containing weight average molecular weights between 600 kDa and 1000 kDa are pooled. Aliquots containing weight average molecular weights between 1000 kDa and 1400 kDa are pooled. Aliquots containing weight average molecular weights between 1400 kDa and 1800 kDa are pooled. The rest of the aliquots are discarded. Each pooled preparative GPC aliquot composition contains a desired high-molecular-weight fucan.

Example 15: Preparative Gel Permeation Chromatography

A starting fucoidan composition with a broad molecular weight distribution is provided. The starting fucoidan composition is dissolved at 10 mg/mL in 60 mL 0.1M sodium nitrate. 20 mL of the starting solution containing the starting fucoidan composition is pumped at 40 mL/min through each of a 50 mm inner diameter, 250 mm length column containing Waters® HSPgel AQ MB-H, PSS® Suprema® Combination Ultrahigh and TSKGel® GMPWXL respectively, all of which contain hydroxylated polymethacrylate-based gel media. Elution is carried out at the same flow rate using 0.1M sodium nitrate. After 5 minutes of elution, 40 mL aliquots are collected until a total of 1000 mL, or 25 aliquots, have been collected. The molecular weight distribution of a sample of each aliquot is measured by analytical GPC. Aliquots containing at least 90% of their molecular weight distribution above 100 kDa, at least 80% of their molecular weight distribution above 200 kDa and/or at least 50% of their molecular weight distribution above 500 kDa are pooled. The rest of the aliquots are discarded. Each pooled preparative GPC aliquot composition contains a desired high-molecular-weight fucan.

Example 16: Preparation of Low and High-Molecular-Weight Fucans

The methods discussed herein may be used, combined, modified and permuted in any manner to obtain high-molecular-weight fucans.

Twenty fucans, some with high and some with low molecular weights, were prepared from feedstock/starting fucan compositions having broad molecular weight distributions to evaluate the efficacy of high and low molecular weight fucans in medical and surgical applications. The twenty fucans are hereafter referred to as fucan 1 to fucan 20. Fucan 1 to fucan 5 were light brown solids. Fucan 6, fucan 8 to fucan 15 and fucan 17 were white solids. The preparation of low-molecular weight fucans, being fucan 1 to fucan 6, involved numerous different methodologies. Fucan 3 was extracted from brown seaweed and found to be a low-molecular weight fucan. Fucan 2 was obtained from FMC BioPolymer® and found to be a low-molecular weight fucan. Fucan 1 and fucan 5 were obtained by methods discussed in example 3, using MWCO TFF filters under 100 kDa. Fucan 4 was obtained by methods discussed in example 10. Fucan 6 was obtained by chemical degradation of a high-molecular-weight fucan with hydrogen peroxide.

The preparation of high-molecular-weight fucans, being fucan 7 to fucan 20, involved numerous different methodologies including treatment with sodium hydroxide, and in some cases other bases as well. The preparation of fucan 7, fucan 8, fucan 11, fucan 12 to fucan 17 and fucan 20 involved a combination of the method discussed in example 12 and tangential flow filtration against a low ionic strength solution. The preparation of fucan 10 involved a combination of cationic augmented tangential flow filtration and sequential tangential flow filtration methods discussed above. Fucan 9, fucan 18 and fucan 19 were extracted from brown seaweed, further processed by tangential flow filtration against a low ionic strength solution and found to be high-molecular-weight fucans.

Example 17: Molecular Weight Determination of Crude Fucans Used to Make Fucan 7 to Fucan Gel permeation chromatography was used to evaluate the molecular weight distributions of crude fucans used to make fucans 7 to 14. Crude fucan 1 refers to the crude fucan used to make fucan 7 and fucan 8. Crude fucan 2 refers to the crude fucan used to make fucan 9, fucan 10, fucan 11 and fucan 13. Crude fucan 3 refers to the crude fucan used to make fucan 12. Crude fucan 4 refers to the crude fucan used to make fucan 14. The results of such analyses are shown in Table 12.

Results in the tables below contain abbreviations used for certain characteristics of a molecular weight distribution. Gel permeation chromatography is denoted by GPC, peak molecular weight is denoted by PMW, weight average molecular weight is denoted by WAMW, number average molecular weight is denoted by NAMW, percentage distribution is denoted by % dist., molecular weight is denoted by MW and polydispersity index is denoted by PDI.

molecular weight distribution profiles for the same twenty fucans shown in Table 13, providing the molecular weight distribution profiles in a different manner that shown in Table 13, providing thereby two different perspectives on the molecular weight distribution of the various fucans. As can be seen from the results, a broad range of different molecular weight distributions in fucans has been accomplished. Fucans with a weight average molecular weight between 28 kDa and 8250 kDa have been obtained with a plurality of distribution profiles.

Results in the tables below contain abbreviations used for certain characteristics of a molecular weight distribution.

TABLE 12

|  | PMW (kDa) | WAMW (kDa) | NAMW (kDa) | % dist. <10 kDa | % dist. <20 kDa | % dist. <50 kDa | % dist. >100 kDa | % dist. >200 kDa | % dist. >500 kDa | PDI |
|---|---|---|---|---|---|---|---|---|---|---|
| Crude fucan 1 | 92.0 | 259.3 | 22.1 | 8.3 | 14.7 | 30.4 | 52.3 | 34.7 | 14.5 | 11.7 |
| Crude fucan 2 | 512.3 | 535.3 | 128.5 | 0.5 | 2.1 | 8.9 | 80.4 | 65.1 | 36.6 | 4.2 |
| Crude fucan 3 | 594.6 | 493.4 | 4.4 | 22.0 | 27.3 | 35.7 | 57.4 | 49.3 | 31.3 | 113.3 |
| Crude fucan 4 | 662.5 | 790.6 | 245.4 | 0.1 | 0.5 | 3.4 | 90.9 | 80.2 | 52.0 | 3.2 |

Example 18: Molecular Weight Determination of Low and High-Molecular-Weight Fucans Gel permeation chromatography was used to evaluate the molecular weight distributions obtained for fucans 1 to 20.

Table 13 and Table 14 list the molecular weight distribution profiles obtained for twenty fucans. Table 14 provides Gel permeation chromatography is denoted by GPC, peak molecular weight is denoted by PMW, weight average molecular weight is denoted by WAMW, number average molecular weight is denoted by NAMW, percentage distribution is denoted by % dist., molecular weight is denoted by MW and polydispersity index is denoted by PDI.

TABLE 13

| A first perspective on the molecular weight distribution of 20 fucans | | | | | | | | | | |
|---|---|---|---|---|---|---|---|---|---|---|
|  | PMW (kDa) | WAMW (kDa) | NAMW (kDa) | % dist. <10 kDa | % dist. <20 kDa | % dist. <50 kDa | % dist. >100 kDa | % dist. >200 kDa | % dist. >500 kDa | PDI |
| Fucan 1 | 17.5 | 28.3 | 14.2 | 16.6 | 51.7 | 87.9 | 3.0 | 0.6 | 0.0 | 1.99 |
| Fucan 2 | 21.0 | 72.4 | 9.9 | 26.5 | 44.0 | 67.3 | 18.4 | 9.1 | 2.3 | 7.29 |
| Fucan 3 | 70.4 | 105.9 | 52.4 | 0.6 | 5.8 | 33.1 | 35.3 | 12.1 | 1.3 | 2.02 |
| Fucan 4 | 107.1 | 136.1 | 79.9 | 0.1 | 1.5 | 15.4 | 53.4 | 19.8 | 1.1 | 1.70 |
| Fucan 5 | 80.2 | 171.9 | 60.4 | 0.8 | 5.3 | 26.5 | 47.9 | 25.4 | 6.6 | 2.84 |
| Fucan 6 | 195.1 | 192.1 | 87.4 | 0.4 | 2.3 | 14.0 | 64.4 | 35.8 | 5.5 | 2.20 |
| Fucan 7 | 242.5 | 366.5 | 137.2 | 0.0 | 0.5 | 7.0 | 77.7 | 54.6 | 21.9 | 2.67 |
| Fucan 8 | 307.1 | 395.8 | 170.2 | 0.0 | 0.2 | 4.0 | 83.8 | 62.2 | 25.4 | 2.33 |
| Fucan 9 | 459.3 | 514.0 | 198.5 | 0.1 | 0.4 | 3.4 | 87.8 | 71.4 | 37.2 | 2.62 |
| Fucan 10 | 390.2 | 497.9 | 228.9 | 0.0 | 0.0 | 1.7 | 90.4 | 73.3 | 35.1 | 2.17 |
| Fucan 11 | 457.3 | 592.8 | 300.9 | 0.0 | 0.0 | 0.7 | 95.4 | 82.9 | 43.8 | 1.97 |
| Fucan 12 | 535.8 | 760.1 | 350.6 | 0.0 | 0.1 | 0.9 | 96.5 | 88.3 | 54.3 | 2.17 |
| Fucan 13 | 612.3 | 857.0 | 448.7 | 0.0 | 0.0 | 0.2 | 98.6 | 92.4 | 61.4 | 1.91 |
| Fucan 14 | 393.1 | 930.1 | 296.6 | 0.0 | 0.0 | 1.1 | 93.6 | 81.1 | 43.6 | 3.14 |
| Fucan 15 | 409.4 | 772.0 | 291.8 | 0.0 | 0.0 | 1.1 | 94.0 | 81.5 | 43.6 | 2.65 |
| Fucan 16 | 743.0 | 1618.0 | 387.5 | 0.0 | 0.1 | 1.4 | 92.9 | 86.6 | 68.2 | 4.18 |
| Fucan 17 | 686.2 | 1876.7 | 524.9 | 0.0 | 0.0 | 0.3 | 98.4 | 93.0 | 69.9 | 3.58 |
| Fucan 18 | 6238.6 | 3957.4 | 519.7 | 0.0 | 0.1 | 1.7 | 82.3 | 78.8 | 71.4 | 7.61 |
| Fucan 19 | 4315.2 | 5336.8 | 2009.5 | 0.0 | 0.0 | 0.0 | 93.7 | 93.3 | 90.1 | 2.66 |
| Fucan 20 | 6170.2 | 8101.9 | 846.3 | 0.0 | 0.0 | 0.3 | 94.7 | 91.1 | 83.6 | 9.57 |

TABLE 14

A second perspective on the molecular weight distribution of 20 fucans

| | % dist. <5 kDa | % dist. between 5-60 kDa | % dist. between 60-200 kDa | % dist. between 200-1600 kDa | % dist. >1600 kDa |
|---|---|---|---|---|---|
| Fucan 1 | 3.5 | 87.9 | 8.1 | 0.6 | 0.0 |
| Fucan 2 | 13.0 | 58.6 | 19.4 | 9.0 | 0.0 |
| Fucan 3 | 0.0 | 41.3 | 46.6 | 12.1 | 0.0 |
| Fucan 4 | 0.0 | 20.9 | 59.1 | 20.1 | 0.0 |
| Fucan 5 | 0.1 | 32.8 | 41.7 | 25.0 | 0.4 |
| Fucan 6 | 0.0 | 18.5 | 45.6 | 35.8 | 0.0 |
| Fucan 7 | 0.0 | 10.0 | 35.4 | 52.3 | 2.4 |
| Fucan 8 | 0.0 | 6.2 | 31.5 | 60.0 | 2.3 |
| Fucan 9 | 0.0 | 5.0 | 23.6 | 67.4 | 4.0 |
| Fucan 10 | 0.0 | 3.0 | 23.7 | 69.8 | 3.5 |
| Fucan 11 | 0.0 | 1.3 | 15.8 | 78.0 | 4.9 |
| Fucan 12 | 0.0 | 1.3 | 10.5 | 78.9 | 9.4 |
| Fucan 13 | 0.0 | 0.3 | 7.2 | 80.4 | 12.0 |
| Fucan 14 | 0.0 | 1.8 | 16.3 | 68.7 | 13.1 |
| Fucan 15 | 0.0 | 1.7 | 16.1 | 72.4 | 9.8 |
| Fucan 16 | 0.0 | 2.1 | 9.4 | 60.9 | 37.6 |
| Fucan 17 | 0.0 | 0.5 | 6.5 | 62.4 | 30.6 |
| Fucan 18 | 0.0 | 2.3 | 5.7 | 35.2 | 56.8 |
| Fucan 19 | 0.0 | 0.0 | 0.3 | 24.9 | 74.8 |
| Fucan 20 | 0.0 | 0.6 | 5.2 | 28.7 | 65.5 |

Example 19: Sulfate, Total Carbohydrate and Monosaccharide Content of High-Molecular-Weight Fucans High-molecular-weight fucans fucan 7 to fucan 18 and fucan 20 were dissolved in deionized water, hydrolyzed under acidic conditions and analyzed by inductively coupled plasma mass spectrometry (ICP-MS) for % w/w total sulfur content, performed by ALS Environmental laboratories in Burnaby, British Columbia. Sulfur content was converted to sulfate content by multiplying the sulfur content by the molar ratio of sulfate to sulfur to obtain % w/w sulfate content of the fucan. The sulfate contents of fucan 7 to 18 and fucan 20 are shown in table 15 below.

TABLE 15

Sulfate content of fucan 7 to fucan 18 and fucan 20

| | Sulfate content (% w/w) |
|---|---|
| Fucan 7 | 23.93 |
| Fucan 8 | 40.95 |
| Fucan 9 | 40.32 |
| Fucan 10 | 33.15 |
| Fucan 11 | 44.87 |
| Fucan 12 | 41.02 |
| Fucan 13 | 36.18 |
| Fucan 14 | 40.45 |
| Fucan 15 | 39.79 |
| Fucan 16 | 14.39 |
| Fucan 17 | 51.30 |
| Fucan 18 | 21.11 |
| Fucan 20 | 25.60 |

High-molecular-weight fucans fucan 7, fucan 11, fucan 16, fucan 18 and fucan 20 were analyzed for total carbohydrate and monosaccharide composition by gas spectrometry-mass spectroscopy (GC-MS) performed by the complex carbohydrate research center at the University of Georgia. The high-molecular-weight fucans were derivatized by acidic methanolysis to produce O-trimethylsilyl (O-TMS) derivatives. After derivatization, the fucans are analyzed on an Agilent 7890A gas chromatography system interfaced to an Agilent 5975C mass spectrometry detector using a Supelco Equity-1 fused silica capillary column (30 m, 0.25 mm inner diameter). The results for the total carbohydrate content and the monosaccharide composition of the high-molecular-weight fucans are shown in table 16 below. Carbohydrate in the table below is abbreviated "carb.".

TABLE 16

Total carbohydrate and monosaccharide composition of five fucans

| | Total carb. content (% w/w of the fucan) | Fucose (% w/w of the total carb. content) | Galactose (% w/w of total carb. content) | Xylose (% w/w of total carb. content) | Mannose (% w/w of total carb. content) | Rhamnose (% w/w of total carb. content) |
|---|---|---|---|---|---|---|
| Fucan 7 | 32.7 | 44.4 | 52.9 | 0.5 | 0.4 | 0.3 |
| Fucan 11 | 59.5 | 91.9 | 8.1 | 0.0 | 0.0 | 0.0 |
| Fucan 16 | 25.9 | 48.3 | 9.9 | 15.5 | 5.9 | 0.3 |
| Fucan 18 | 41.2 | 92.0 | 4.7 | 2.1 | 0.4 | 0.2 |
| Fucan 20 | 30.1 | 84.7 | 10.6 | 3.3 | 0.9 | 0.0 |

Example 20: Rat Epidural Adhesion Treatment

Fucoidan solutions using the twenty fucans identified in the example 18 were prepared in Lactated Ringers Injection USP (LRS). Fucan 1 to fucan 16, fucan 18 and fucan 20 were prepared at 100 mg/mL in LRS. Fucan 19 was prepared at 50 mg/mL in LRS. Fucan 17 was prepared at 500 mg/mL in LRS. Laminectomy surgery was performed on Sprague Dawley rats, the average weights of the rats and the dose in milligram per kilogram shown in table 17 below. A line block along the lumbar spine was created with bupivacaine solution. The back of the rat was cleaned and then covered with sterile drapes. The lumbar fascia was opened through a midline skin incision, lumbosacral fascia was incised and the paralumbar muscles was dissected to expose the underlying vertebral laminae. Bone at the centre of the vertebrae was removed. Throughout the procedure, haemostasis was maintained by irrigation with Lactated Ringer's Injection USP (LRS) and pressure with cotton swabs. The exposed dura was treated directly with 15 microlitres of LRS (control) or fucoidan solution. The muscle and skin layers were closed with sutures and the rats were allowed to recover for one week before sacrifice for adhesion quantification. The presence and size of adhesions on the dura were noted. The dimensions of the adhesions and the exposed dura were recorded and used to calculate an adhesion coverage percentage, being the adhesion area as a percentage of the total exposed dura area.

Adhesion coverage (%)=100×epidural adhesion area÷total exposed dura area  Equation 1:

The control group receiving LRS was determined to have a 65% adhesion coverage using equation 1. The adhesion coverage for the twenty fucans disclosed in Table 13 to Table 16 are shown in Table 17 below as the reduction in adhesion coverage relative to the control group. A negative value denoted where an increase in adhesion coverage was seen relative to the control group.

TABLE 17

Reduction in rat epidural adhesion relative to control LRS using 20 different fucans

| | Average Rat Weight (kg) | Dose (mg) | Dose per animal weight (mg/kg) | Number of rats scored | % Reduction in epidural adhesion coverage vs. control |
|---|---|---|---|---|---|
| Fucan 1 | 0.41 | 1.5 | 3.7 | 4 | −40% (i.e., 40% increase in fibrous adhesions compared to control) |
| Fucan 2 | 0.59 | 1.5 | 2.5 | 3 | 9% |
| Fucan 3 | 0.39 | 1.5 | 3.8 | 4 | −10% |
| Fucan 4 | 0.65 | 1.5 | 2.3 | 4 | 83% |
| Fucan 5 | 0.53 | 1.5 | 2.9 | 4 | 46% (i.e., 46% decrease in fibrous adhesions compared to control) |
| Fucan 6 | 0.46 | 1.5 | 3.3 | 4 | 44% |
| Fucan 7 | 0.47 | 1.5 | 3.2 | 3 | 100% |
| Fucan 8 | 0.36 | 1.5 | 4.2 | 3 | 100% |
| Fucan 9 | 0.39 | 1.5 | 3.8 | 2 | 100% |
| Fucan 10 | 0.40 | 1.5 | 3.8 | 4 | 100% |
| Fucan 11 | 0.58 | 1.5 | 2.6 | 2 | 100% |
| Fucan 12 | 0.44 | 1.5 | 3.4 | 2 | 100% |
| Fucan 13 | 0.64 | 1.5 | 2.3 | 3 | 100% |
| Fucan 14 | 0.37 | 1.5 | 4.0 | 4 | 100% |
| Fucan 15 | 0.50 | 1.5 | 3.0 | 3 | 100% |
| Fucan 16 | 0.45 | 1.5 | 3.3 | 3 | 100% |
| Fucan 17 | 0.59 | 7.5 | 12.8 | 3 | 100% |
| Fucan 18 | 0.59 | 1.5 | 2.5 | 2 | 100% |
| Fucan 19 | 0.39 | 0.8 | 1.9 | 3 | 100% |
| Fucan 20 | 0.56 | 1.5 | 2.7 | 2 | 100% |

As may be seen by comparing the results of Table 17 with the molecular weight of the fucans given in Tables 13 and Table 14, fucans with a weight average molecular weight over 130 kDa and containing about 60% or more of their molecular weight distribution above 100 kDa show greater efficacy in the inhibition, prevention, removal, reduction, or other treatment of rat epidural adhesions than fucans with weight average molecular weight below 100 kDa containing about 60% or less of their molecular weight distribution above 100 kDa at the same dose. There is also a further indication that fucans with weight average molecular weight above 300 kDa, containing about 70% or more of their molecular weight distribution above 100 kDa show even greater efficacy in the inhibition, prevention, removal, reduction, or other treatment of rat epidural adhesions at the same dose.

Example 21: Rabbit Uterine Horn Adhesion Treatment with Fucan 1 and Fucan 10

Uterine horn surgery was performed on both uterine horns in each rabbit. Prior to surgery, the rabbits were weighed and then prepared for surgery by premedication with ketamine and xylazine.

Fucoidan solution was prepared at 0.07 mg/mL in Lactated Ringers Injection USP, sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. 15 mL/kg fucoidan solution per rabbit weight was applied to the abdominal cavity before the incision was closed. Adhesion was evaluated two weeks after the surgery. Length of the uterine horn adhesion was measured with a ruler. The uterine horn adhesion coverage percentage, being the length of the adhesion as a percentage of the total damaged uterine horn length was calculated as:

Adhesion coverage (%)=100×uterine horn adhesion length÷total damaged uterine horn length  Equation 2:

The same surgical method was applied to 3 New Zealand White rabbits, receiving 15 mL/kg of control Lactated Ringer's Injection USP (LRS) instead of fucoidan solution.

The control group receiving LRS was determined to have a 41% adhesion coverage using equation 2. Table 18 shows the results obtained using the method discussed above for fucans fucan 1 and fucan 10, being representative examples of respectively a fucan with the majority of its molecular weight distribution below 100 kDa and even below 50 kDa and a fucan with the majority of its molecular weight distribution above 100 kDa and even above 200 kDa. The results in the table below are shown as the reduction in adhesion coverage relative to the control group.

TABLE 18

Reduction in rabbit uterine horn adhesion using two different fucans relative to control LRS

| | Dose per animal weight (mg/kg) | Number of Uterine Horns | % Reduction in uterine horn adhesion coverage vs. control |
|---|---|---|---|
| Fucan 1 - low molecular weight | 1 | 6 | 21% (i.e., 21% decrease in fibrous adhesions compared to control) |
| Fucan 10 - high-molecular-weight | 1 | 8 | 100% |

As may be seen from the results in Table 18, fucans having the majority of their distribution above 100 kDa, or even above 200 kDa, have a higher efficacy in the inhibition, prevention, removal, reduction, or other treatment of rabbit uterine horn adhesion as compared with fucans having a majority of their distribution under 100 kDa or even under 50 kDa at the same dose.

Example 22: Rabbit Uterine Horn Adhesion with Fucan 17

To determine the efficacy of the high-molecular-weight fucan 17 in inhibiting surgical adhesions, the following double uterine horn (DUH) surgeries were performed on both horns of a total of three New Zealand White rabbits. Prior to surgery, the rabbits were weighed and then prepared for surgery by premedication with ketamine and xylazine.

Fucoidan solution was prepared at 5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. The top third and the bottom third of the muscle incision was closed and 5 mL/kg fucoidan solution per rabbit weight was applied to the abdominal cavity. The muscle incision was temporarily closed and the fucoidan solution left in the abdominal cavity for 30 minutes. The muscle incision was reopened and the abdominal cavity was flushed with 10 mL/kg LRS. The majority of the fluid in the abdominal cavity was suctioned out before the incision was closed. Adhesion formation was evaluated two weeks after the surgery. Length of the uterine horn adhesion was measured with a ruler. The uterine horn adhesion coverage percentage, being the length of the adhesion as a percentage of the total damaged uterine horn length was calculated using equation 2.

Table 19 shows the results obtained using the method discussed above for fucan 17, being a representative example of a high-molecular-weight fucan. The results in the table below are shown as the mean adhesion length across the 6 uterine horns scored.

Table 19 provides the results of treating six uterine horns with fucan 17.

TABLE 19

Adhesion length using fucan 17

| | Dose (mg/kg) | Number of Uterine Horns | Mean % adhesion length |
|---|---|---|---|
| Fucan 17 | 25 | 6 | 0% (i.e., no adhesions were found) |

As may be seen from the results of Table 19, high-molecular-weight fucans may be used to successfully inhibit, prevent, remove, reduce, or otherwise treat post-surgical uterine horn adhesions.

Example 23: Uterine Horn Fibrous Adhesion Treated with a High-Molecular-Weight Fucan Composition To determine the efficacy of a high-molecular-weight fucan composition comprising a number average molecular weight of about 228 kDa, a weight average molecular weight of about 1210 kDa, a peak molecular weight of about 575 kDa and having a molecular weight distribution wherein about 89% of the distribution is above 100 kDa and wherein about 30% of the distribution is above 1000 kDa, in inhibiting surgical adhesions, the following double uterine horn (DUH) surgeries were performed on both horns of a total of twenty New Zealand White rabbits. Prior to surgery, the rabbits were weighed and then prepared for surgery by premedication with midazolam and dexmeditomidine.

Fucoidan solution was prepared at each concentration of 0.02 mg/mL, 0.1 mg/mL, 0.5 mg/mL, or 2.5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 2 mL/kg fucoidan solution per rabbit weight was applied to the abdominal cavity before the incision was closed. Adhesion was evaluated two weeks after the surgery. Five rabbits were treated and evaluated for each fucoidan concentration prepared. Length of the uterine horn adhesion was measured with a ruler. The uterine horn adhesion length was calculated using equation 2.

The same surgical method was applied to 5 additional New Zealand White rabbits for control, each receiving about 2 mL/kg of control Lactated Ringer's Injection USP (LRS) instead of fucoidan solution. The control group receiving LRS was determined to have a 100% adhesion coverage using equation 2. Table 20 shows the results obtained using the method discussed above for the high-molecular-weight fucan composition at different concentrations and dosages (in total forty uterine horns were treated, 10 each for each concentration of the high-molecular-weight fucan composition); the results are shown as the reduction in adhesion coverage relative to the control group.

TABLE 20

Decrease in rabbit uterine horn adhesion using a high-molecular-weight fucan composition relative to control LRS

| Concentration (mg/mL) | Dose (mg/kg) | Number of Uterine Horns | % Reduction in uterine horn adhesion coverage vs. control |
|---|---|---|---|
| 0.02 | 0.04 | 10 | 10% (i.e., 10% decrease in fibrous adhesions compared to control) |
| 0.1 | 0.2 | 10 | 30% (i.e., 30% decrease in fibrous adhesions compared to control) |
| 0.5 | 1 | 10 | 71% (i.e., 71% decrease in fibrous adhesions compared to control) |
| 2.5 | 5 | 10 | 95% (i.e., 95% decrease in fibrous adhesions compared to control) |

As can be seen from the results of Table 20, high-molecular-weight fucan compositions can be used to successfully inhibit, prevent, remove, reduce, or otherwise treat post-surgical uterine horn adhesions.

REFERENCE NUMERAL LIST

100 Molecular weight based segmentation system (higher-to-lower)
100' Molecular weight based segmentation system (lower-to-higher)
100" Cation-augmented TFF system (CATS)
102 Input supply line
104 Pre-filter
106 Lower MWCO subsystem retentate-line valve
106' Lower MWCO subsystem output valve
108 lower MWCO subsystem retentate output line
110 Higher molecular weight cut-off TFF filter
111 Higher MWCO subsystem retentate output line
112 Higher MWCO TFF filter supply line
113 Higher-to-lower MWCO inter-subsystem valve
114 Higher MWCO subsystem pump
115 Higher MWCO subsystem solvent supply line
116 Higher MWCO subsystem fucan container
117 Higher MWCO subsystem solvent container
118 Higher MWCO subsystem retentate return line
119 Higher MWCO subsystem permeate output line
120 Lower molecular weight cut-off TFF filter
121 Lower MWCO subsystem retentate output line
122 Lower MWCO TFF filter supply line
123 Lower-to-higher MWCO inter-subsystem valve
124 Lower MWCO subsystem pump
125 Lower MWCO subsystem solvent supply line
126 Lower MWCO subsystem fucan container
127 Lower MWCO subsystem solvent container
128 Lower MWCO subsystem retentate return line
129 Lower MWCO subsystem permeate output line
130 Higher MWCO TFF subsystem
130' Higher MWCO TFF subsystem (FIG. 3)
135 Cationic additive flush solution supply line
136 Cationic additive flush solution valve
137 Cationic additive flush solution container
140 Lower MWCO subsystem
140' Lower MWCO TFF subsystem (FIG. 3)
142 Sodium salt solution container
143 Low conductivity diafiltration solution container
144 Sodium salt solution control valve
145 Low conductivity diafiltration solution valve
146 Sodium salt solution supply line
147 Low conductivity diafiltration solution supply line
150 Higher MWCO TFF filter
160 Lower MWCO TFF filter
600 Centrifugal precipitation system for obtaining a high-molecular-weight fucan from a starting fucan composition
600' Centrifugal precipitation system for obtaining a high-molecular-weight fucan from a starting fucan composition
610 Centrifuge container
620 Gradated permeable barrier
620' Permeable barrier
620a Barrier segment (first—highest density)
620b Barrier segment (second—intermediate density)
620c Barrier segment (third—lowest density)
620c' Single barrier segment
622 First-bottom gradated permeable barrier material end
622' First-bottom permeable barrier material end
624 Second-top gradated permeable barrier material end
624' Second-top permeable barrier material end
630 First-bottom end of centrifuge container 610
640 Second-top end of centrifuge container 610
650 Starting fucan composition
660 Arrow indicating direction of centrifugal force on container 610
670 Centrifuge box
900 Electrophoresis-extraction system
910 Electrophoresis chamber
912 Well
914 Theoretical Displacement distances
916 Electrophoresis gel
918 Electrophoresis buffer
920 Direct current power supply
922 Cathode
924 Anode
926 Migration direction arrow (depicting displacement direction of anions)
800 Membrane dialysis system for obtaining a high-molecular-weight fucan from a starting fucan composition
801 Input supply line
802 Pre-filter
810 Fucan container
812 Dialysis system supply line
814 Dialysis system pump
815 Dialyzed fluid output valve
816 Dialyzed fluid return line
818 Dialyzed fluid output line
820 Dialysis cell
825 Dialysis membrane
830 Dialysis container
832 Dialysate supply line
834 Dialysate pump
835 Dialysate fluid output valve
836 Dialysate fluid return line
838 Dialysate fluid output line
840 Dialysate container
842 Dialysate supply line
845 Dialysate supply valve
170 Tangential flow filtration (TFF) subsystem
171 TFF filter
172 TFF subsystem filter supply line
173 TFF subsystem solvent supply valve
174 TFF subsystem pump
175 TFF subsystem solvent supply line
176 TFF subsystem fucan container
177 TFF subsystem solvent container
178 TFF subsystem retentate line 179 TFF subsystem permeate output line
180 Ion exchange subsystem
181 Ion exchange container
182a Ion exchange subsystem fucan supply line
182b Ion exchange subsystem salt solution supply line
183a Ion exchange subsystem fucan return valve
183b Ion exchange subsystem salt solution supply valve
183c Ion exchange subsystem salt solution return valve
184a Ion exchange subsystem fucan pump
184b Ion exchange subsystem salt solution pump
186 Ion exchange subsystem fucan container
187 Ion exchange subsystem salt solution container
188a Ion exchange subsystem fucan return line
188b Ion exchange subsystem salt solution return line
189 Macroporous ion exchange resin
300 Ion adsorption system
301 Input supply line
302 Inter-subsystem valve
303 TFF subsystem retentate output line
304 Ion exchange subsystem output valve
305 Ion exchange subsystem output line
306 Pre-filter All terms used herein are used in accordance with their ordinary meanings unless the context or definition clearly indicates otherwise. Also unless expressly indicated otherwise, in this disclosure the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates otherwise.

Unless otherwise indicated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present methods, compositions, systems, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A high-molecular-weight fucan wherein the high-molecular-weight fucan consists essentially of a molecular weight distribution wherein at least 60% w/w of the molecular weight distribution of the fucan is greater than about 1600 kDa when measured using an aqueous gel permeation chromatography set up consisting essentially of:
one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;
a refractive index detector at about 30° C.;
0.1M sodium nitrate mobile phase run at 0.6 mL/min; and
quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

2. The high-molecular-weight fucan of claim 1, wherein the sulfate content is between about 20% w/w and 60% w/w.

3. The high-molecular-weight fucan of claim 1, wherein the total carbohydrate content is between about 27% w/w and 80% w/w.

4. The high-molecular-weight fucan of claim 3, wherein the total fucose content as a percentage of the total carbohydrate content is at least about 30% w/w.

5. The high-molecular-weight fucan of claim 3, wherein the total galactose content as a percentage of the total carbohydrate content is below about 60% w/w.

6. The high-molecular-weight fucan of claim 3, wherein the total of glucuronic acid, mannose, rhamnose, glucose and xylose content as a percentage of the total carbohydrate content is below about 30% w/w.

7. The high-molecular-weight fucan of claim 1 wherein the high-molecular-weight fucan when dissolved in water at a concentration of 50 mg/mL has a viscosity of between about 4 cP and 50 cP.

8. The high-molecular-weight fucan of claim 1 wherein the high-molecular-weight fucan is a white solid.

9. The high-molecular-weight fucan of claim 1 wherein the high-molecular-weight fucan when dissolved in water at a concentration from 1 mg/mL through 100 mg/mL forms a solution that is clear and colorless.

10. The high-molecular-weight fucan of claim 1 wherein the fucan comprises less than 5% w/w acetyl content.

11. The high-molecular-weight fucan of claim 1 wherein the fucan comprises an acetyl content of substantially 0% w/w when measured by 2D 1H-13C heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

12. A medically acceptable fucan composition comprising a therapeutically effective amount of the high-molecular-weight fucan of claim 1 in a medically acceptable buffer or diluent.

13. A medical composition comprising between about 0.02 mg/mL and 100 mg/mL of the high-molecular-weight fucan of claim 1, wherein the medical composition is configured and composed to treat a disease or condition in an animal.

14. The medical composition of claim 13 wherein the disease or condition is a fibrous adhesion.

15. The high-molecular-weight fucan of claim 2, wherein the total carbohydrate content is between about 27% w/w and 80% w/w.

16. The high-molecular-weight fucan of claim 2 wherein the fucan comprises less than 5% w/w acetyl content.

17. The high-molecular-weight fucan of claim 3 wherein the fucan comprises less than 5% w/w acetyl content.

18. The high-molecular-weight fucan of claim 15 wherein the fucan comprises less than 5% w/w acetyl content.

\* \* \* \* \*